US012705325B2

(12) United States Patent
Kiani et al.

(10) Patent No.: US 12,705,325 B2
(45) Date of Patent: Aug. 11, 2026

(54) DISPLAY LAYOUT AND INTERACTIVE OBJECTS FOR PATIENT MONITORING

(71) Applicant: Masimo Corporation, Irvine, CA (US)

(72) Inventors: Massi Joe E. Kiani, Laguna Niguel, CA (US); Bilal Muhsin, San Clemente, CA (US); Ammar Al-Ali, San Juan Capistrano, CA (US); Nicholas Evan Barker, Laguna Beach, CA (US); Chad A. DeJong, Los Angeles, CA (US); Omar Ahmed, Lake Forest, CA (US); Keith Ward Indorf, Riverside, CA (US); Steve Coon, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 19/028,557

(22) Filed: Jan. 17, 2025

(65) Prior Publication Data

US 2025/0232019 A1 Jul. 17, 2025

Related U.S. Application Data

(63) Continuation of application No. 17/073,133, filed on Oct. 16, 2020, now Pat. No. 12,235,941.

(Continued)

(51) Int. Cl.

| | |
|---|---|
| ***G06F 21/32*** | (2013.01) |
| ***G16H 10/60*** | (2018.01) |
| ***G16H 40/20*** | (2018.01) |
| ***G16H 40/67*** | (2018.01) |
| ***G16H 50/50*** | (2018.01) |
| ***G16H 80/00*** | (2018.01) |
| *A61B 5/00* | (2006.01) |

(52) U.S. Cl.

CPC ............ *G06F 21/32* (2013.01); *G16H 10/60* (2018.01); *G16H 40/20* (2018.01); *G16H 40/67* (2018.01); *G16H 50/50* (2018.01); *G16H 80/00* (2018.01); *A61B 5/0024* (2013.01)

(58) Field of Classification Search

CPC .......... G06F 21/32; G06F 3/048; G06F 21/31; G16H 10/60; G16H 40/20; G16H 40/67; G16H 50/50; G16H 80/00; G16H 40/63; A61B 5/0024

See application file for complete search history.

(56) References Cited

U.S. PATENT DOCUMENTS

| | | | |
|---|---|---|---|
| D394,852 | S | 6/1998 | Levin |
| 8,695,254 | B2 | 4/2014 | Bell et al. |

(Continued)

FOREIGN PATENT DOCUMENTS

| | | |
|---|---|---|
| JP | 2003-088561 | 3/2003 |
| JP | 2006-019841 | 1/2006 |

(Continued)

*Primary Examiner* — Towfiq Elahi

(74) *Attorney, Agent, or Firm* — Knobbe, Martens, Olson & Bear, LLP

(57) ABSTRACT

A physiological patient monitoring system with a healthcare professional-facing interface is disclosed. The healthcare professional interface may only display by default the most critical non-confidential patient information. To access the full range of features in the system, clinicians can unlock the device. Once unlocked, clinicians can access all of a patient's treatment history, and all the data may be consolidated and presented intuitively.

20 Claims, 59 Drawing Sheets

Related U.S. Application Data

(60) Provisional application No. 63/017,151, filed on Apr. 29, 2020, provisional application No. 62/923,248, filed on Oct. 18, 2019.

(56) References Cited

U.S. PATENT DOCUMENTS

| | | | |
|---|---|---|---|
| 11,424,025 B2 | 8/2022 | Page | |
| 11,803,623 B2 | 10/2023 | Kiani et al. | |
| D1,030,789 S | 6/2024 | Kuwatani | |
| D1,031,729 S | 6/2024 | Forrest et al. | |
| 12,066,426 B1 | 8/2024 | Lapotko et al. | |
| D1,042,596 S | 9/2024 | DeJong et al. | |
| D1,042,852 S | 9/2024 | Hwang | |
| 12,082,926 B2 | 9/2024 | Sharma et al. | |
| D1,048,571 S | 10/2024 | Yu et al. | |
| D1,048,908 S | 10/2024 | Al-Ali et al. | |
| 12,106,752 B2 | 10/2024 | Campbell et al. | |
| 12,114,974 B2 | 10/2024 | Al-Ali et al. | |
| 12,126,683 B2 | 10/2024 | Koo et al. | |
| 12,127,838 B2 | 10/2024 | Olsen et al. | |
| 12,128,213 B2 | 10/2024 | Kiani et al. | |
| 12,131,661 B2 | 10/2024 | Pauley et al. | |
| D1,050,910 S | 11/2024 | Al-Ali et al. | |
| 12,133,717 B2 | 11/2024 | Al-Ali et al. | |
| 12,178,572 B1 | 12/2024 | Pauley et al. | |
| 12,178,581 B2 | 12/2024 | Telfort et al. | |
| 12,178,852 B2 | 12/2024 | Kiani et al. | |
| D1,057,159 S | 1/2025 | DeJong et al. | |
| D1,057,160 S | 1/2025 | DeJong et al. | |
| 12,198,790 B1 | 1/2025 | Al-Ali | |
| 12,200,421 B2 | 1/2025 | Campbell et al. | |
| 12,207,901 B1 | 1/2025 | Lapotko et al. | |
| D1,060,680 S | 2/2025 | Al-Ali et al. | |
| D1,061,585 S | 2/2025 | Indorf | |
| D1,063,893 S | 2/2025 | DeJong et al. | |
| 12,220,207 B2 | 2/2025 | Telfort et al. | |
| 12,235,941 B2 | 2/2025 | Kiani et al. | |
| 12,235,947 B2 | 2/2025 | Kiani et al. | |
| 12,236,767 B2 | 2/2025 | Muhsin | |
| D1,066,244 S | 3/2025 | Lim et al. | |
| D1,066,672 S | 3/2025 | Al-Ali et al. | |
| D1,068,656 S | 4/2025 | Trevisan et al. | |
| D1,071,195 S | 4/2025 | Seung | |
| D1,072,836 S | 4/2025 | Indorf | |
| D1,072,837 S | 4/2025 | Ahmed et al. | |
| 12,272,445 B1 | 4/2025 | Kiani | |
| D1,078,689 S | 6/2025 | Hwang | |
| D1,079,020 S | 6/2025 | Hwang | |
| 12,336,796 B2 | 6/2025 | Al-Ali | |
| 12,433,524 B2 | 10/2025 | Al-Ali et al. | |
| 2001/0045037 A1 | 11/2001 | Bank et al. | |
| 2010/0056912 A1* | 3/2010 | Urness | G16H 40/67 600/437 |
| 2011/0199214 A1 | 8/2011 | Gawlick | |
| 2011/0202490 A1 | 8/2011 | Gawlick | |
| 2024/0252046 A1 | 8/2024 | Jansen et al. | |
| 2024/0306985 A1 | 9/2024 | Vo et al. | |
| 2024/0324953 A1 | 10/2024 | Telfort | |
| 2024/0380246 A1 | 11/2024 | Moran | |
| 2024/0380247 A1 | 11/2024 | Moran | |
| 2024/0404549 A1 | 12/2024 | Campbell et al. | |
| 2025/0000458 A1 | 1/2025 | Abdul-Hafiz et al. | |
| 2025/0037836 A1 | 1/2025 | Kiani | |
| 2025/0100482 A1 | 3/2025 | Al-Ali et al. | |
| 2025/0118415 A1 | 4/2025 | Olsen | |

FOREIGN PATENT DOCUMENTS

| | | |
|---|---|---|
| JP | 2006-209583 | 8/2006 |
| JP | 2011-186661 | 9/2011 |
| JP | 2013-541782 | 11/2013 |
| JP | 2014-171776 | 9/2014 |
| JP | 2016-184427 | 10/2016 |
| JP | 2017-146936 | 8/2017 |
| JP | 2018-018531 | 2/2018 |
| JP | 2019-075148 | 5/2019 |

* cited by examiner

FIG. 2I
BED LABEL
2037 A
Do Not Enter
Procedure in Progress
Latex Sensitivity
Precautions
Fall Risk
No Food • No Drink
BED LABEL
2037 B
Do Not Enter
Procedure in Progress
Fall Risk
No Food • No Drink

600

NSmith

| LABEL | MRN | ROOM | DIAGNOSIS |
|---|---|---|---|
| Nsmith | 9870067 | 201a | Influenza |

Labs 2019-12-11
Labs 2019-12-10
Labs 2019-12-09
X-Rays 2019-12-09
Labs 2019-12-08

602

| TEST | RESULT | FLAG | NORMAL RANGE LOW | HIGH | MEASURE |
|---|---|---|---|---|---|
| Album | 3.7 | | 2.7 | 4.4 | g/dL |
| Globolin | 2.1 | | 1.6 | 3.6 | g/dL |
| A/G Ratio | 1.8 | | 0.8 | 2.0 | Ratio |
| ALT (SGPT) | 23 | | 12 | 118 | U/L |
| ALK Phosphatase | 121 | | 5 | 131 | U/L |
| Urea Nitrogen | 21 | | 6 | 31 | mg/dL |
| Creatine | 0.6 | | 0.5 | 1.6 | mg/dL |
| Glucose | 111 | | 70 | 27 | mg/dL |
| Potassium | 4.6 | | 3.6 | 138 | 10^3/mL |
| WBC | 11.2 | | 4.0 | 15.5 | 10^3/mL |
| RB | 7.8 | | 4.8 | 9.3 | 10^3/mL |
| Hemoglobin | 17.7 | | 12.1 | 20.3 | g/dL |
| Hematocrit | 55 | | 36 | 60 | % |
| MCV | 71 | | 58 | 79 | fL |
| MCH | 22.7 | | 19 | 28 | pg |
| MCHC | 32.2 | | 30 | 38 | g/dL |
| Platelet Count | 266 | | 170 | 400 | 10^3/mL |
| PLatelet EST | Adequate | | | e | |
| Neutropolis | 42 | L | 60 | 77 | % |
| Bands | 0 | | 0 | 3 | % |
| Lymphocytes | 40 | H | 12 | 30 | % |
| Monocytes | 4 | | 3 | 10 | % |
| Eosinophilis | 14 | H | 2 | 10 | % |

601

Patient Dashboard | Timeline | Live Data | Labs & Imagery | Medication & Schedule | Patient's Questions

FIG. 6A

Figure 6C:
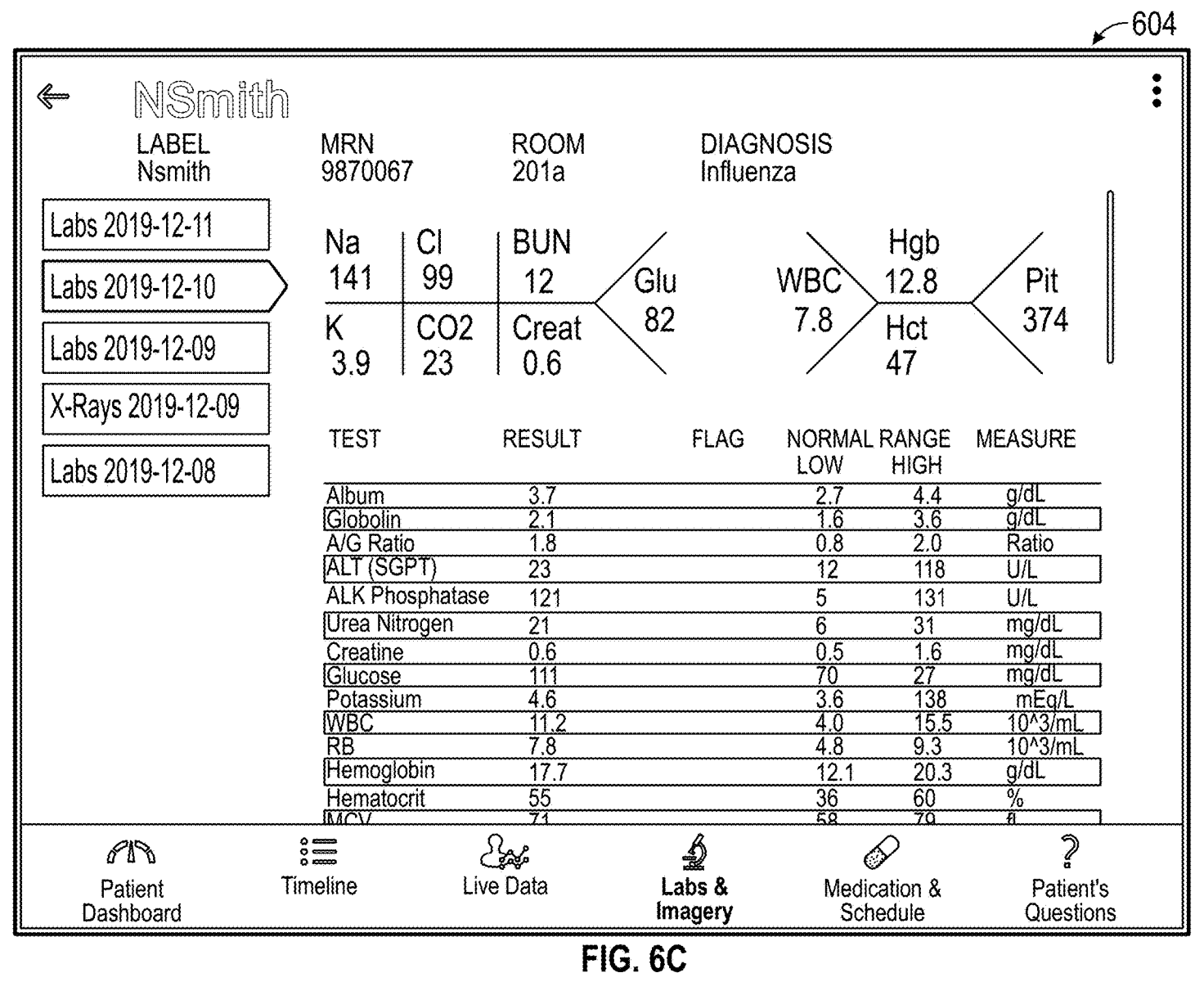

| TEST | RESULT | FLAG | NORMAL RANGE LOW | HIGH | MEASURE |
|---|---|---|---|---|---|
| Album | 3.7 | | 2.7 | 4.4 | g/dL |
| Globolin | 2.1 | | 1.6 | 3.6 | g/dL |
| A/G Ratio | 1.8 | | 0.8 | 2.0 | Ratio |
| ALT (SGPT) | 23 | | 12 | 118 | U/L |
| ALK Phosphatase | 121 | | 5 | 131 | U/L |
| Urea Nitrogen | 21 | | 6 | 31 | mg/dL |
| Creatine | 0.6 | | 0.5 | 1.6 | mg/dL |
| Glucose | 111 | | 70 | 27 | mg/dL |
| Potassium | 4.6 | | 3.6 | 138 | mEq/L |
| WBC | 11.2 | | 4.0 | 15.5 | 10^3/mL |
| RB | 7.8 | | 4.8 | 9.3 | 10^3/mL |
| Hemoglobin | 17.7 | | 12.1 | 20.3 | g/dL |
| Hematocrit | 55 | | 36 | 60 | % |
| MCV | 71 | | 58 | 79 | fl |

NSmith

LABEL Nsmith | MRN 9870067 | ROOM 201a | DIAGNOSIS Influenza

Labs 2019-12-11

Labs 2019-12-10

Labs 2019-12-09

X-Rays 2019-12-09

Labs 2019-12-08

Na 141 | Cl 99 | BUN 12 | Glu 82

K 3.9 | CO2 23 | Creat 0.6

WBC 7.8 | Hgb 12.8 | Hct 47 | Pit 374

PT 11 | PTT 29 | INR 1.1

| TEST | RESULT | FLAG | NORMAL RANGE LOW | HIGH | MEASURE |
|---|---|---|---|---|---|
| Album | 3.7 | | 2.7 | 4.4 | g/dL |
| Globolin | 2.1 | | 1.6 | 3.6 | g/dL |
| A/G Ratio | 1.8 | | 0.8 | 2.0 | Ratio |
| ALT (SGPT) | 23 | | 12 | 118 | U/L |
| ALK Phosphatase | 121 | | 5 | 131 | U/L |
| Urea Nitrogen | 21 | | 6 | 31 | mg/dL |
| Creatine | 0.6 | | 0.5 | 1.6 | mg/dL |
| Glucose | 111 | | 70 | 27 | mg/dL |
| Potassium | 4.6 | | 3.6 | 138 | mEq/L |
| WBC | 11.2 | | 4.0 | 15.5 | 10^3/mL |
| RB | 7.8 | | 4.8 | 9.3 | 10^3/mL |
| Hemoglobin | 17.7 | | 12.1 | 20.3 | g/dL |
| Hematocrit | 55 | | 36 | 60 | % |
| MCV | 71 | | 58 | 79 | fL |
| MCH | 22.7 | | 19 | 28 | pg |

Patient Dashboard | Timeline | Live Data | Labs & Imagery | Medication & Schedule | Patient's Questions

FIG. 6D

Settings

- Patient/ Room/ Warnings
- Home Screen
- Patient Dashboard
- Timeline
- Medication & Schedule
- Live Data
- Labs & Imagery
- Patient's Questions

| MEDICATION | DOSIS | FREQUENCY | TIME |
|---|---|---|---|
| Glipizide | 8mg | 4x daily | 6am/ 10am 2pm/ 6pm |
| Apirin | 81mg | as needed max. 2/day | 30 min after meal |
| Lisnopril | 20mg | as needed max. 2/day | 30 min after meal |
| Metforin | 100mg | 1x daily | 6:30pm/ 30 min after meal |

| SCHEDULE | TIME |
|---|---|
| Cup of water | 09:00 am |
| Ten minute walk | 11:00 am |
| Physical Therapy | 04:30 pm |
| Bed time | 10:00 pm |

FIG. 9L

No BP'S or Venipuncture on Left Arm

No Visitors! Check in at Nurse Station

Quiet Zone! Patient Sleeping. Please see nurse before entering.

Safety

No Food • No Drink

DISPLAY LAYOUT AND INTERACTIVE OBJECTS FOR PATIENT MONITORING

CROSS REFERENCE TO PRIORITY APPLICATIONS

This application is a continuation of U.S. application Ser. No. 17/073,133, filed Oct. 16, 2020, titled "DISPLAY LAYOUT AND INTERACTIVE OBJECTS FOR PATIENT MONITORING", which claims the benefit of priority to U.S. Provisional Patent Application No. 62/923,248, filed Oct. 18, 2019, titled "DISPLAY LAYOUT AND INTERACTIVE OBJECTS FOR PATIENT MONITORING," and to U.S. Provisional Patent Application No. 63/017,151, filed Apr. 29, 2020, titled "DISPLAY LAYOUT AND INTERACTIVE OBJECTS FOR PATIENT MONITORING." All the foregoing are hereby incorporated by reference in their entireties herein. Any and all applications for which a foreign or domestic priority claim is identified in the Application Data Sheet as filed with the present application are hereby incorporated by reference under 37 CFR 1.57.

BACKGROUND

The present disclosure relates to display layouts and interactive objects for a physiological patient monitoring system.

In a hospital setting, often minor oversights can turn into fatal mistakes. Many of these oversights are due to the fact that healthcare professionals are constantly inundated with large amounts of information. It is difficult, if not impossible, to stay completely abreast of each patient's progress and procedures, and hospital charts often indiscriminately list information without indication of which pieces of information are the most critical for patient care. Thus, there is a need for more intuitive and streamlined modes of conveying patient information to healthcare professionals.

SUMMARY

For purposes of summarizing the disclosure, certain aspects, advantages and novel features are discussed herein. It is to be understood that not necessarily all such aspects, advantages, or features will be embodied in any particular embodiment of the invention and an artisan would recognize from the disclosure herein a myriad of combinations of such aspects, advantages or features.

The disclosure describes a physiological patient monitoring system with a healthcare professional-facing interface. The healthcare professional interface may communicate critical patient information to hospital staff in quick and concise, yet clear, ways. Due to the sensitive nature of patient information, the healthcare professional interface may only display by default the most critical non-confidential patient information. To access the full range of features in the system, in some configurations, the hospital staff may be required to unlock the device via entering a personal identification number ("PIN"), entering a password, scanning a Radio Frequency Identification ("RFID") chip, or any other method of automated secure access. Once unlocked, hospital staff can access all of a patient's treatment history, and much or all data may be consolidated and presented intuitively such that the care team member can quickly catch up on the patient's progress before entering the room to speak with the patient.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure.

FIG. 6A-6F are illustrative interfaces displaying a patient's lab results, according to some embodiments.

DETAILED DESCRIPTION OF THE PREFERRED EMBODIMENT

The current hospital system is riddled with opportunities for minor oversights to turn into fatal mistakes. Such opportunities arise because information is not presented in easily accessible methods that busy healthcare professionals can quickly and easily digest. Critical patient data is often buried under hundreds of pages of paperwork, and physicians often rush to skim patient charts while chatting with the patient. The presently disclosed healthcare professional interface of a physiological patient monitoring system addresses the issue of inaccessible information by consolidating the most key pieces of patient information and presenting the information in an intuitive manner. By clearly presenting critical patient information to healthcare professionals, the present system can reduce errors that can cost patients their lives.

Figure 1:
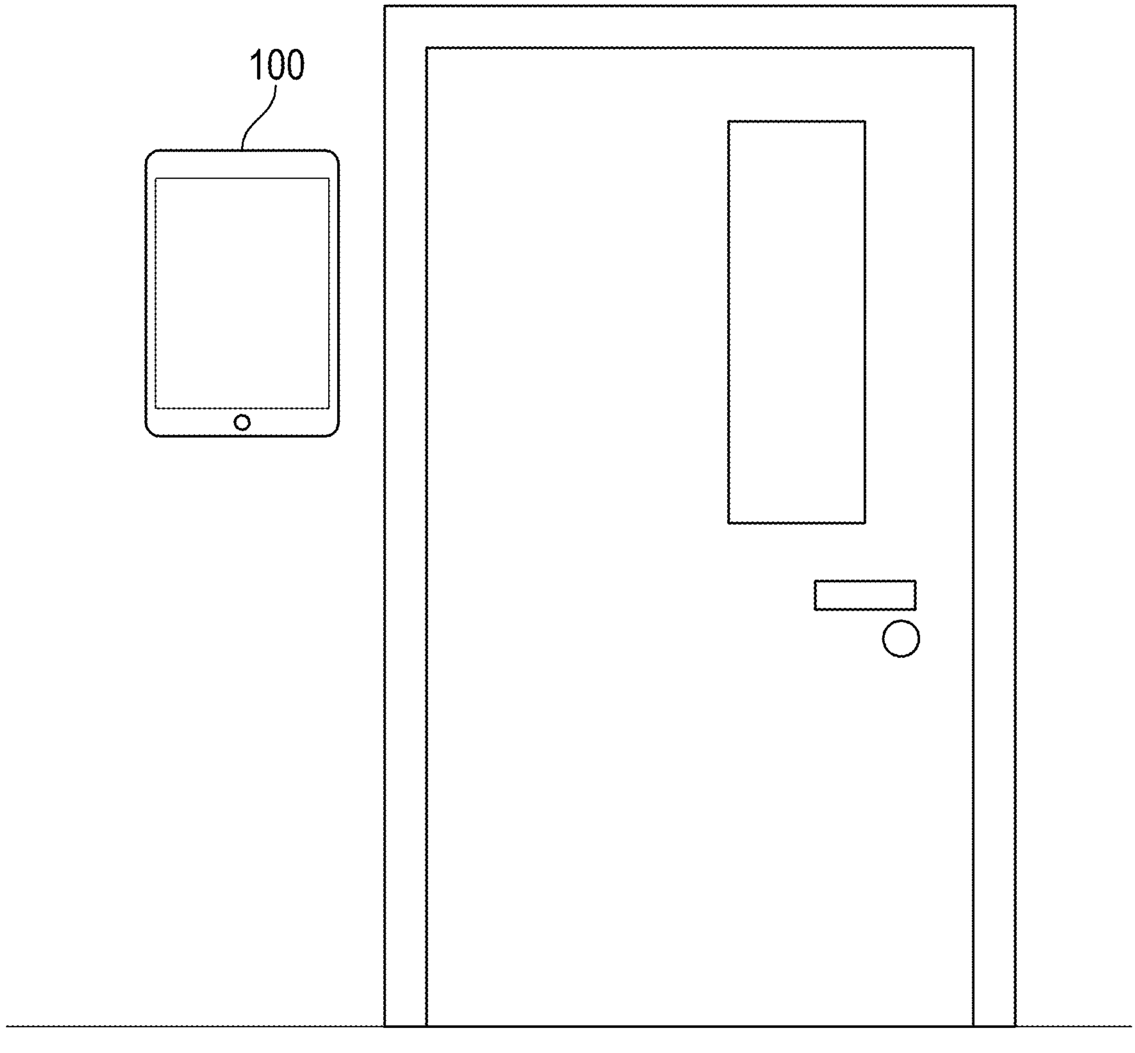
FIG. 1 depicts a portable device with a healthcare professional interface for a physiological patient monitoring system mounted outside a hospital room.

FIG. 1 depicts a portable device 100 with the healthcare professional interface of a physiological patient monitoring system mounted or otherwise placed on the wall outside a hospital room. The interface may display medical information for one or more patients occupying the hospital room. In some configurations, the portable device 100 may be in close proximity to the hospital room, though not mounted on the wall. For example, the portable device may be placed on a device-holding stand next to the door of the hospital room. The portable device may be secured in a way that allows easy removal from the surface to which it is secured. For example, the portable device 100 may be placed in a bin mounted on the wall, held in place by a hook and loop fasteners, clasped, or any other method of securing the portable device in a set position while also allowing relatively easy removal. In other configurations, the portable device 100 may be secured such that the device 100 may only be removed by authorized healthcare administrators. For example, the device 100 may be stored in a locked bin or locked onto a device stand, where the locking mechanism may be mechanically or electronically controlled. In configurations with mechanical locks, only approved healthcare providers may be allowed to have possession of the key. In configurations with electronic locks, the lock may automatically unlock when an approved provider approaches the device 100 (for example, through use of an RFID tag, Wi-Fi triangulation, or other known location techniques) or may be manually unlocked via a password, PIN, biometric identification measures, etc. In yet other configurations, the portable device may be located at a nurse station or carried by a healthcare provider. The placement of the portable device may allow physicians and other hospital staff to review critical information about a patient before entering the patient's room. The current predominant system relies on physical printouts of such information, and key information can be lost in the middle of hundreds of pages of paperwork. Having the most critical information posted outside of a patient's room can reduce the chances of medical staff overlooking critical information.

To protect patient privacy, the device 100 may be configured to dim or completely darken the screen in certain situations. In some configurations, the portable device may have its screen completely darkened when the device is not in use. The screen display may be activated by touching the screen or a button on the device 100. In other configurations, the portable device's screen display may automatically turn on when a healthcare provider approaches the patient's room. This can be done by an RFID tag, Wi-Fi triangulation, or other known location techniques. In some configurations, the device screen may dim after a pre-determined period of time without detected use or motion, such that passersby may not see private patient data if a physician leaves the device unattended. In other configurations, the device may automatically lock after a pre-determined period of time without detected use or motion. In yet other configurations, the device 100 may automatically lock upon being returned to its assigned mounting location. In yet other configurations, the device 100 may be manually locked by the healthcare provider after using it. In some configurations, the device 100 may include an alarm system to alert hospital staff that the device 100 was not replaced to its assigned area. The alarm system may be triggered after a pre-determined period of time away from its assigned area and without detected used. The alarm system may generate an audible noise from the device 100, or it may ping other electronic devices associated with hospital staff members.

Figure 2A:
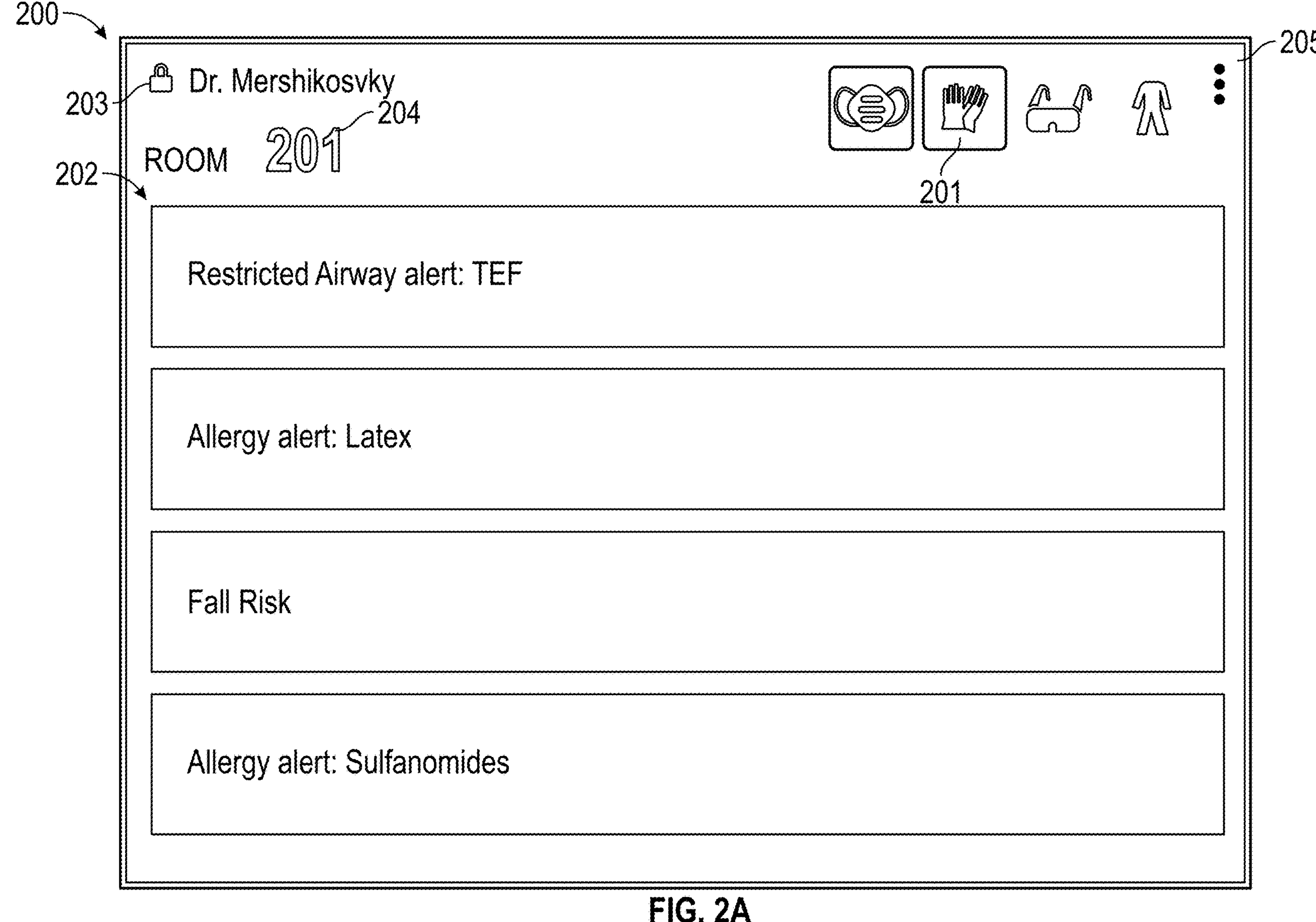
FIGS. 2A-2M are illustrative interfaces for a default screen showing critical, non-confidential patient information, according to some embodiments.
Figure 2B:
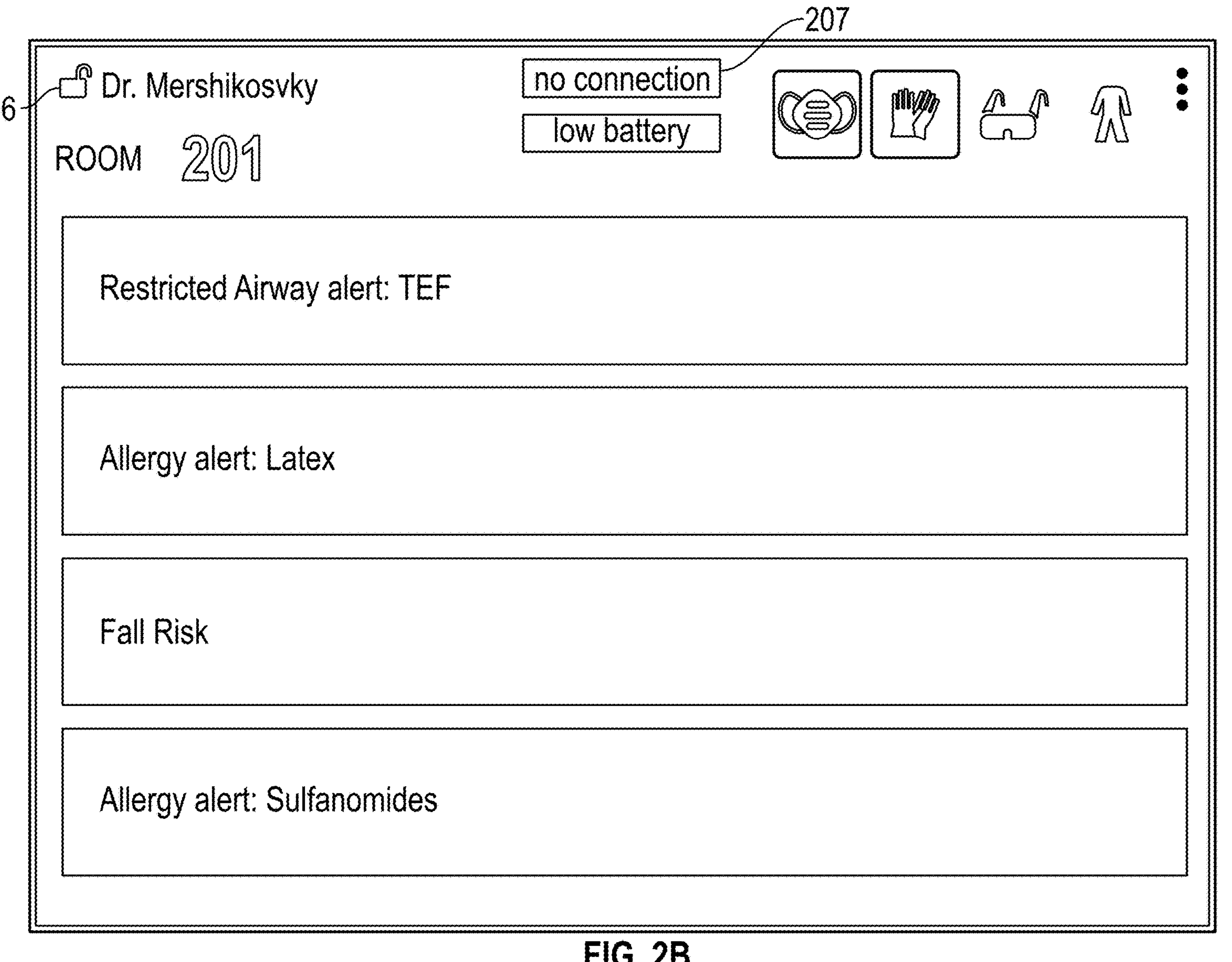
Figure 2C:
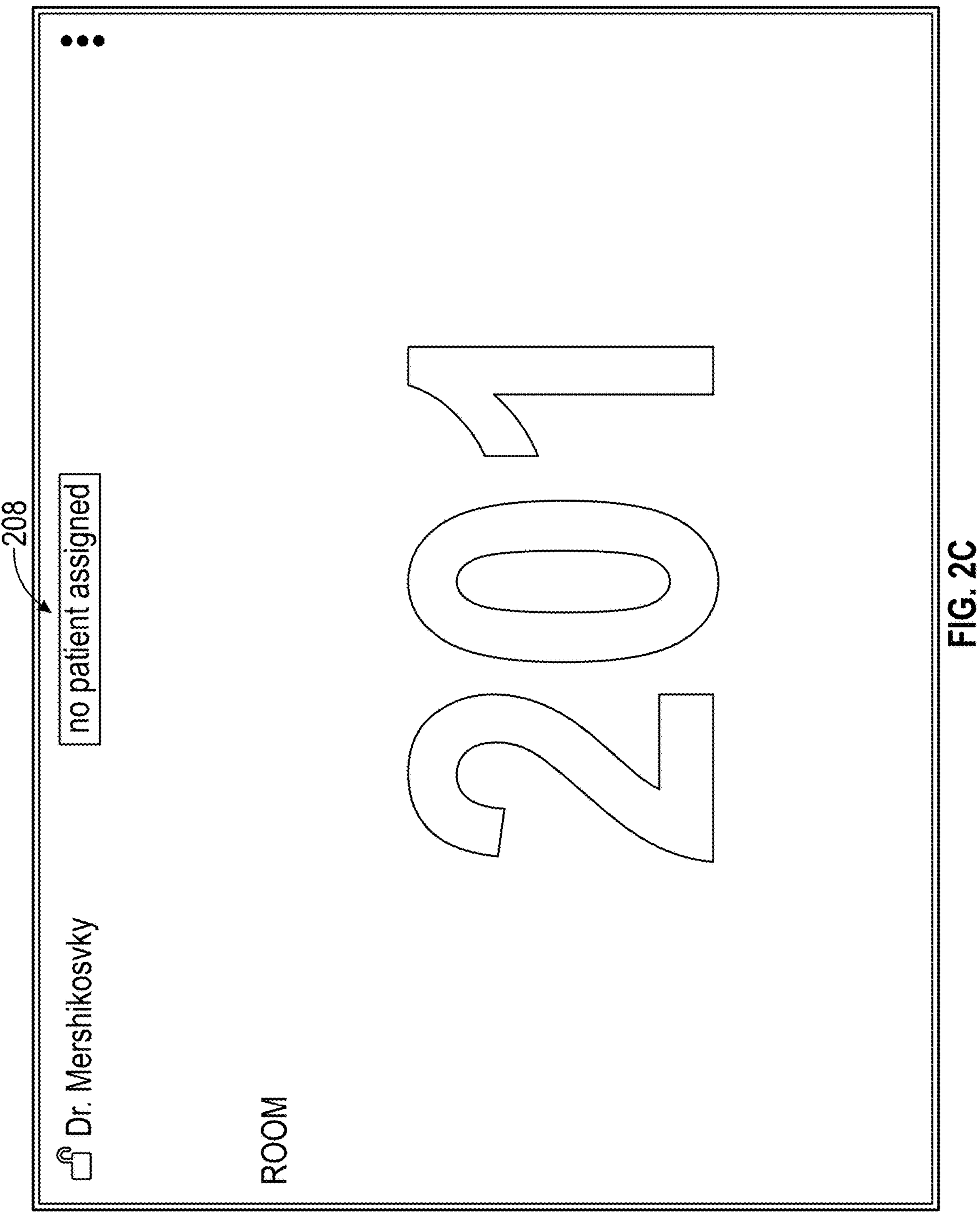

The physiological patient monitoring system may be connected to patient monitoring equipment and a hospital data network. The healthcare professional interface may thus be updated with live measurements, safety precautions, and lab results. The healthcare professional interface may also connect to other systems integrated in the hospital. For example, hospital rooms may be equipped with a ceiling-mounted display configured to display different types of health parameters, emergency notifications, and safety precaution measures. The healthcare professional interface may be in communication with the ceiling-mounted display such that the display shows certain data from the interface. In some configurations, the display may show the default screen 200 of the healthcare professional interface (FIGS. 2A-2C). In other configurations, the display may show any screen from the healthcare professional interface. In yet other configurations, the display may only receive data from the healthcare professional interface, then generate a different illustration by applying different color schemes for different types of health parameters or health parameter values. For example, the color red may be used to indicate health parameter values that are out of a predetermined range, while the color green may be used to indicate health parameter values that are within the predetermined range. In another example, different physiological parameters can be assigned different colors. For example, blood pressure readings may be in green while temperatures readings may be in red. The display can also use different color schemes for notifications indicating different patient conditions. For example, the display may generate and display notifications and/or parameter readings in red during emergency situations. On the other hand, the display may generate and display notifications and/or parameter readings in green or no color in normal situations. The display may always be on, or the display may only turn on when the associated portable device 100 turns on. Updates to both the healthcare professional interface and ceiling-mounted display may occur continuously, automatically, only when new data is manually entered, or any combination of these methods.

FIGS. 2A-C illustrate one example of a default screen 200 for a hospital staff interface for portable devices located outside of a hospital room. As shown in FIG. 2A, the default screen 200 may list safety precautions 201 and critical patient information 202. The safety precautions 201 may warn clinicians to use certain personal protective equipment, including, but not limited to, gloves, eyewear, and masks. Critical patient information 202 may include, but is not limited to, severe allergies, other medical conditions, and other potential risks of harm. To protect sensitive patient information, only non-HIPAA (Health Insurance Portability and Accountability Act) protected information may be displayed on the default screen 200, and the interface may remain locked when the device is not in use. The interface can be unlocked via entering a personal identification number ("PIN"), entering a password, scanning a Radio Frequency Identification ("RFID") chip, or any other method of automated secure access. Once unlocked, the device can display further details in the patient's medical file. The default screen 200 may include a lock status icon 203 so users can easily recognize if an interface is locked or unlocked. The default screen 200 may identify the hospital room 204 for which patient data is being displayed. The default screen 200 may also include a settings menu 205, described in greater detail below in relation to FIGS. 23A-P, where the clinician can select which information to display and customize the interface. FIG. 2B shows the default screen 200 after a clinician has logged in. The screen may show an updated lock status icon 206, which may indicate that the interface is unlocked and which clinician is logged in. The default screen 200 may further display device warnings 207, such as, but not limited to, low battery warnings or unstable connection warnings. FIG. 2C shows an illustrative default screen 200 when there is no patient assigned to the room and no patient data to display. In such a scenario, the default screen 200 may only display the hospital room 204 with which the device 100 is associated. The default screen 200 may further display a no-assignment notification 208. In some configurations, the device warnings 207 may be displayed on the default screen 200 at all times: before and after clinician login and regardless of patient assignment. In such configurations, the device warnings 207 would appear concurrently with the no-assignment notification 208.

Figure 2D:
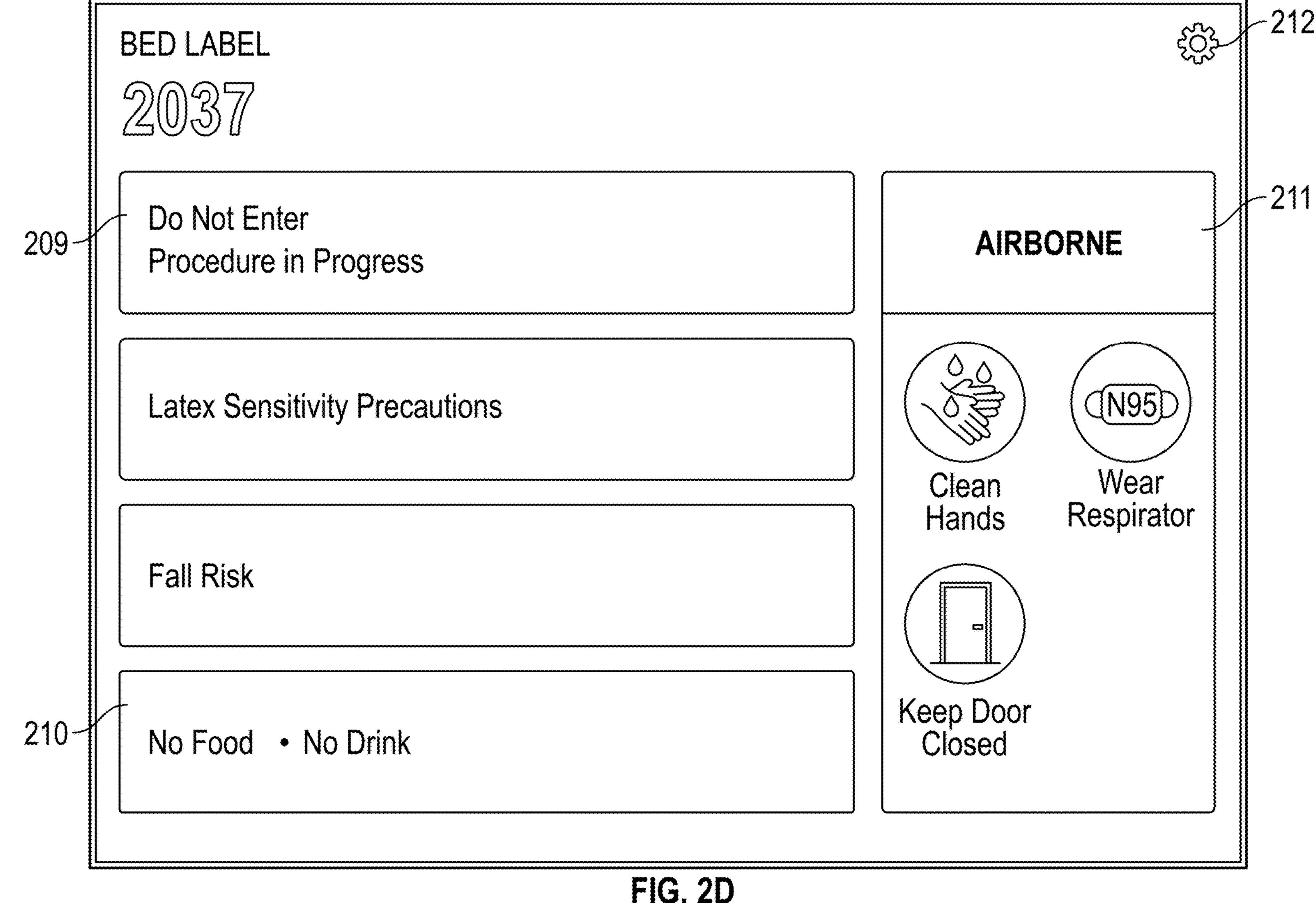

FIG. 2D illustrates another configuration of a default screen 200 for a hospital staff interface. As depicted, critical patient information 202 may further include procedure alerts 209 to prevent disturbance of the procedure. Critical patient information 202 may also include food and drink warnings 210. Food and drink warnings 210 may span beyond food allergies and may be necessary for patients preparing for procedures that require fasting beforehand. In this configuration, the default screen 200 may display the type of pathogen risk 211 present in the hospital room. Safety precautions 201 associated with prevention of the displayed type of pathogen risk 211 may then be listed. Critical patient information 202 may also include warnings for patients that need to be isolated (for example, highly contagious patients or patients who may be a safety risk to others). FIG. 2D also shows an alternative settings menu icon 212. The critical patient information 202 may be color-coded to reflect various parameters. For example, procedure alerts may be presented in red print or in a red color block as they act to prevent immediate patient harm and should be noticeable.

Figure 2E:
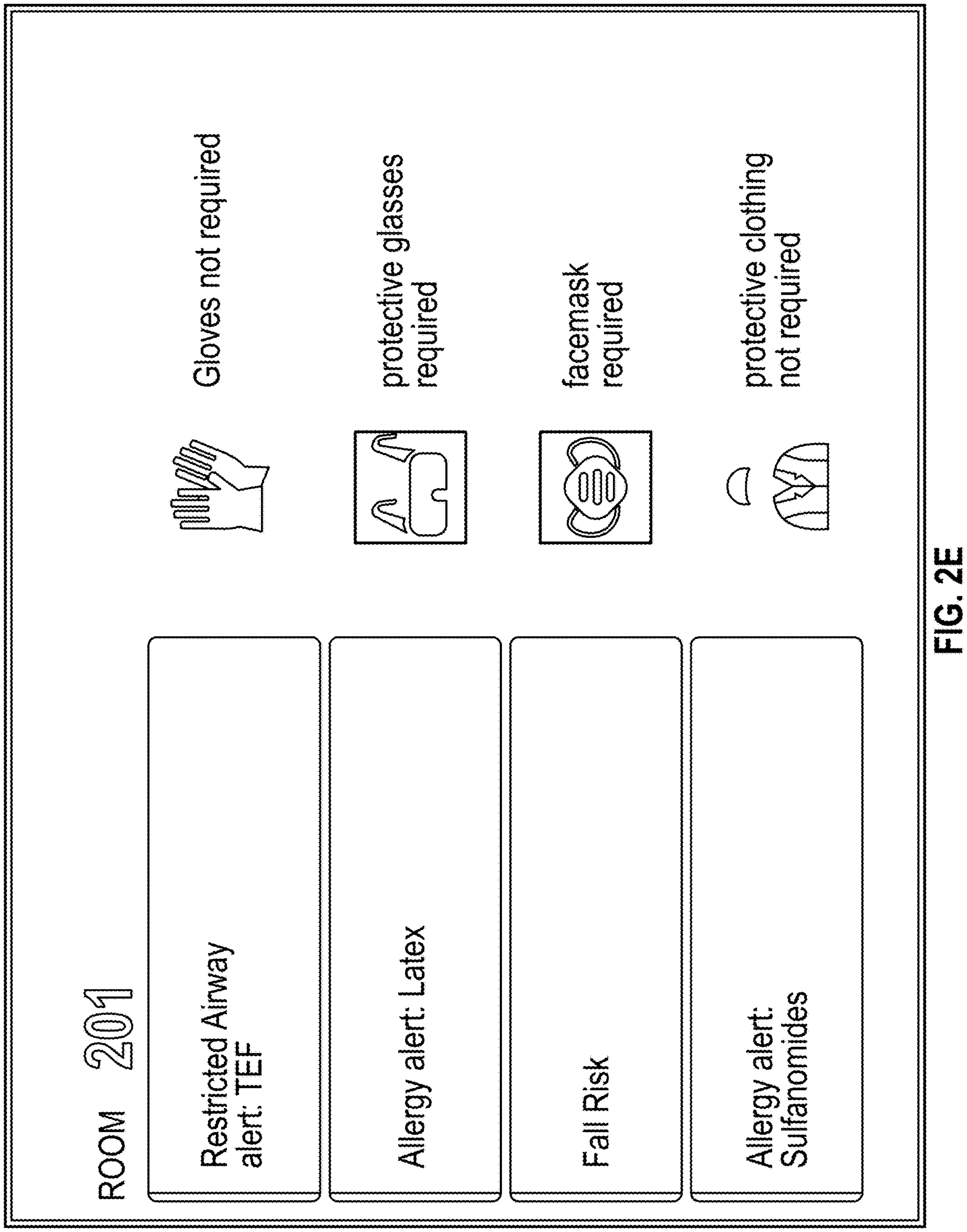
Figure 2F:
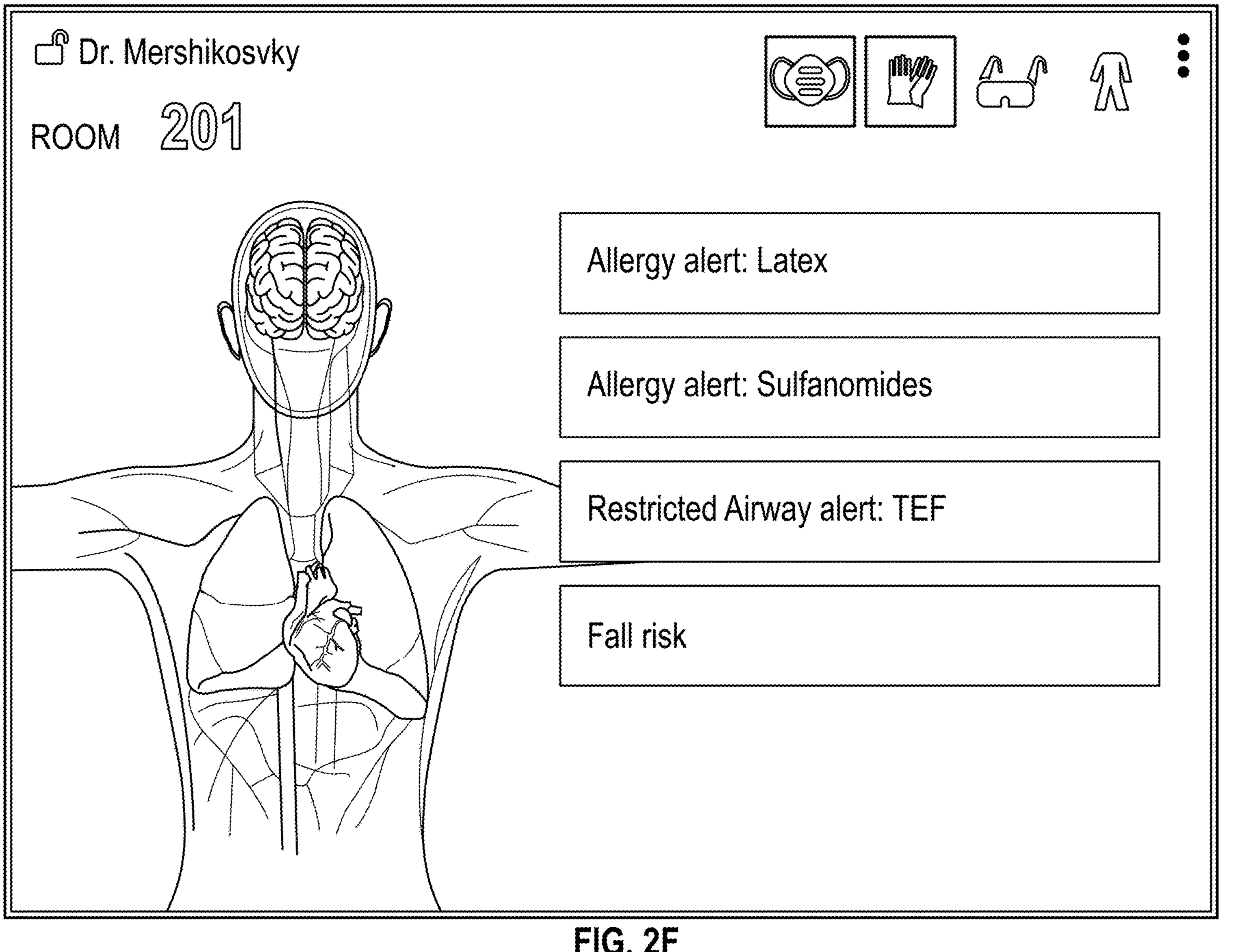
Figure 2G:
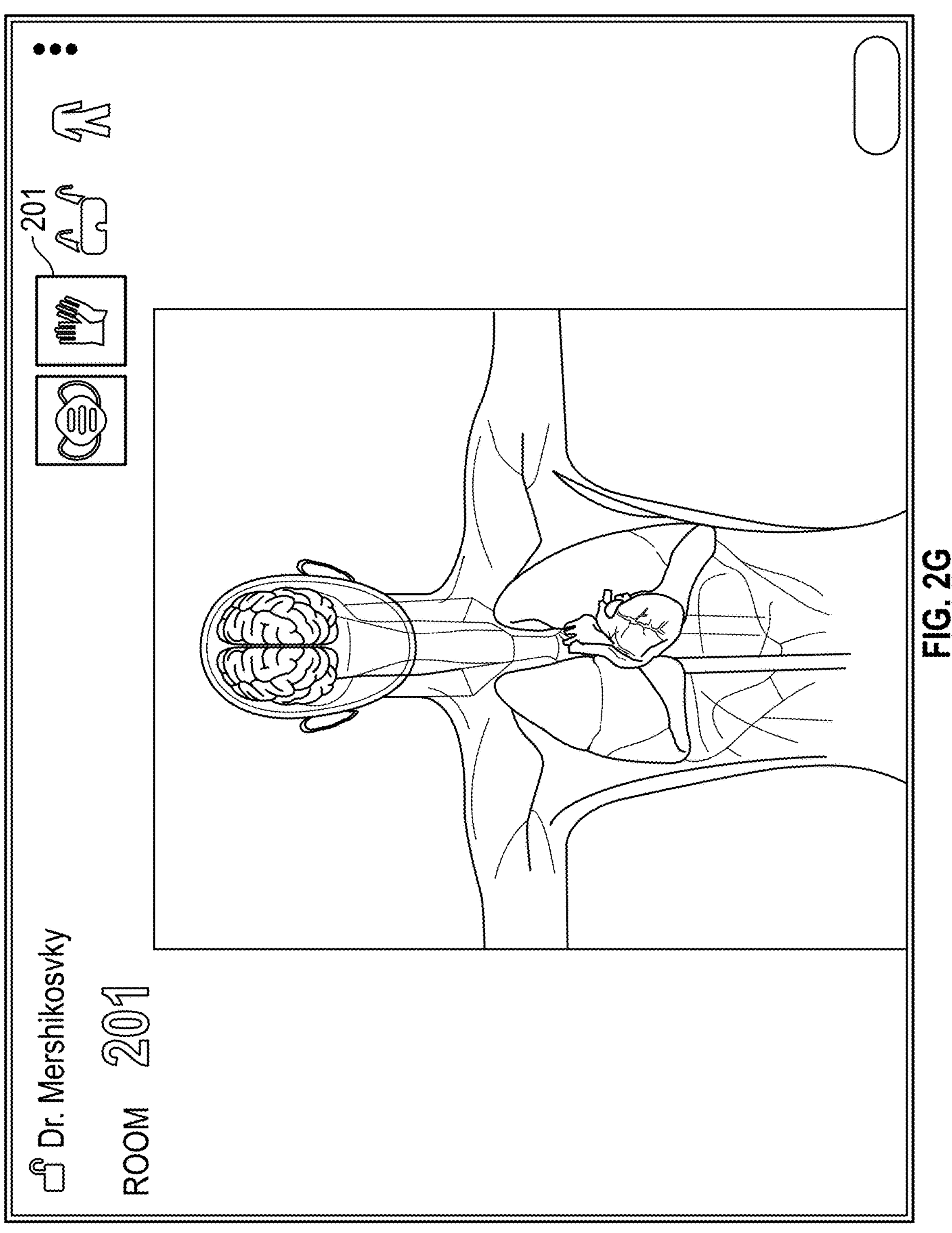

FIGS. 2E-G are other examples of default screens 200. FIGS. 2E and 2F show examples of default screens 200 when the device is associated with a patient. FIG. 2G shows an example of a default screen 200 when there is no patient in the assigned hospital room 204. Safety precautions 201 may be listed as necessary when there are no patients in the room. For example, the room may be left vacant for disinfecting purposes prior to admitting the next patient. In such situations, anyone entering the room may still require safety equipment and other precautionary preparation. In other configurations, the default screen 200 may not show safety precautions 201 when there are no patients in the hospital room 204.

Figure 2H:
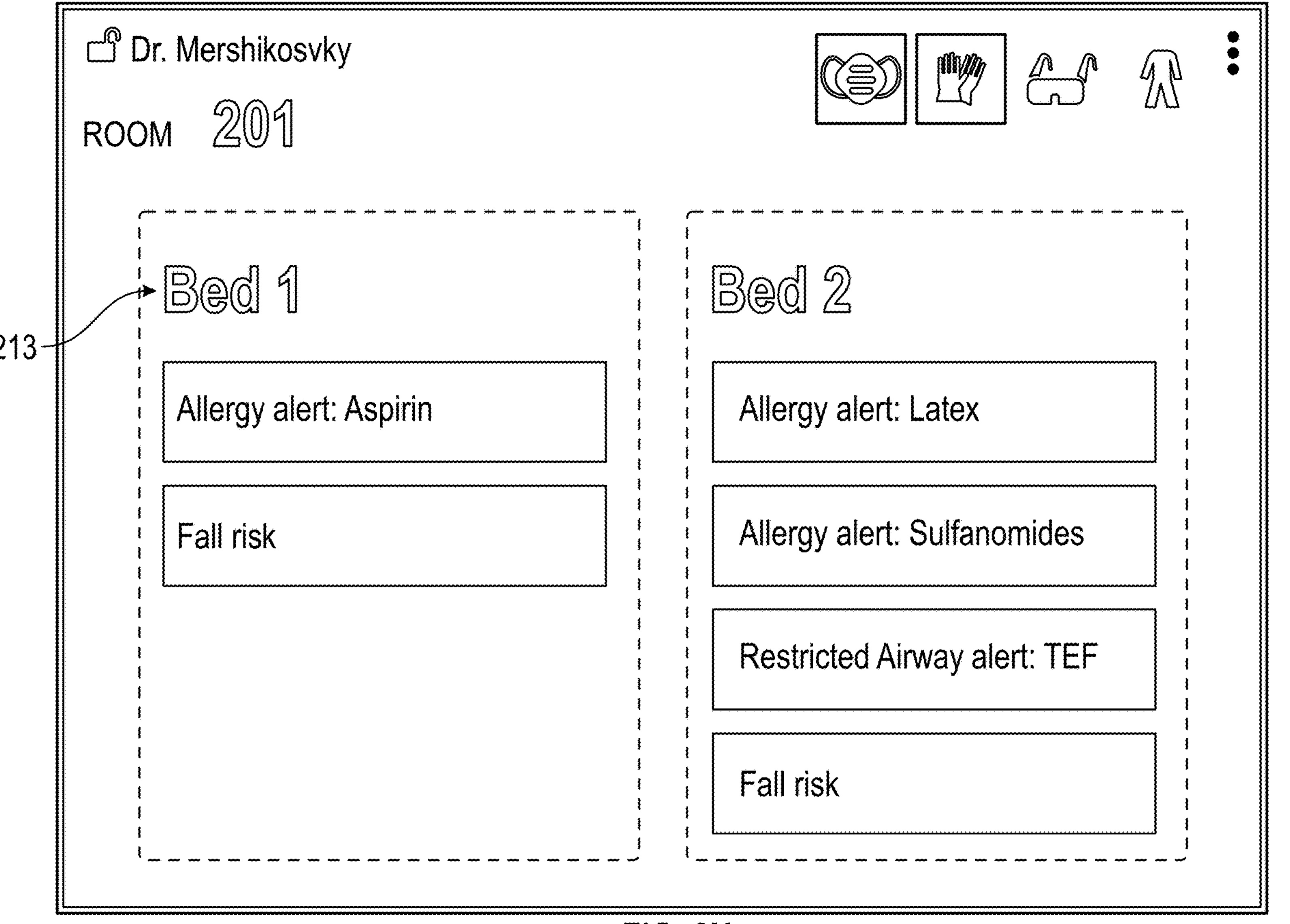
Figure 2I:
Figure 2J:
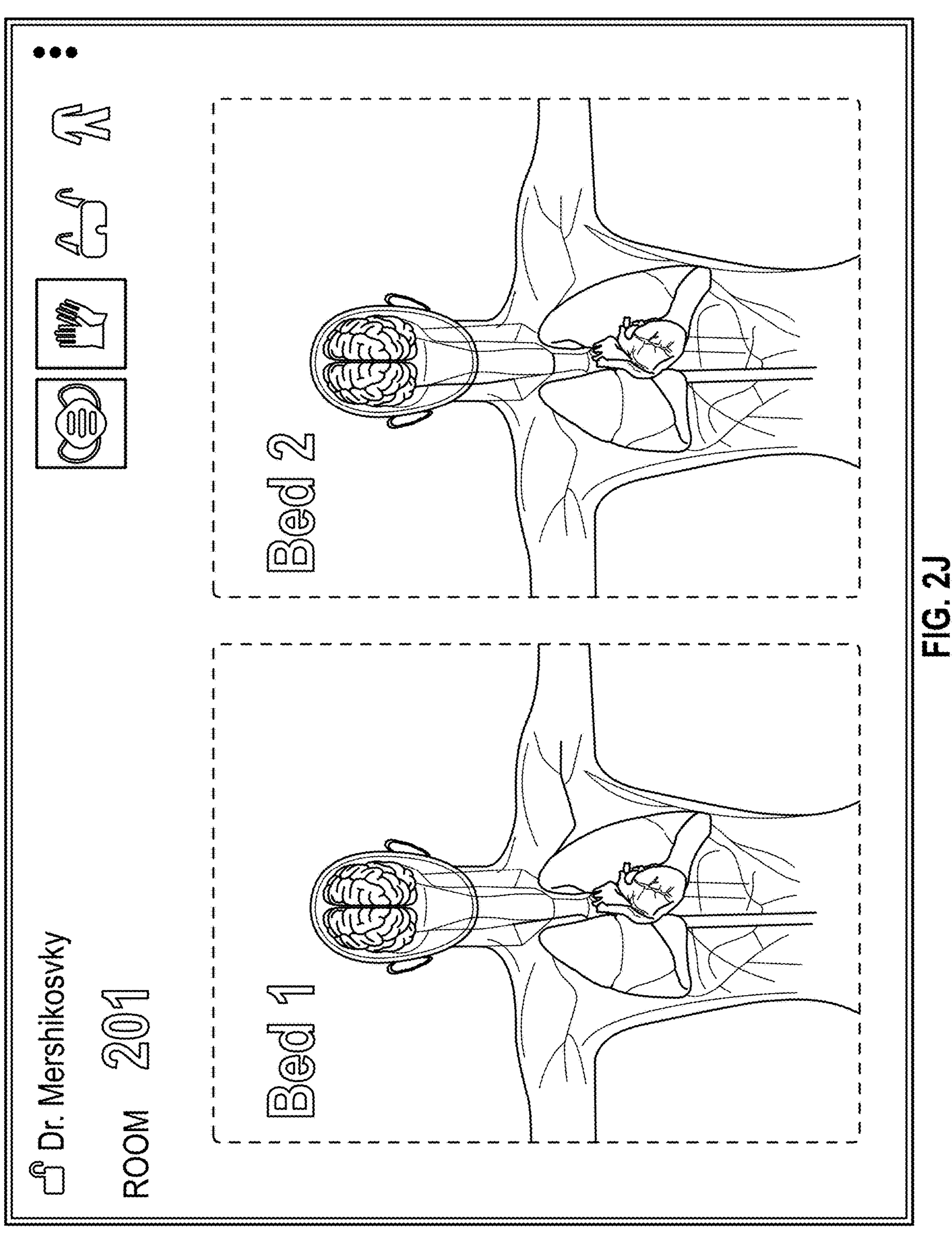
Figure 2K:
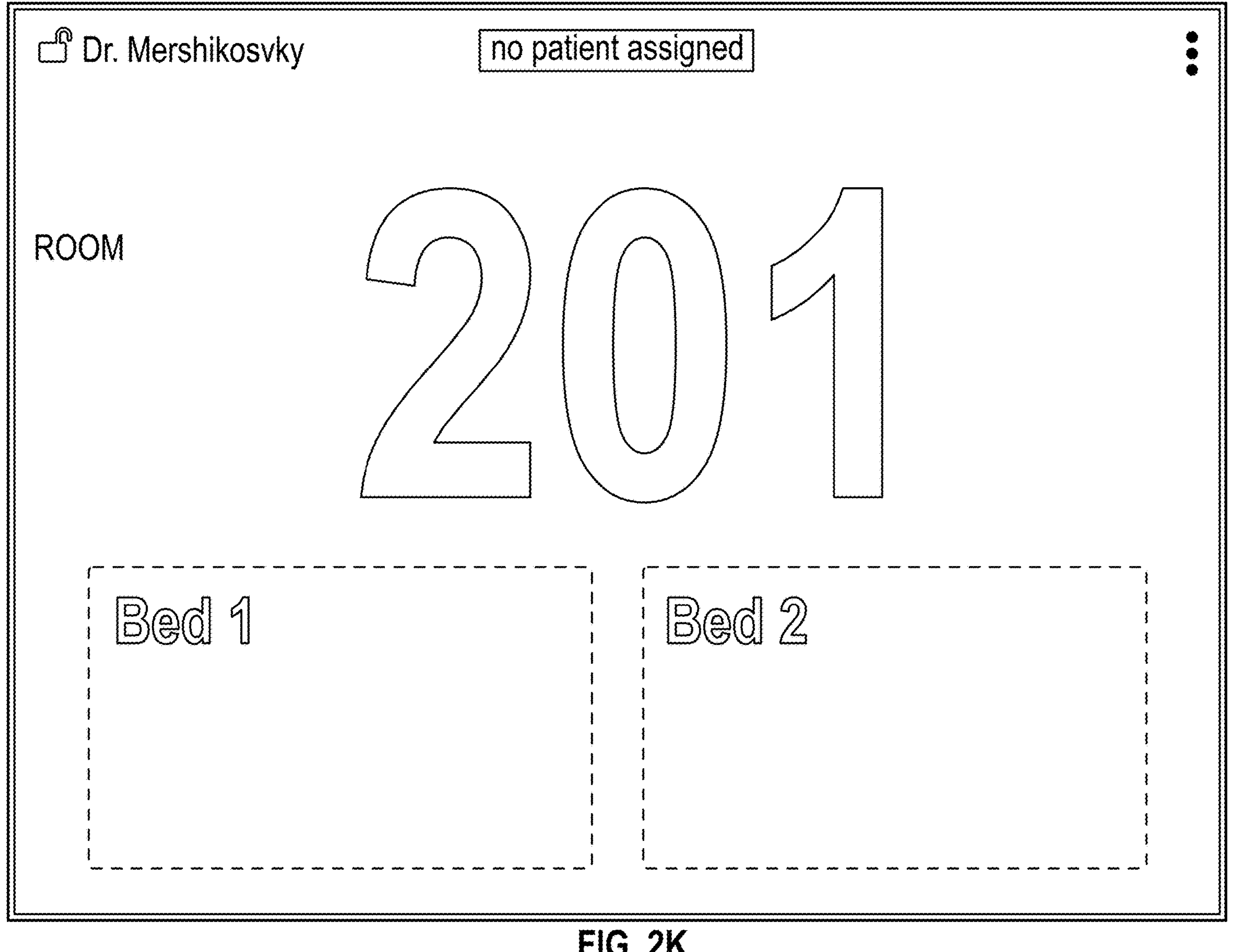

FIGS. 2H-K illustrate another example default screen 200 in which there are two beds in the hospital room associated with the interface. FIGS. 2H and 2I show that the double-bed configurations may display all the same features as a single-bed default screen. The double-bed configurations may further display a bed number 213 for each bed in the room. Each patient's critical patient information 202 may be listed in association with the patient's bed number 213. FIGS. 2J and 2K show double-bed screens when no patients are assigned to the hospital room 204. The double-bed configurations without patient assignments may display all the same features as a single-bed default screen that has no patient assignment.

Figure 2L:
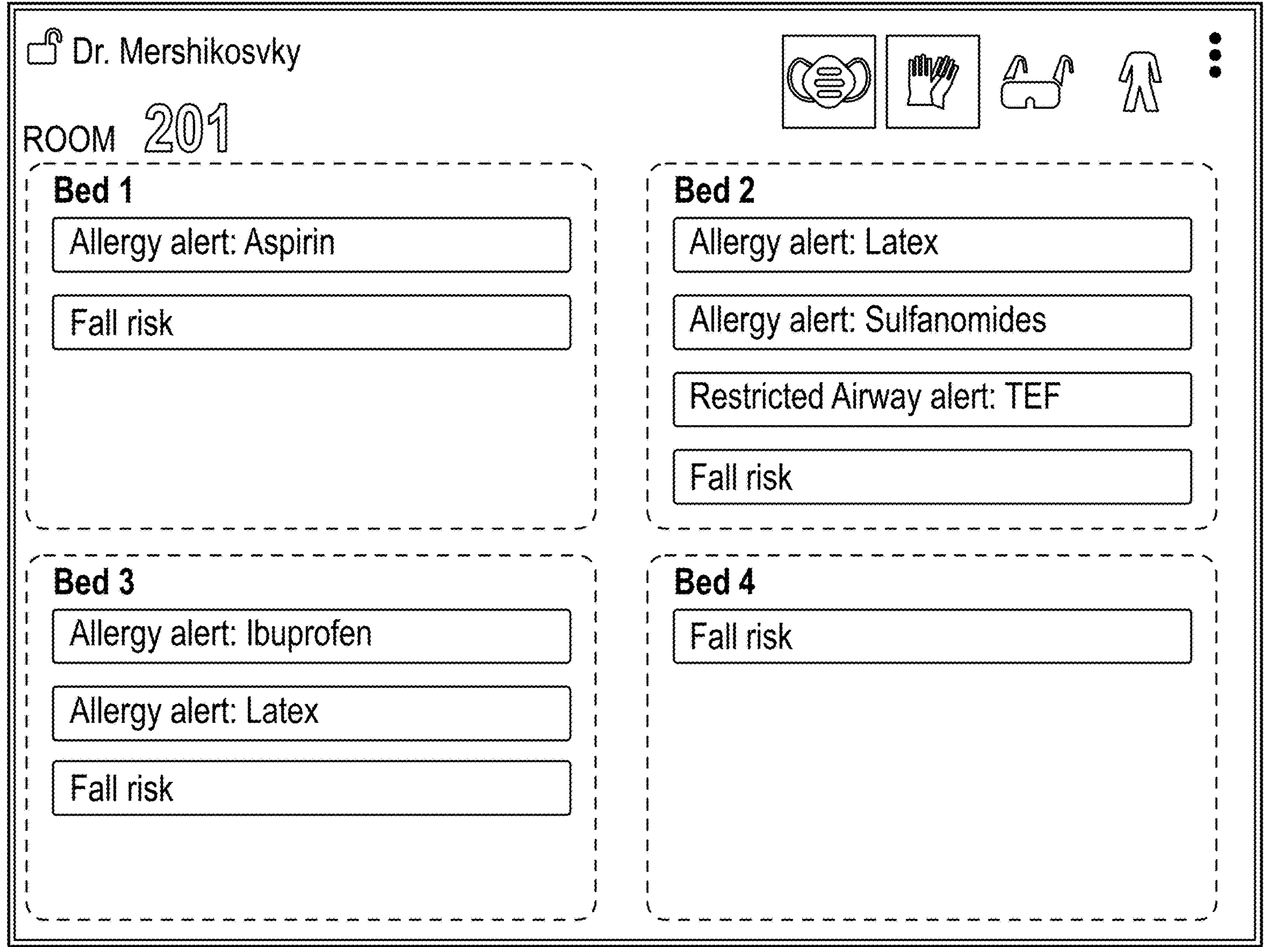
Figure 2M:
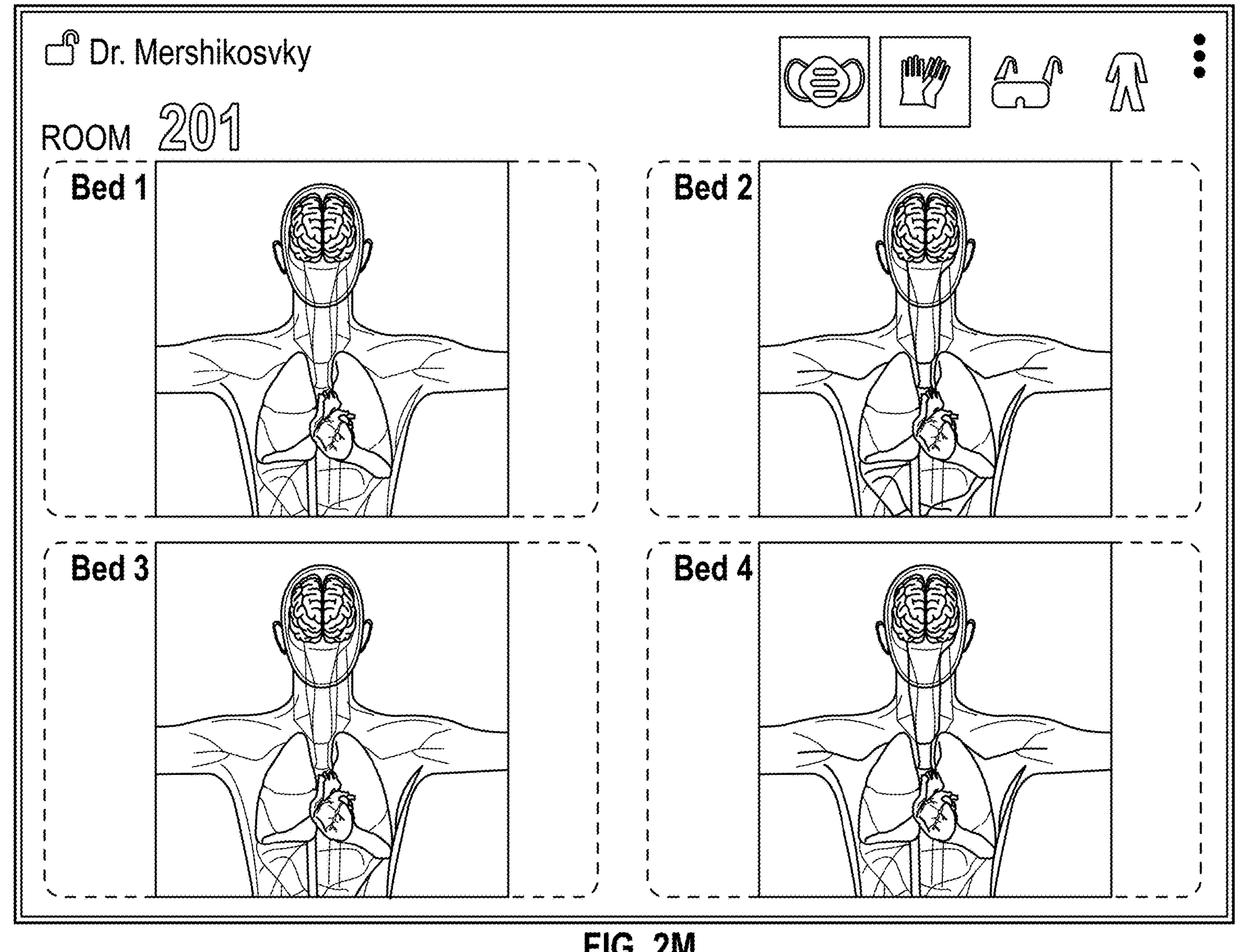

FIGS. 2L and 2M illustrate another configuration of a default screen 200 in which there are four beds in the hospital room associated with the interface. FIG. 2L shows that the quadruple-bed configurations may display all the same features as a one-bed default screen. Each patient's critical patient information 202 may be listed in association with the patient's bed number 213. FIG. 2M shows quadruple-bed screens when no patients are assigned to the room. The quadruple-bed configurations without patient assignments may display all the same features as a single-bed default screen that has no patient assignment. Accordingly, the same features are displayed for each individual patient, regardless of the number of beds in the hospital room to which the device is paired.

With reference to FIGS. 2A-M, it should be noted that the safety precautions 201 may be selected manually and/or automatically generated. In some configurations, healthcare professionals may select the default screen safety precautions 201 via one or more settings pages, such as those illustrated in FIGS. 9A-P. In some configurations, the safety precautions 201 may be automatically generated by the physiological patient monitoring system, based at least partly on the patient's data. In some configurations the safety precautions 201 may by a combination of manually selected items and automatically generated items. For example, the physiological patient monitoring system may parse the patient's records for listed allergies to automatically display an allergy alert for the items, while the recommended safety equipment list may be selected by a healthcare professional. In some configurations, automatically generated safety precaution items may be manually overridden by healthcare professionals, via one or more settings pages, such as those illustrated in FIGS. 9A-P.

Figure 2N:
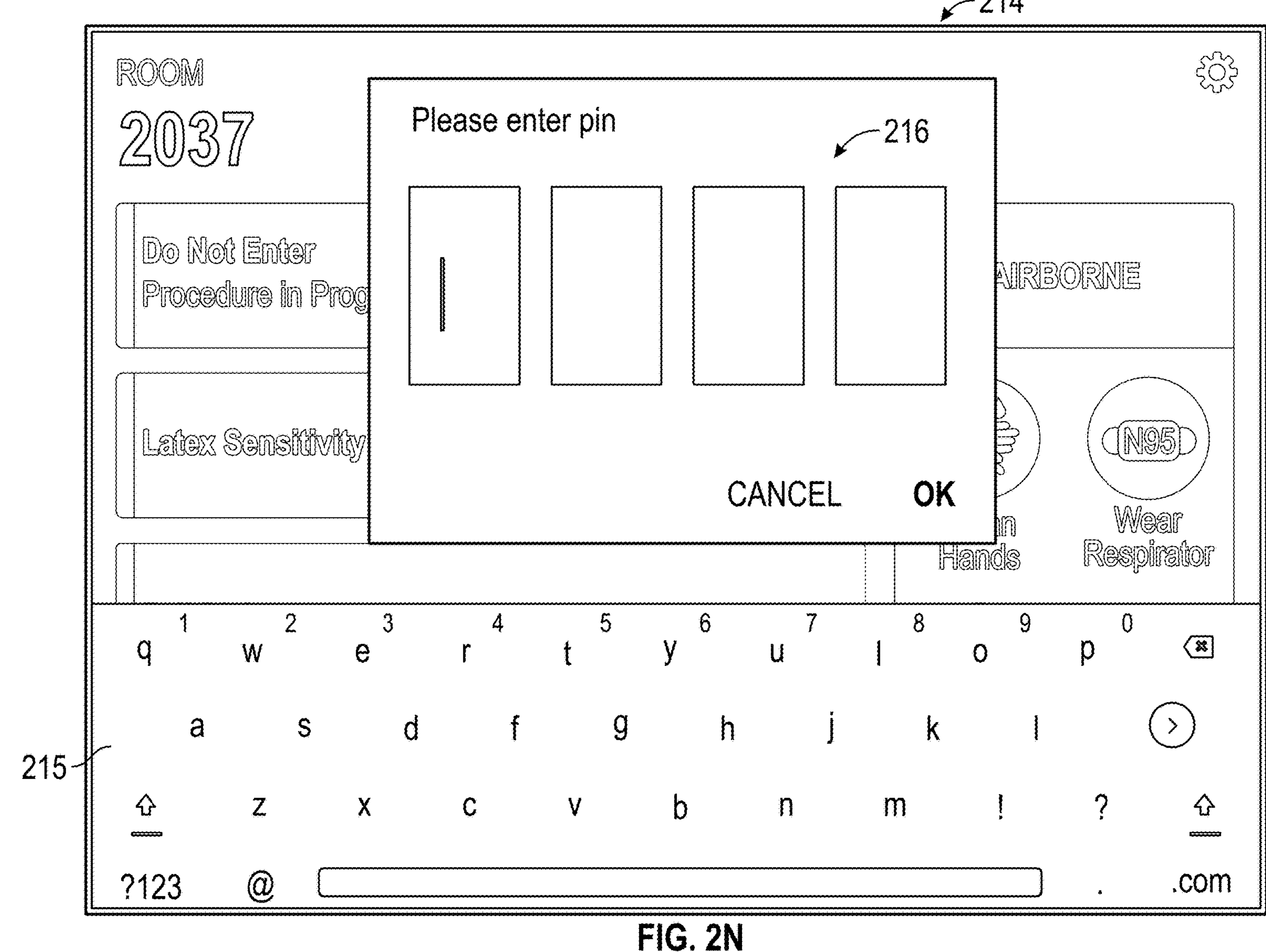
FIG. 2N is an illustrative interface for a passcode input screen from which healthcare providers may access the digital patient file, according to some embodiments.

FIG. 2N is an illustrative unlock screen 214. The unlock screen 214 may accept a PIN input to unlock the patient file. A virtual keyboard 215 may appear on the lock screen such that the user can enter a passcode. The unlock screen 214 may include a passcode display area 216 such that the user can see the inputted values. In some configurations, the passcode display area 216 may censor the values so that the passcode cannot be accidentally seen by un-intended audiences. In such configurations, the unlock screen 214 may provide an option to reveal the inputted values. It should be understood that the depicted passcode display area 216 is merely illustrative and that the passcode may be comprised of any symbols, characters, or digits and may be any length. In other configurations, the unlock screen 214 may require entering a password, scanning an RFID chip, or any other method of automated secure access. In some configurations that use card-scanning methods of secure access, the unlock screen 214 may only contain instructions to scan the card and may not contain a virtual keyboard 215 or a passcode display area 216. In other configurations that accept card scans, the unlock screen 214 may still have a passcode display area 216, but the passcode values may automatically fill once the card scans. In yet other embodiments, the unlock screen 214 may accept either manually entered passcodes or automatically-filled card scan passcodes, and may have a virtual keyboard 215 and a passcode display area 216 to support both features. Once unlocked, the staff member can navigate the application through a control panel 305, described in further detail in relation to FIG. 3A.

FIGS. 3A-E show illustrative examples of a Patient Dashboard 300, which may only be accessed after the application is unlocked. The Patient Dashboard 300 may act as a default screen when the application is unlocked. In some configurations, the Patient Dashboard 300 may not be the default screen after the application is unlocked. In such cases, the Patient Dashboard 300 may be accessed via the control panel 305.

Figure 3A:
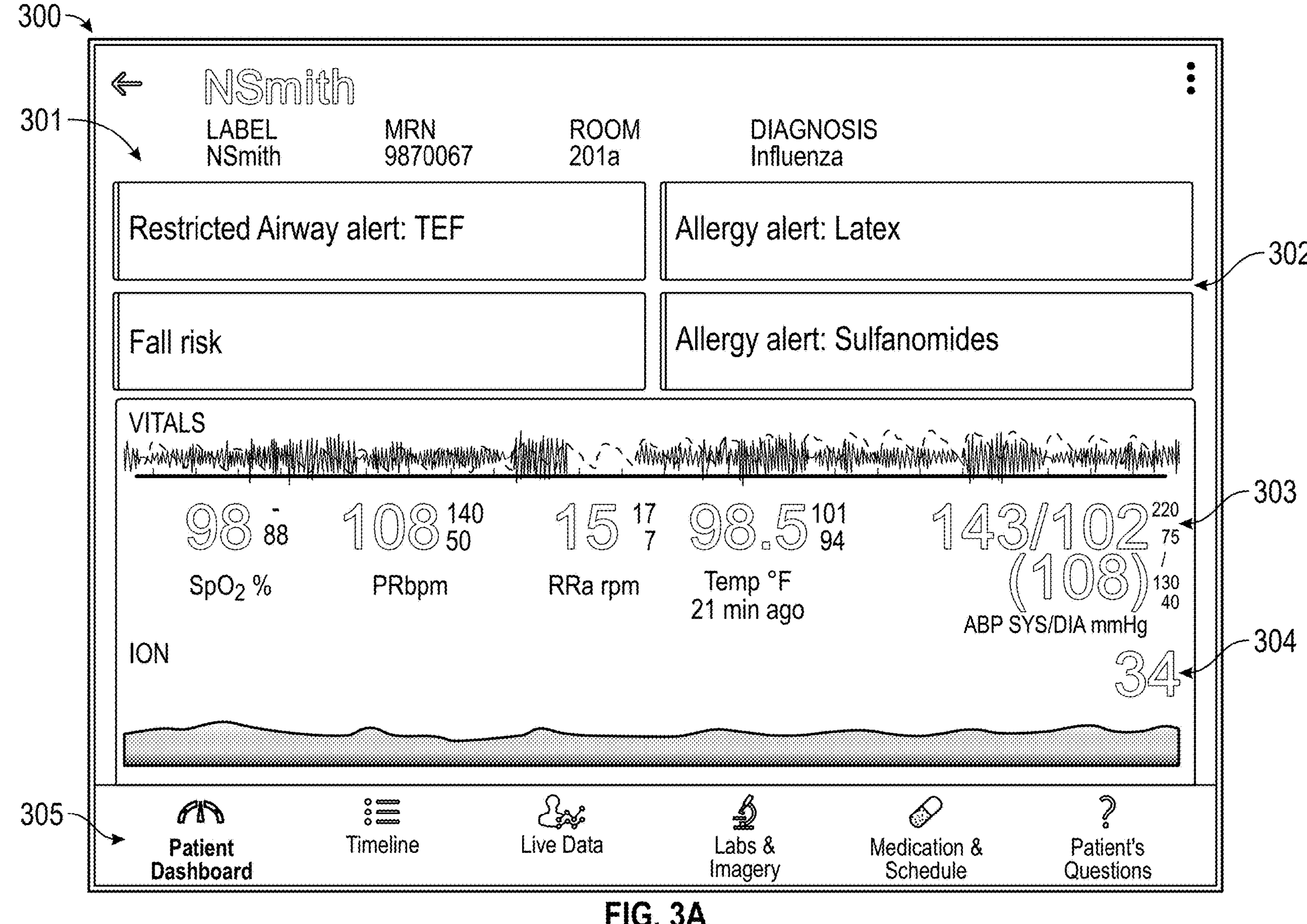
FIGS. 3A-3F are illustrative interfaces showing patient physiologic measurements, according to some embodiments.
Figure 3B:
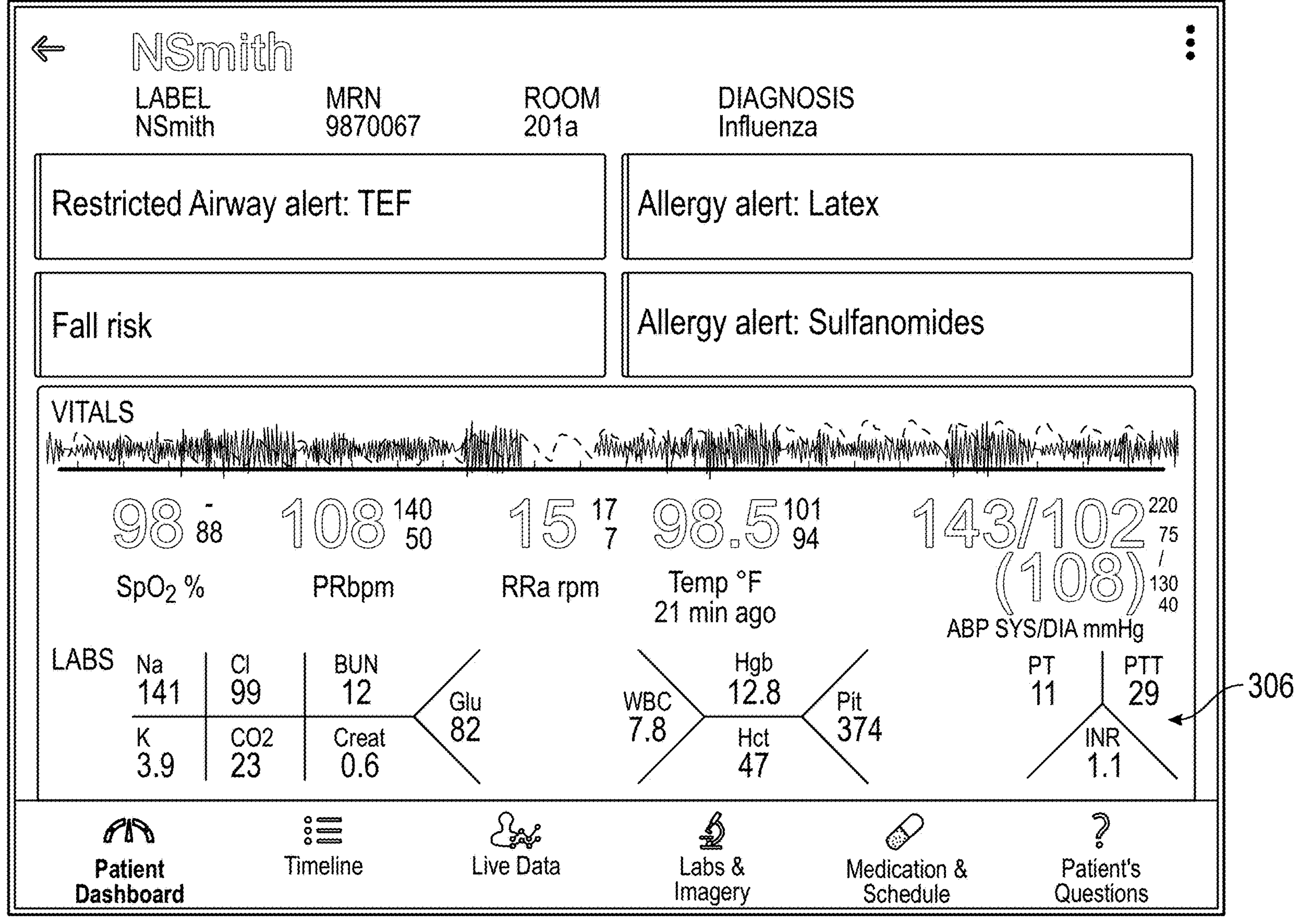
Figure 3C:
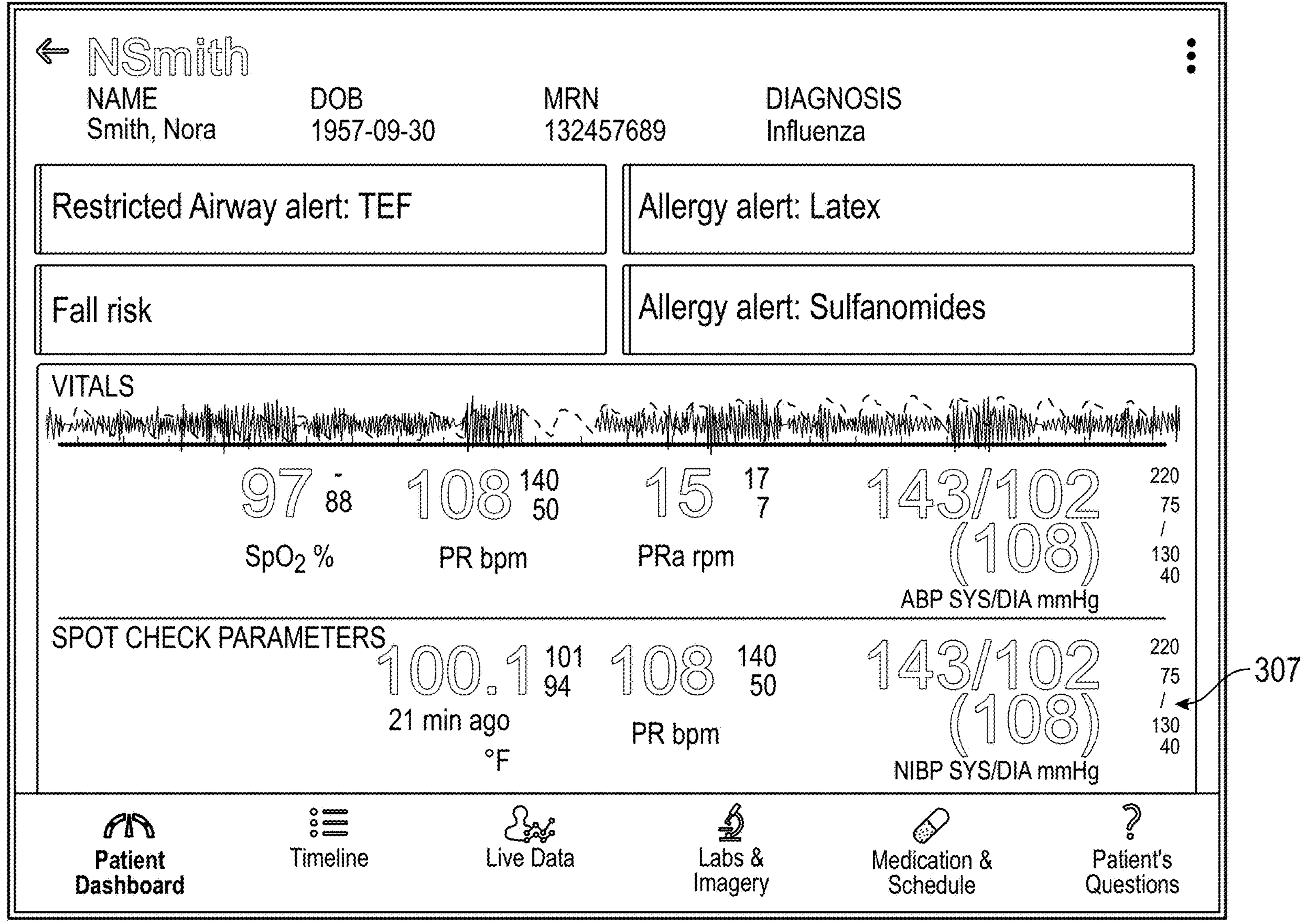
Figure 3D:
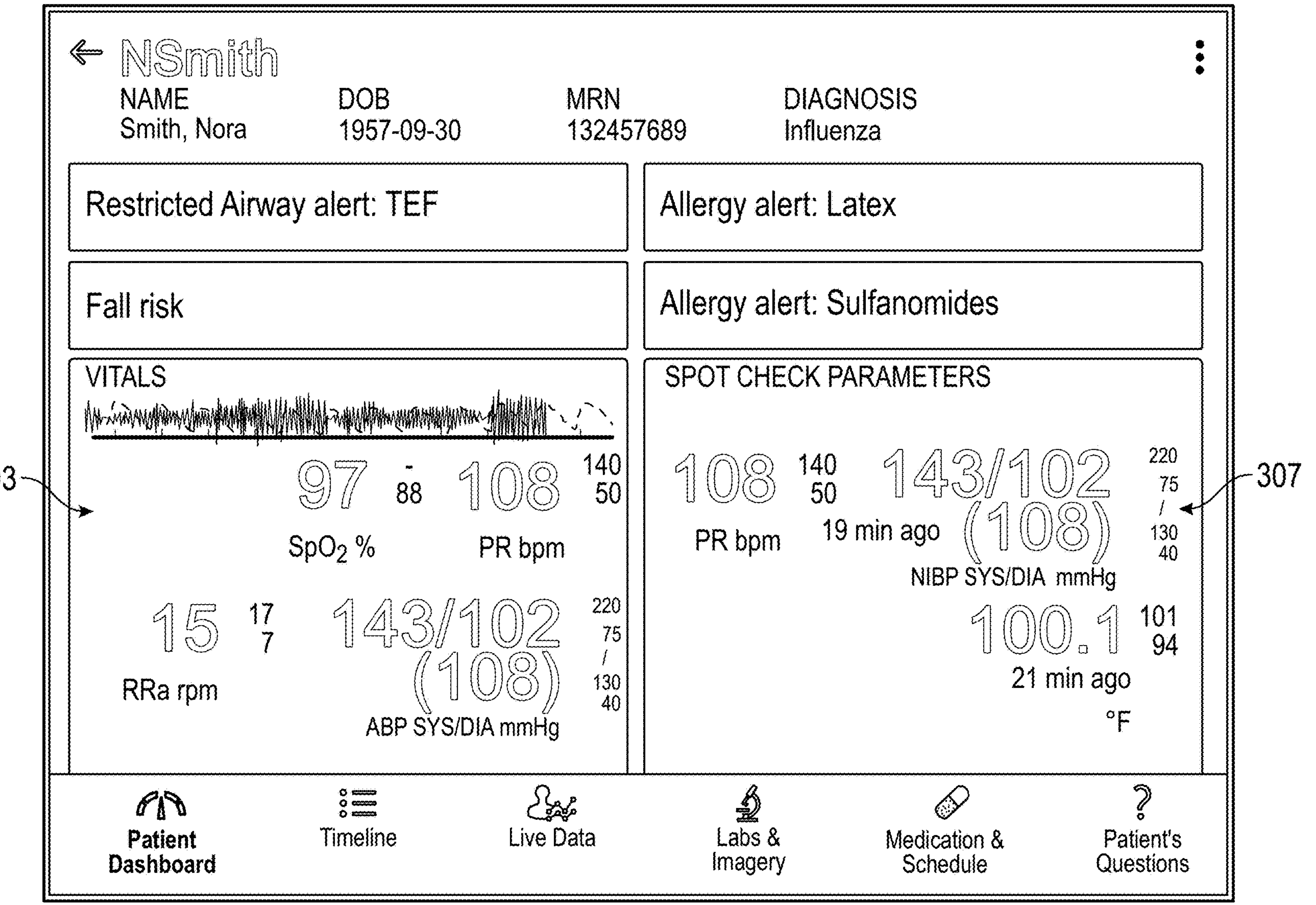
Figure 3E:
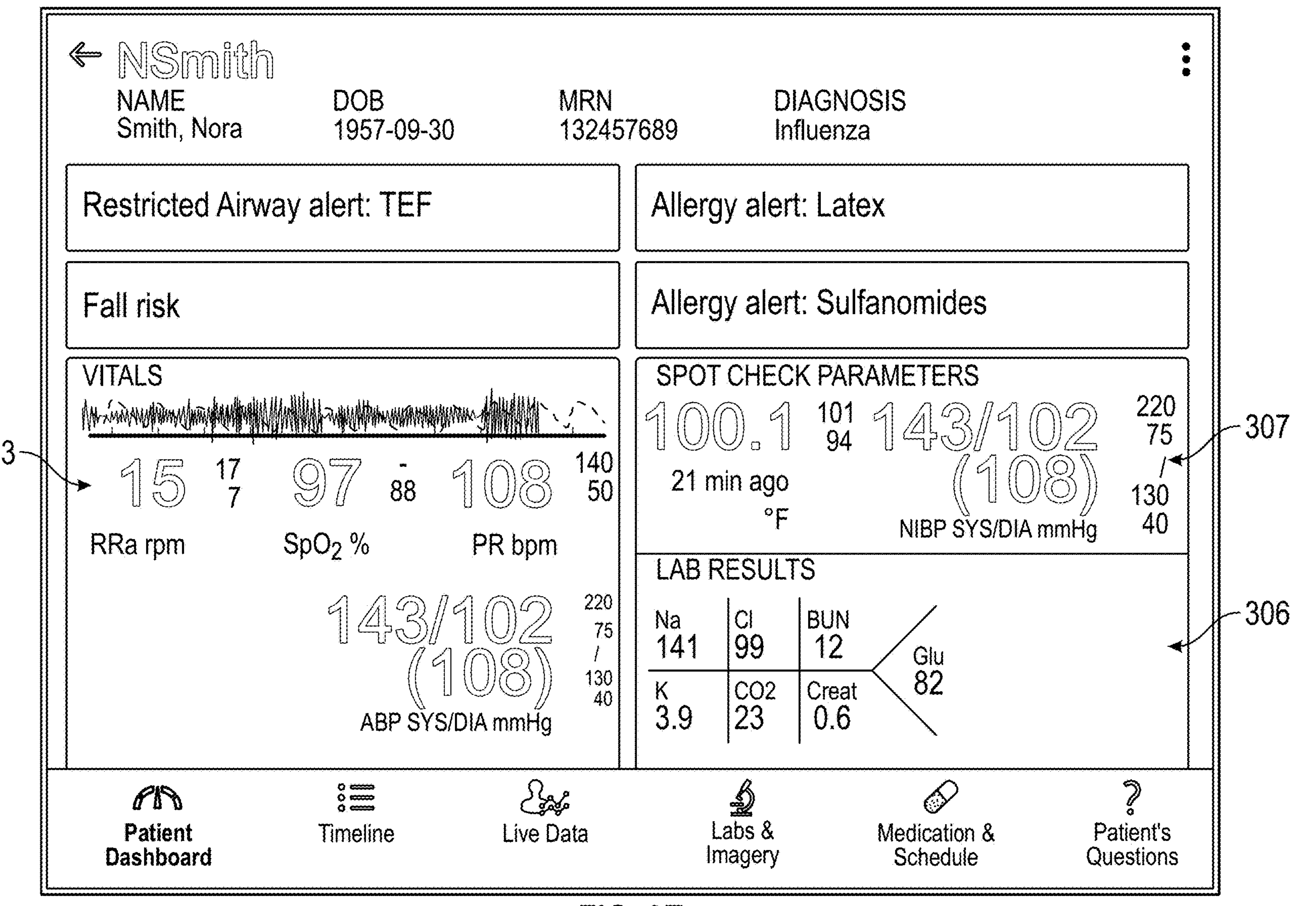

According to FIG. 3A, the Patient Dashboard 300 may list basic patient information 301, the critical information 302 from the lock screen, the patient's vitals 303, the patient's health score 304, and a control panel 305. The health score 304 may be a holistic measurement of the patient's health status. The health score 304 calculation may be based on any number of factors, including, but not limited to pulse rate, oxygenation saturation, perfusion index, or any other factors as selected by the healthcare staff. Basic patient information 301 may include, but is not limited to, patient name, age, medical record number, room and bed number, diagnosis, and other such information which a healthcare provider may need to initial interaction with the patient. FIG. 3B illustrates an alternative configuration of the Patient Dashboard 300 in which the patient's lab results 306 may be shown instead of the health score 304. In some configurations, the lab results 306 may be presented in a fishbone diagram or other visual representation that is easy for healthcare professionals to review. FIG. 3C illustrates another alternative configuration of the Patient Dashboard 300 in which the patient's spot check parameters 307 may be displayed rather than the health score 304 or lab results 306. Spot check parameters 307 may be any combination of patient vitals which a healthcare professional measured during the patient's most recent spot check. FIG. 3D is yet another configuration of the Patient Dashboard 300 which may display patient vitals 303 and spot check parameters 307 in a different layout. FIG. 3E is an illustration of the Patient Dashboard 300 in which patient vitals 303, lab results 306, and spot check parameters 307 may all be displayed. Indeed, the Patient Dashboard 300 display may be comprised of any combination of the aforementioned features and patient information. The information displayed on the Patient Dashboard may typically be the background information that medical professionals need before starting a deeper diagnosis. Presently, physicians obtain this information by skimming through a patient's charts while conversing with the patient in the room. Such multi-tasking increases the risk that the physician will overlook critical pieces of information. With the present disclosure, the physician can quickly obtain all the relevant background information before entering the room and may not need to multi-task.

Figure 3F:
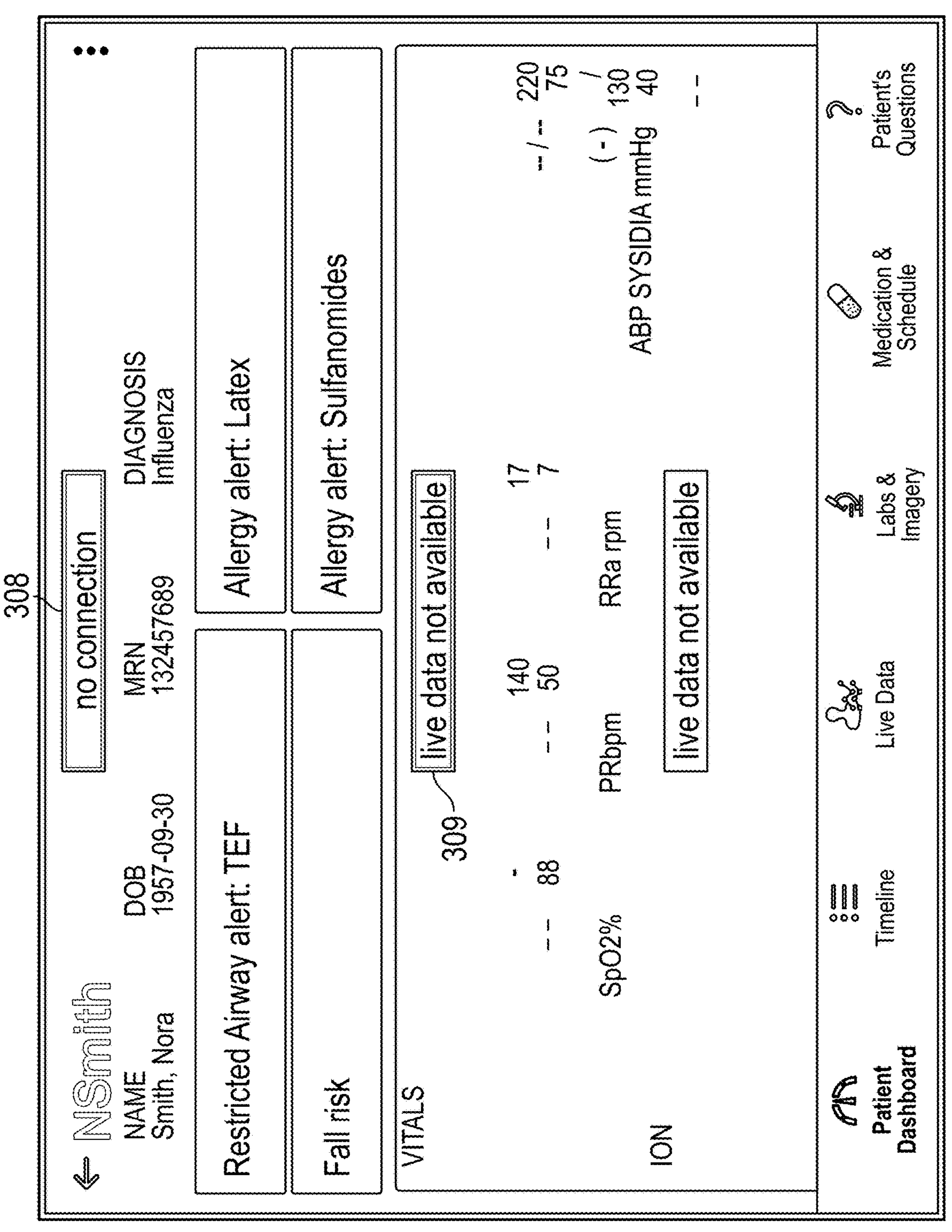

FIG. 3F is an example Patient Dashboard 300 when no patient file is associated with the device, the device is not connected to the hospital network, or any other reason the device cannot receive data updates. In such a case, the Patient Dashboard 300 may display a no connection warning 308 and a missing data warning 309.

Figure 4A:
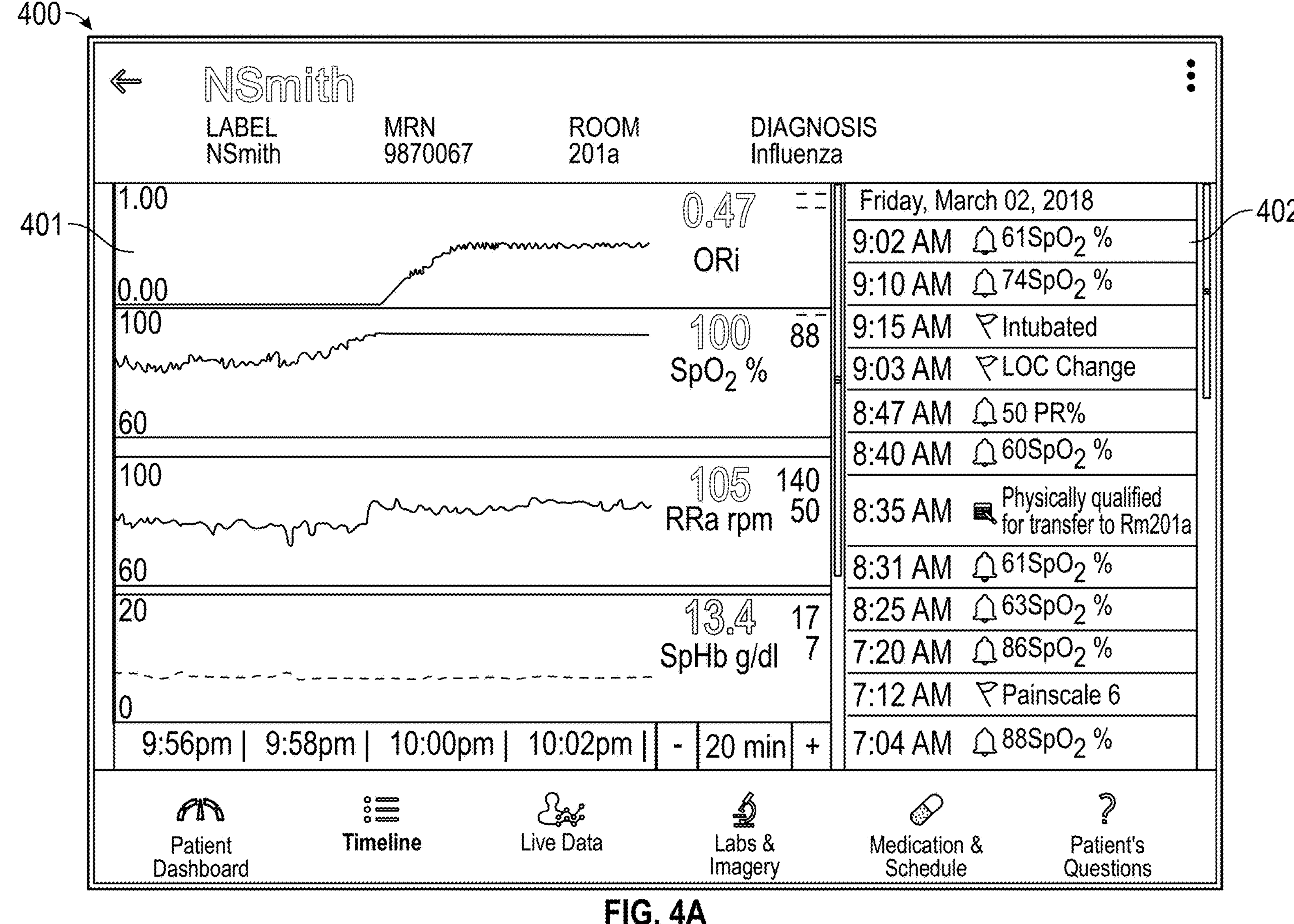
FIGS. 4A-4C are illustrative interfaces for tracking patient progress and medical procedures over time, according to some embodiments.
Figure 4B:
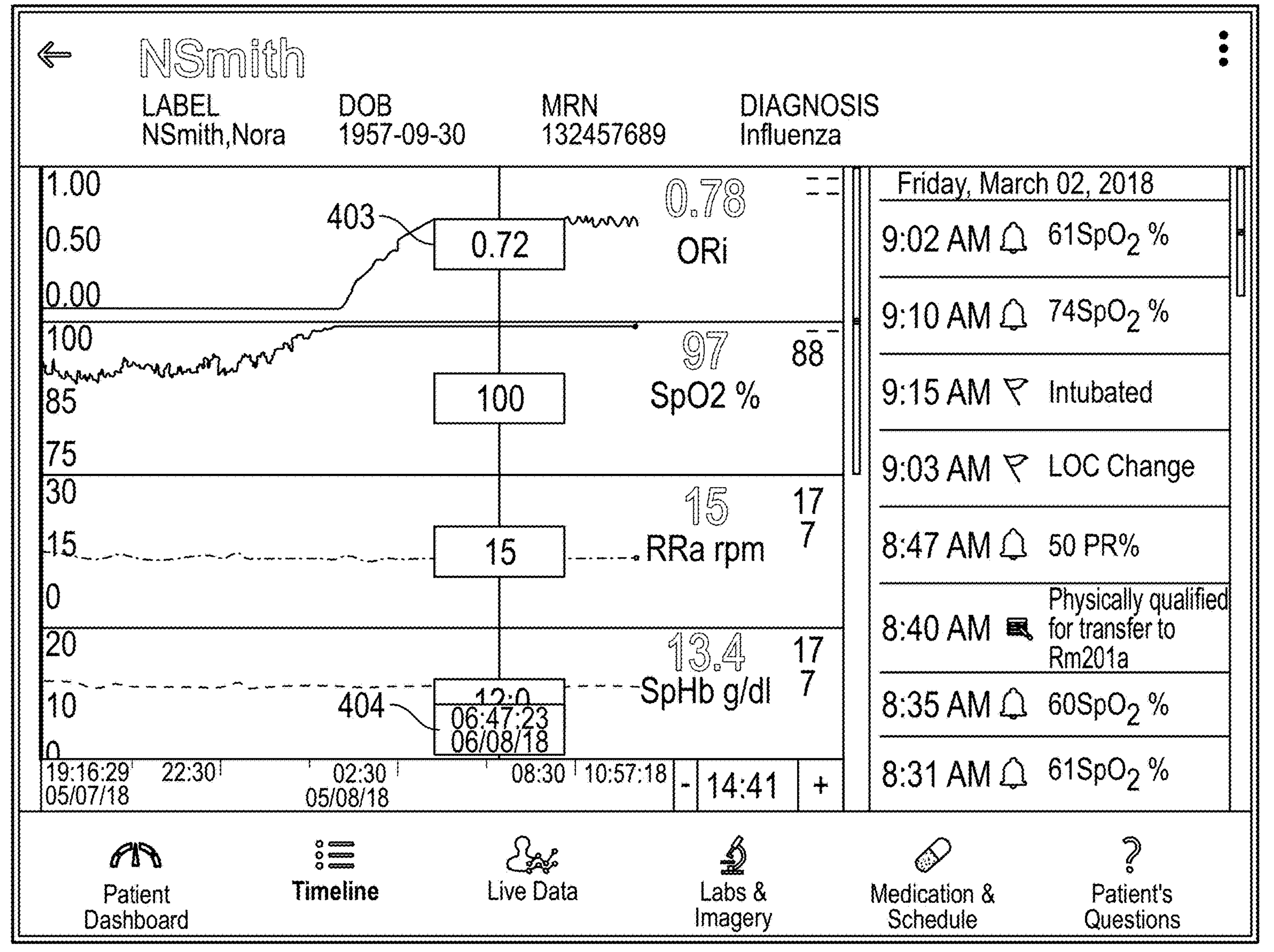
Figure 4C:
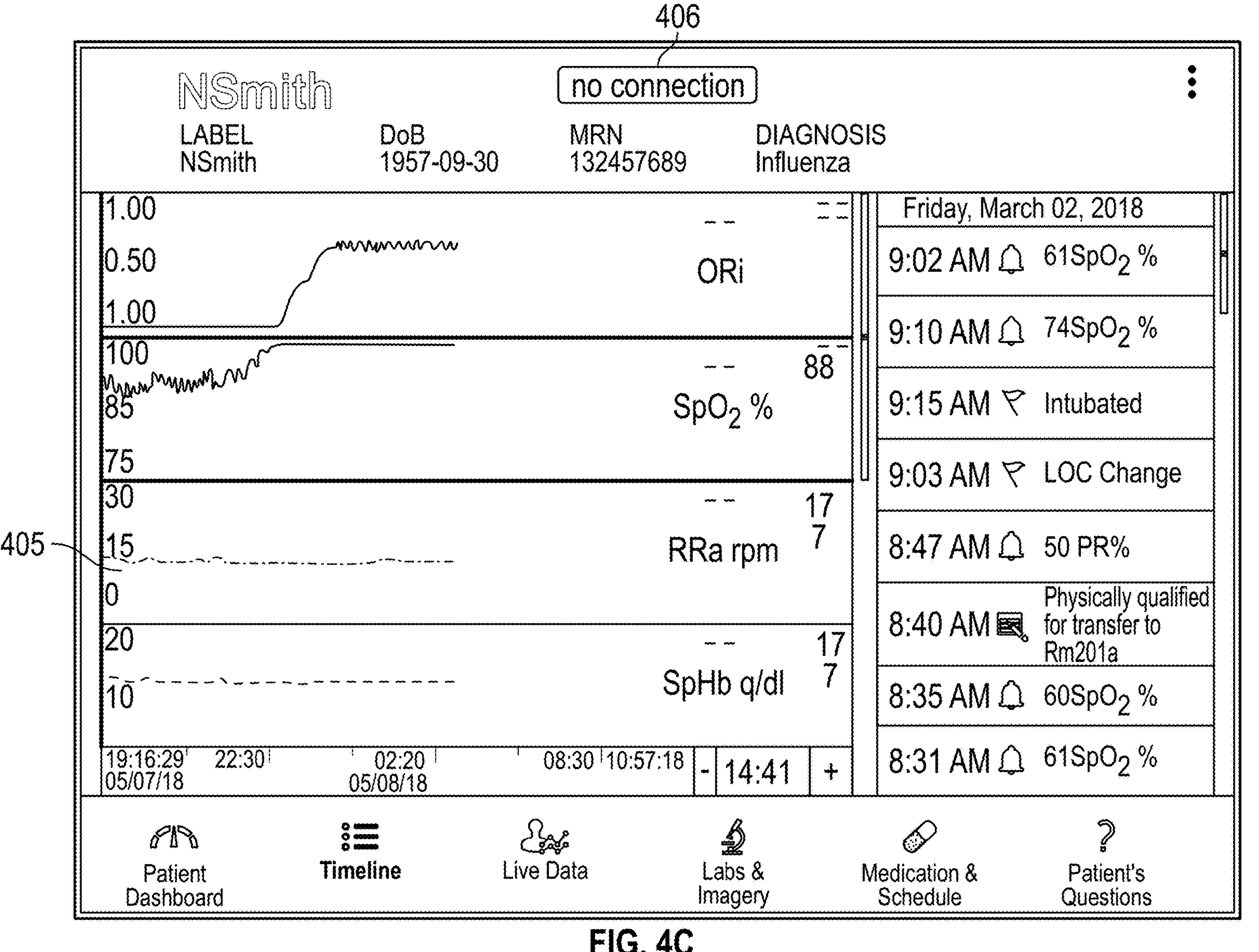

FIGS. 4A-C illustrate an example Timeline screen 400. The Timeline screen 400 may be accessed via the control panel 305. As shown in FIG. 4A, the feature may track the patient's vitals over time and display the data in a graphical representation 401. The feature may also log changes in the patient's vitals and medical procedures performed on the patient, and may display them in a timestamped event timeline 402. A detailed log of events such as the event timeline 402 can help keep every hospital staff member up to date on patient progress and inform their medical decisions. FIG. 4B demonstrates a pinpointing feature. The Timeline feature may allow clinicians to select a particular point on the graphical representation 401 and view the data at that point. Upon selection of a point on the graphical representation 401, the feature may display the vital measurements 403 as well as the time and date 404 at which the measurements were taken. In some configurations, selecting a point on the graphical representation for one vital may automatically also bring up the measurements of all other vitals at that same point in time. FIG. 4C is an example Timeline screen 400 when the patient is disconnected from vitals-monitoring machines, the device loses connection to the hospital network, or any other reason the device may stop receiving data updates. In such cases, the Timeline screen 400 may display a no connection warning 406 and truncated graphical representations 405 which may show patient vitals up until the moment the device stops receiving data updates.

Figure 5A:
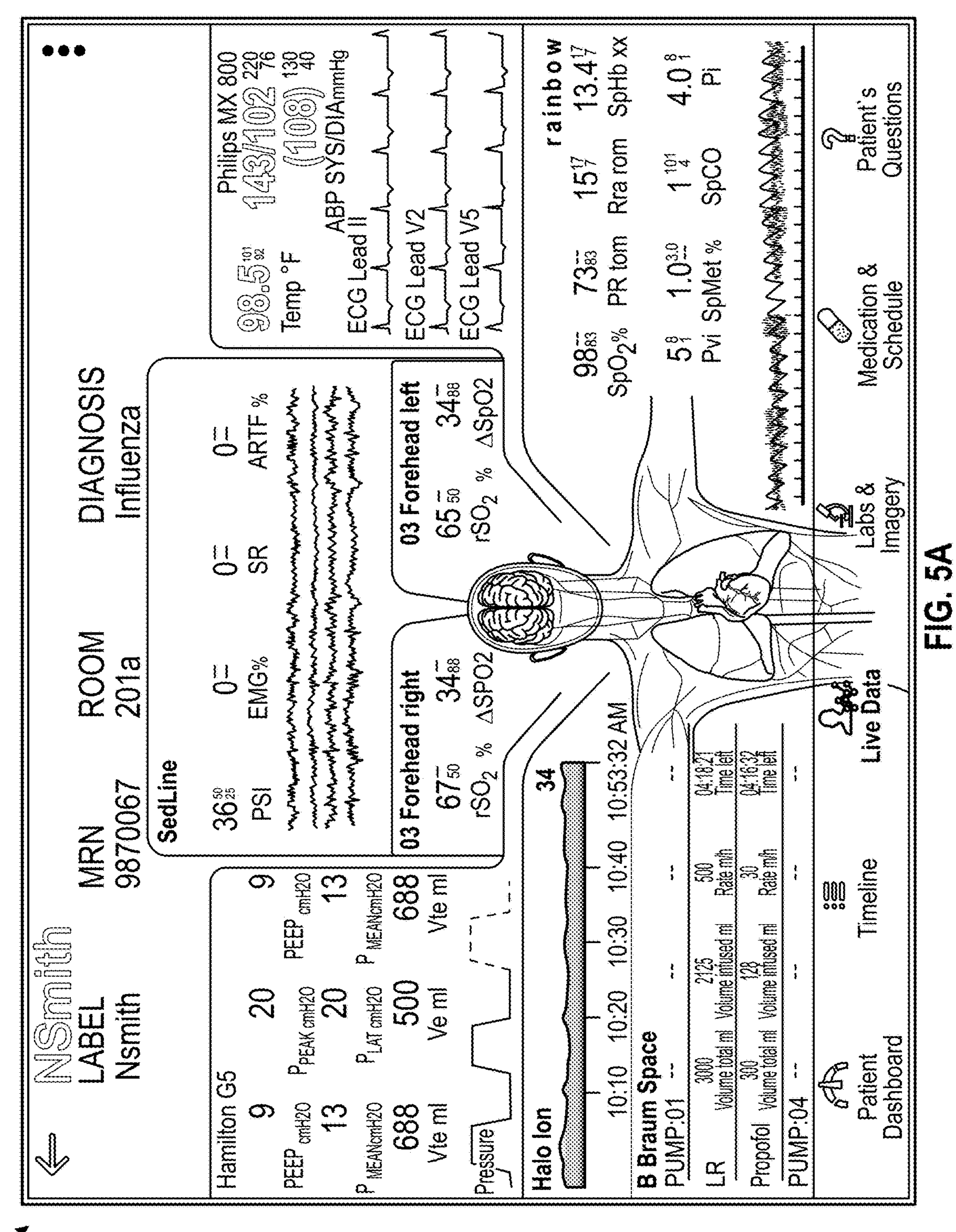
FIGS. 5A and 5B are illustrative interfaces showing real-time updates to the patient's vitals, according to some embodiments.
Figure 5B:
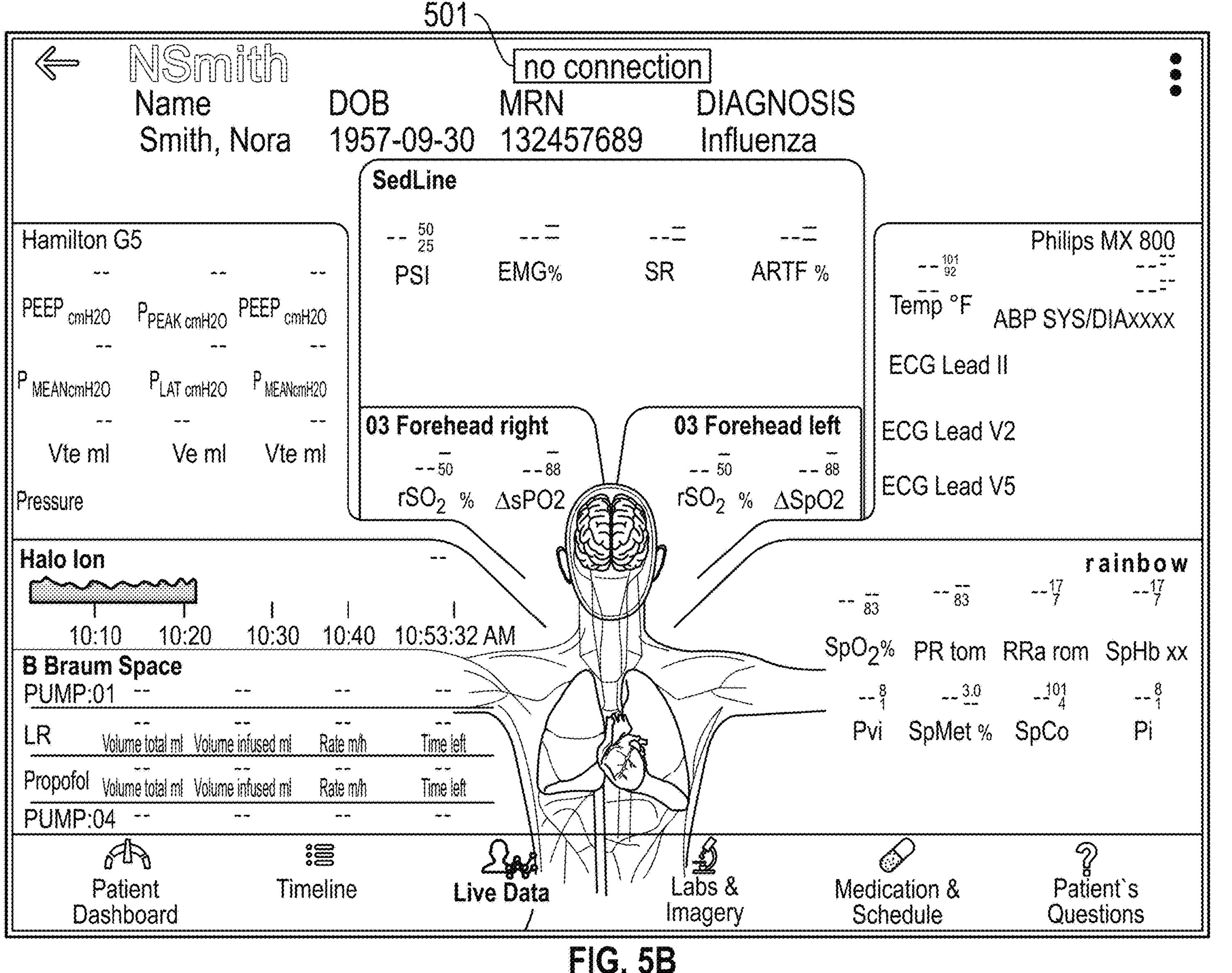

FIG. 5A illustrates an example Live Data screen 500, which may show real-time updates to the patient's vitals. The Live Data screen 500 may be accessed via the control panel 305. The Live Data screen 500 may be configurable to show any number of physiologic measurements, such as, but not limited to, basic patient information 301, patient vitals 303, patient health score 304, etc. FIG. 5B illustrates an example Live Data screen 500 when the patient is disconnected from vitals-monitoring machines, the device loses connection to the hospital network, or any other reason the device may stop receiving data updates. In such cases, the Live Data screen 500 may display a no connection warning 501. The screen 500 may indicate a lack of patient data by substituting dashes where physiologic measurements are usually listed, leaving the display space blank, or any other method of showing that the device is not receiving patient data.

Figure 6B:
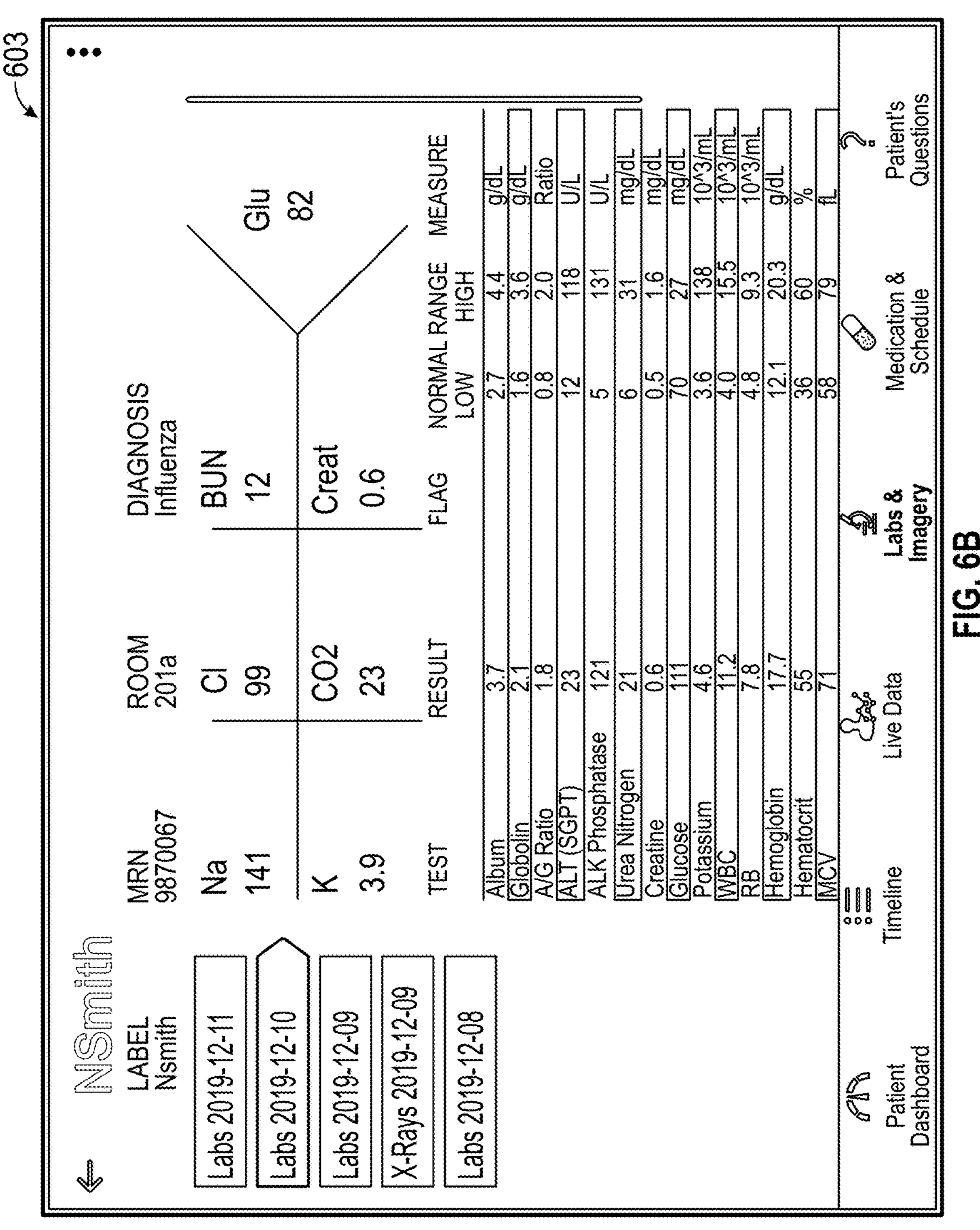
Figure 6E:
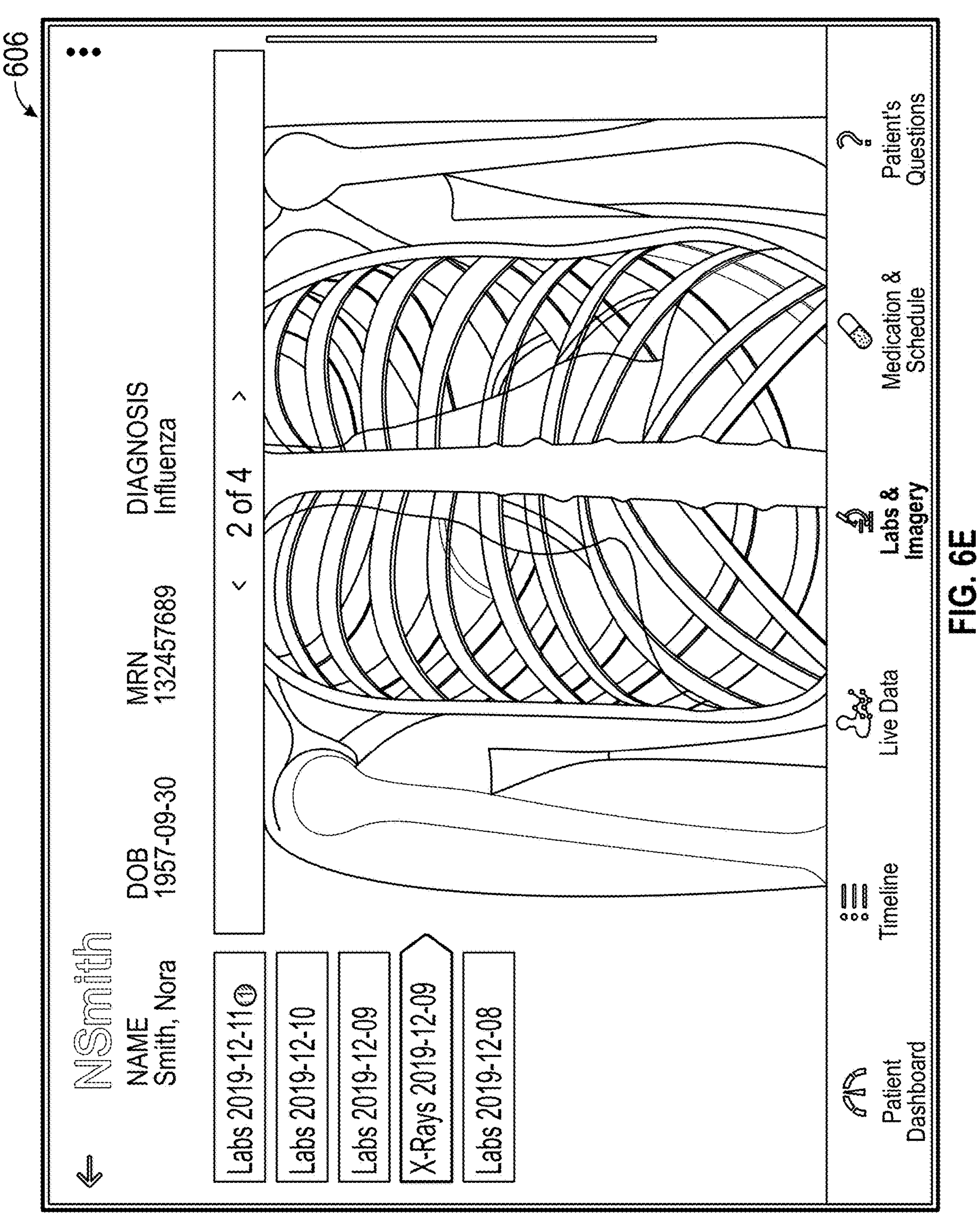
Figure 6F:
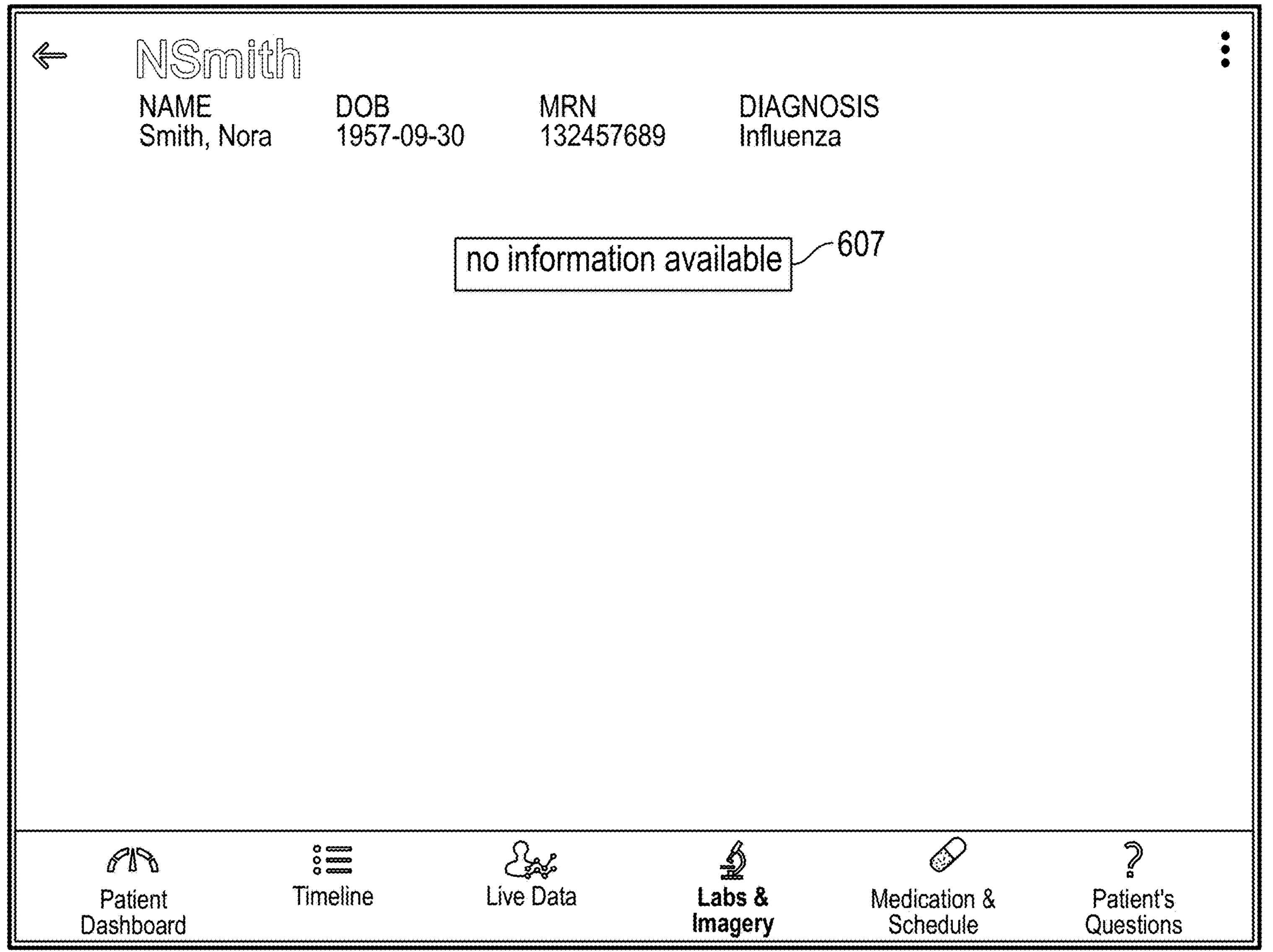

FIG. 6A shows an example Labs & Imagery screen 600, which may display the patient's lab results 601. The Labs & Imagery screen 600 may be accessed via the control panel 305. The navigation tabs 602 can allow the physician to select lab results by test and even to view patient x-rays. FIGS. 6B-6D show alternate layouts that may support one-fishbone chart display 603, two-fishbone chart display 604, or three-fishbone chart display 605. In some configurations, the layouts which display fishbone charts also display the patient's full lab results 601. In other configurations, the layouts with fishbone charts may only display fishbone charts to summarize the lab results. Typically, not all parts of a lab report are important in a diagnosis, and the alternate layouts may consolidate the most important information in a digestible format for physicians, which can allow them to work more efficiently. FIG. 6E is an example x-ray viewing screen 606 where physicians can review the patient's x-rays. FIG. 6F illustrates an example Labs & Imagery screen 600 when the patient file is empty, the device loses connection to the hospital network, or any other reason the device may not receive data updates. In such cases, the Labs & Imagery screen 600 may display a no connection warning 607.

Figure 7A:
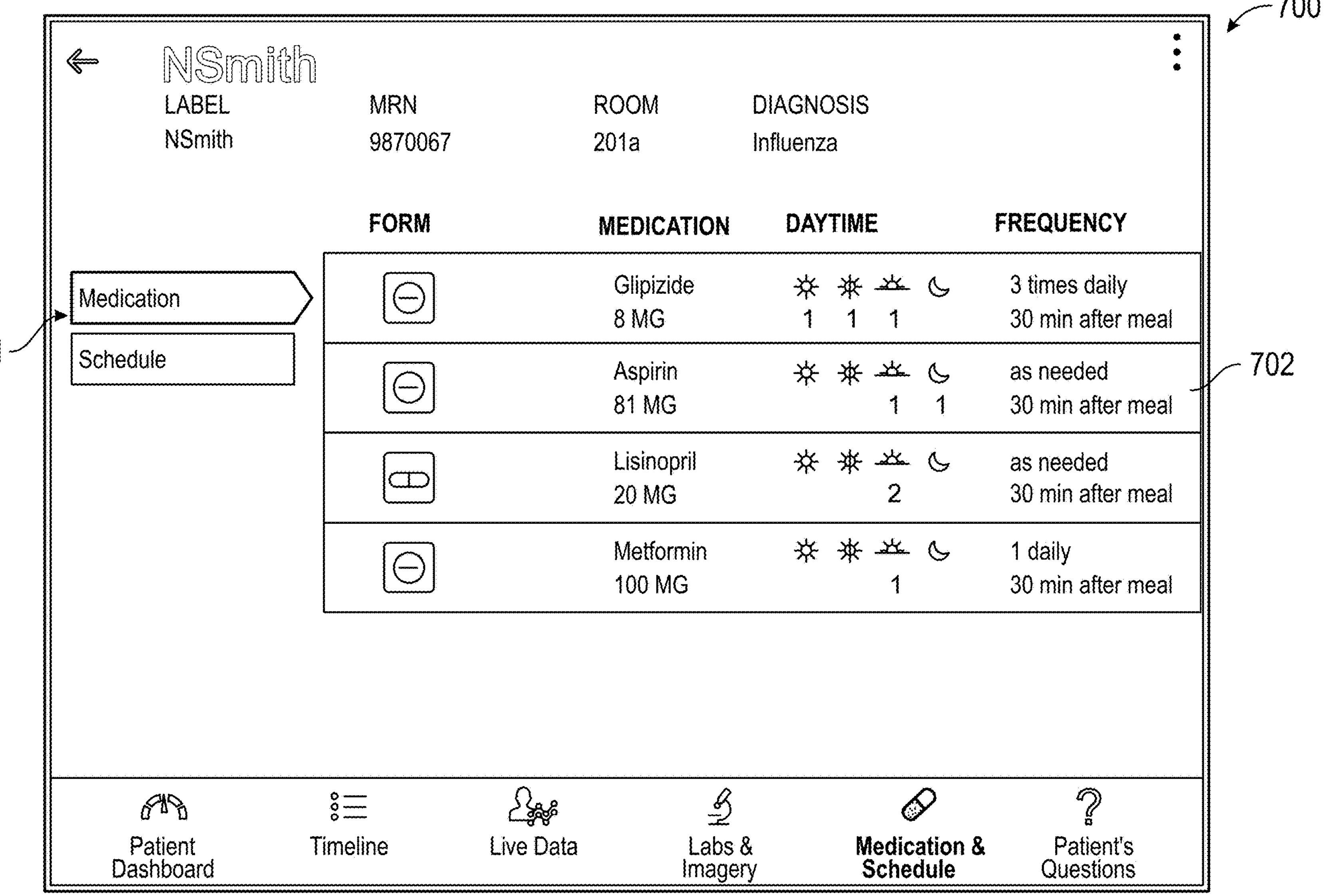
FIGS. 7A-7D are illustrative interfaces showing a patient's medication details and daily schedule, according to some embodiments.
Figure 7B:
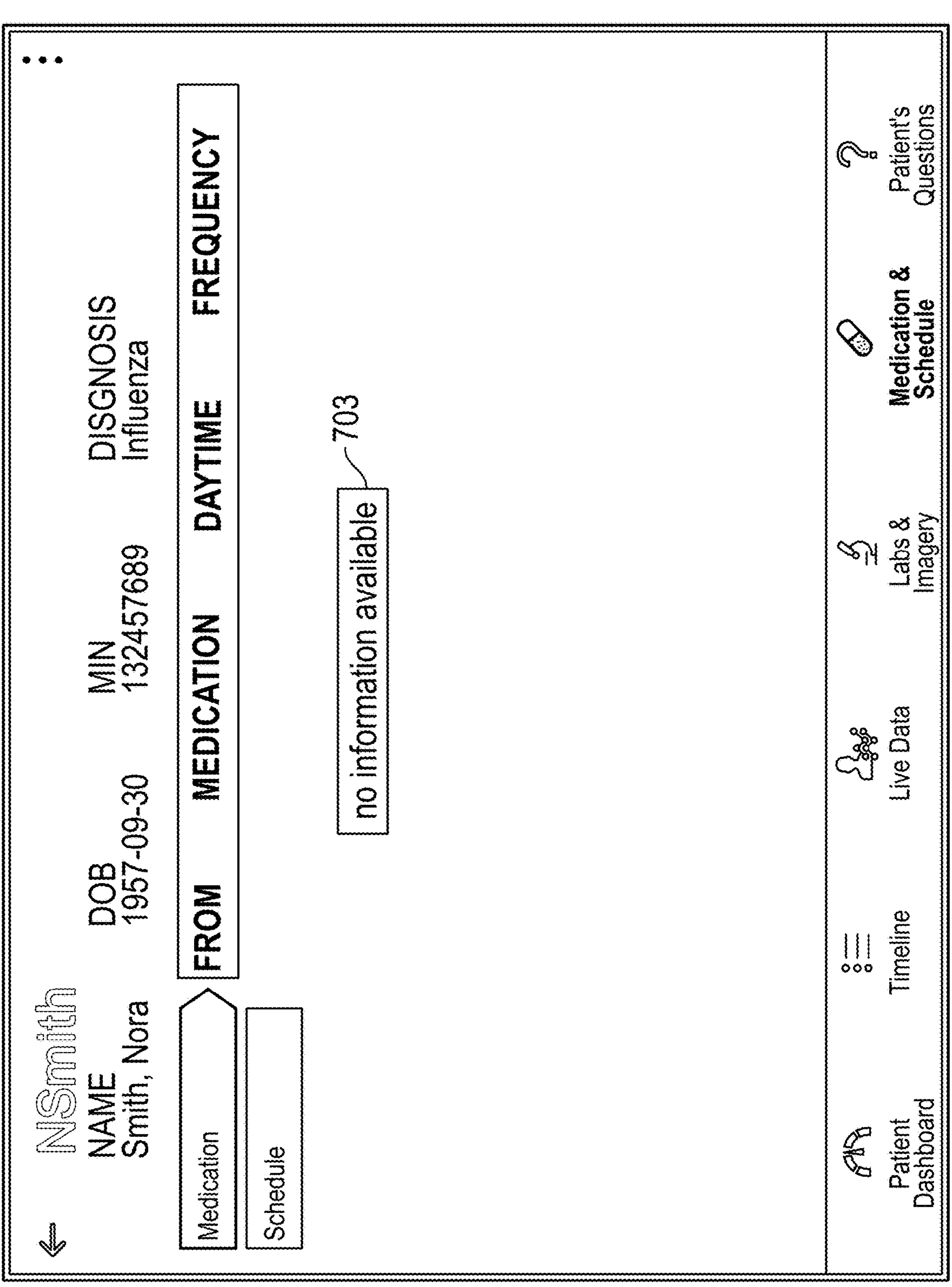
Figure 7C:
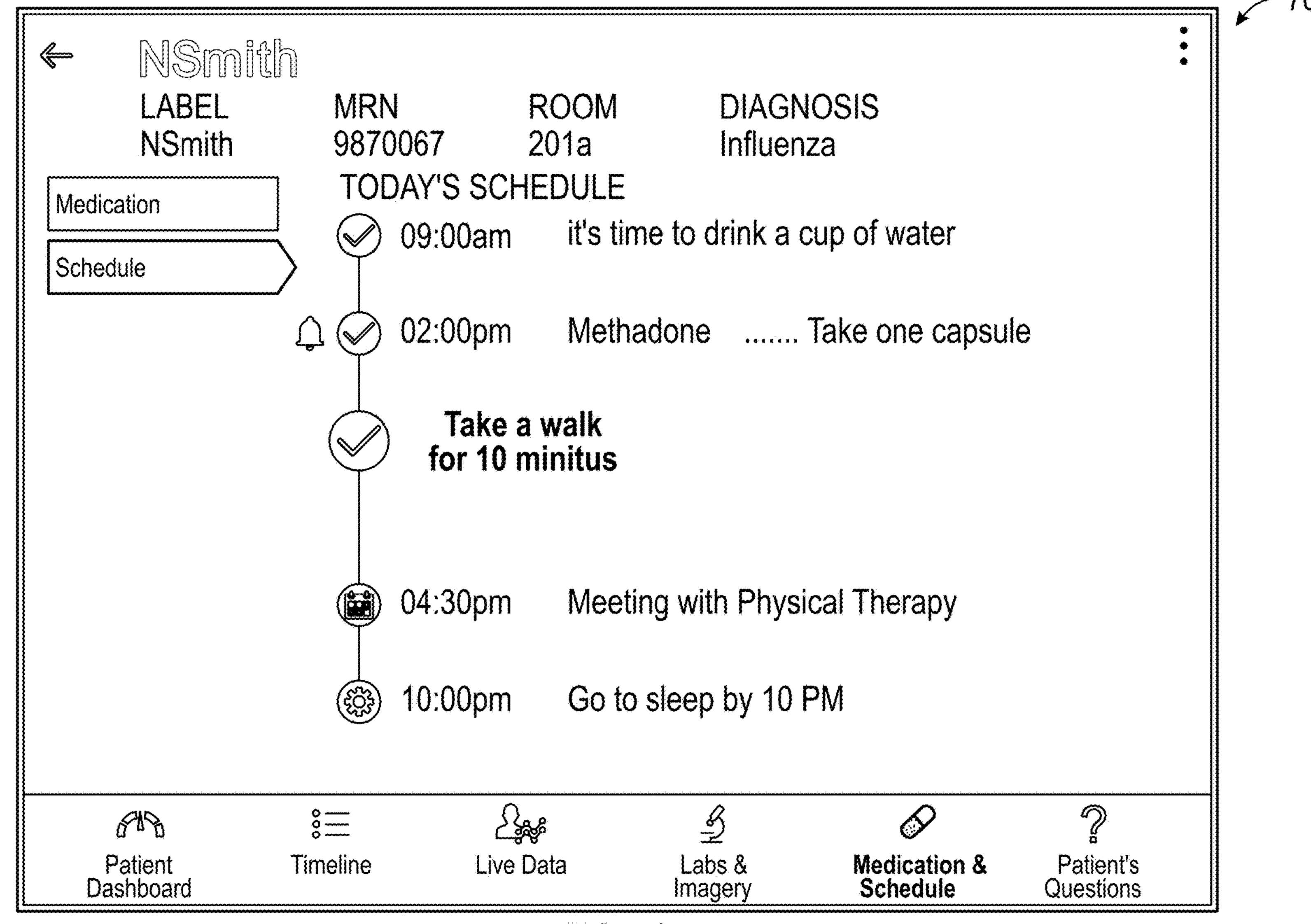
Figure 7D:
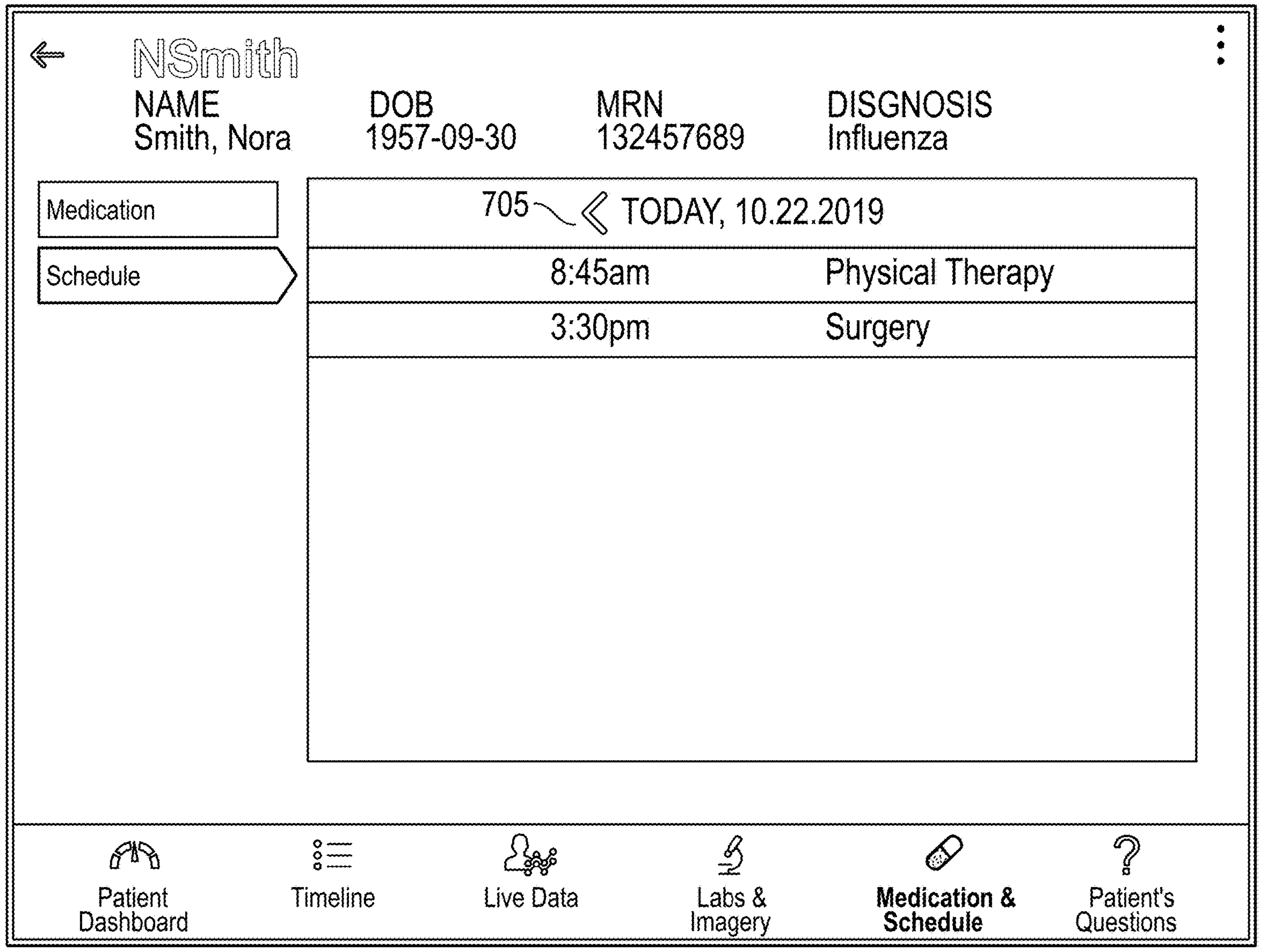

FIGS. 7A-7D show an example Medication & Schedule screen 700. The Medication & Schedule screen 700 may be accessed via the control panel 305. As shown in FIG. 7A, the navigation menu 701 can allow the medical staff to view the patient's prescribed medication details 702 and daily schedule 704 (as shown in FIG. 7C). The medication details 702 may include, but is not limited to, the name of the medication, information regarding administration of the medication, the physical form of the medication, etc. FIG. 7B illustrates an example Medication & Schedule screen 700 when the patient does not have prescribed medications, the device loses connection to the hospital network, or any other reason the device may not receive data updates. In such cases, the interface may display a no information warning 703. FIG. 7C is an exemplary illustration of the schedule sub-screen 704, which may display the patient's daily schedule. The daily schedule may include details of each planned activity or event and may include a time for each event. The schedule sub-screen 704 may also indicate whether an activity has been completed. The activity may be automatically marked as completed once the scheduled time has passed, or the activity may only be marked as completed based on healthcare provider input. FIG. 7D is an alternative configuration of the schedule sub-screen 704, in which the user may scroll through different days' schedules via a date selector 705.

Figure 8:
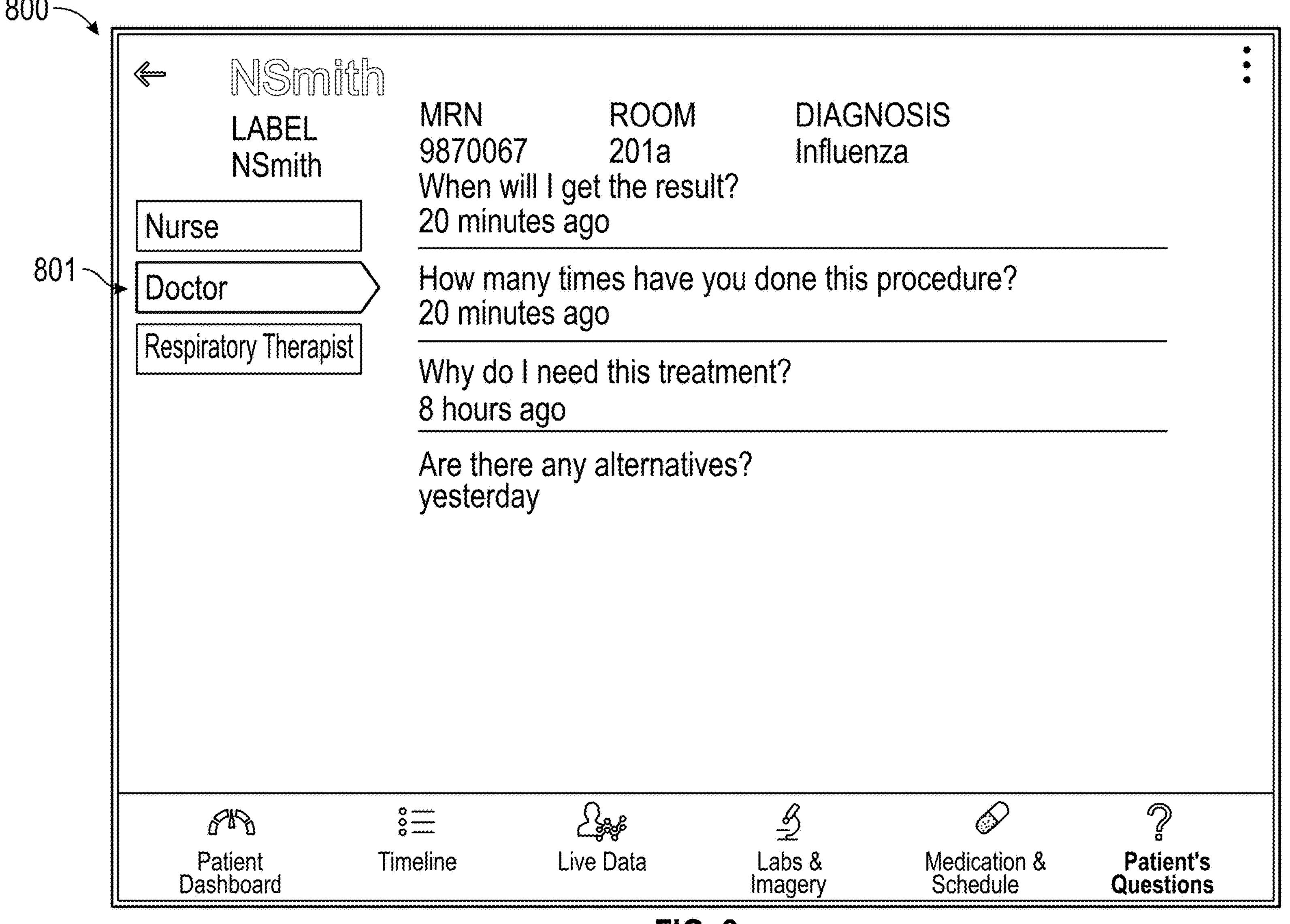
FIG. 8 is an illustrative interface showing patient questions for various specialists.

FIG. 8 shows an example Patient's Questions screen 800. The Patient's Questions screen 800 may be accessed via the control panel 305. The Patient's Questions screen 800 may display questions that patients input to a corresponding patient-facing interface of the physiological patient monitoring system. The patient-facing interface may be accessed through an application on a patient-accessible portable device. The staff selection panel 801 can allow medical staff to view only the questions that pertain to them. The staff selection panel 801 may list specific specialists, such as radiologist, oncologist, or respiratory therapist, rather than just generic titles such as doctor or nurse.

Figure 9A:
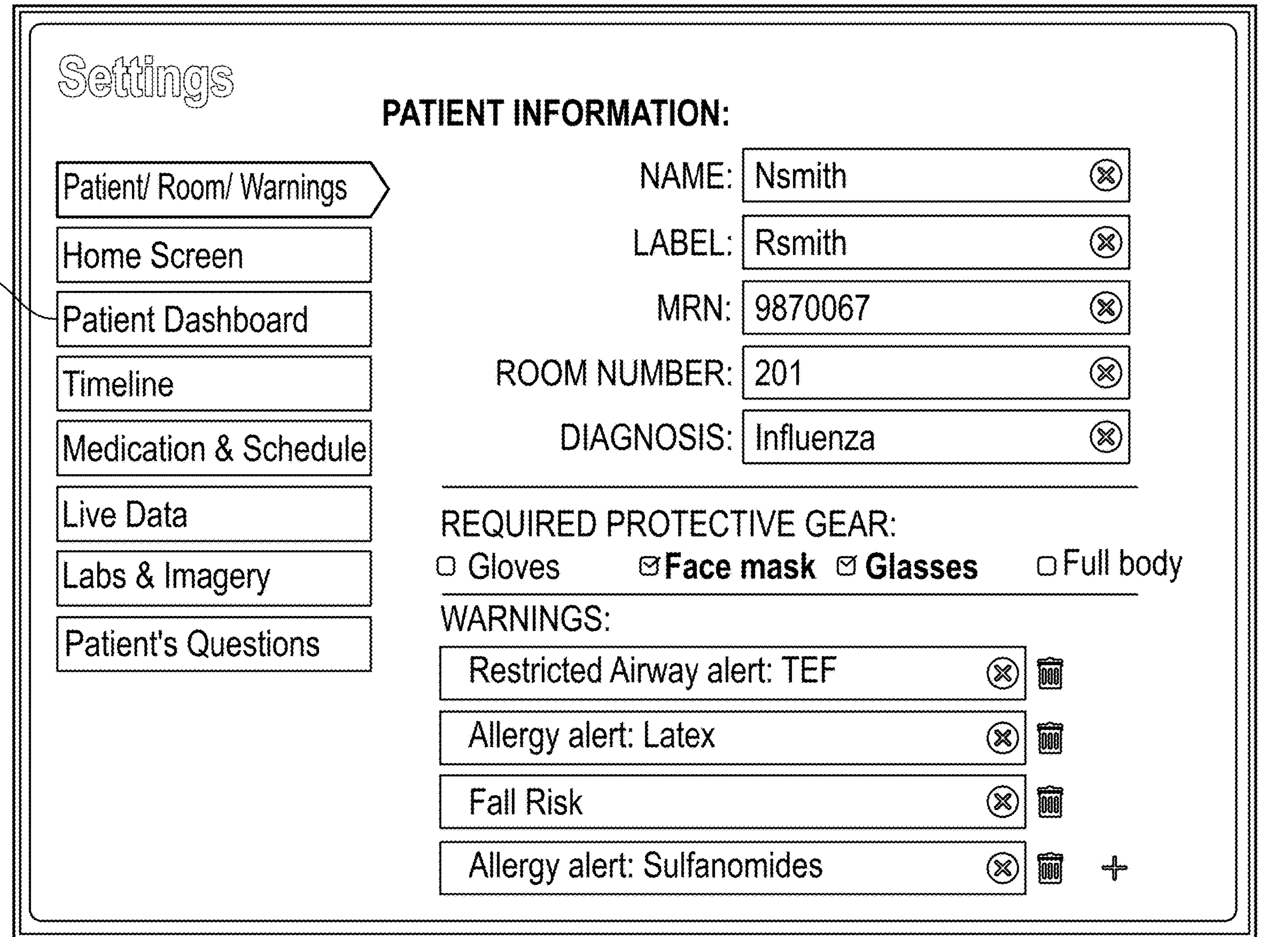
FIGS. 9A-9O are illustrative interfaces of the settings page of a physiological patient monitoring system where hospital staff can update display preferences, according to some embodiments.
Figure 9B:
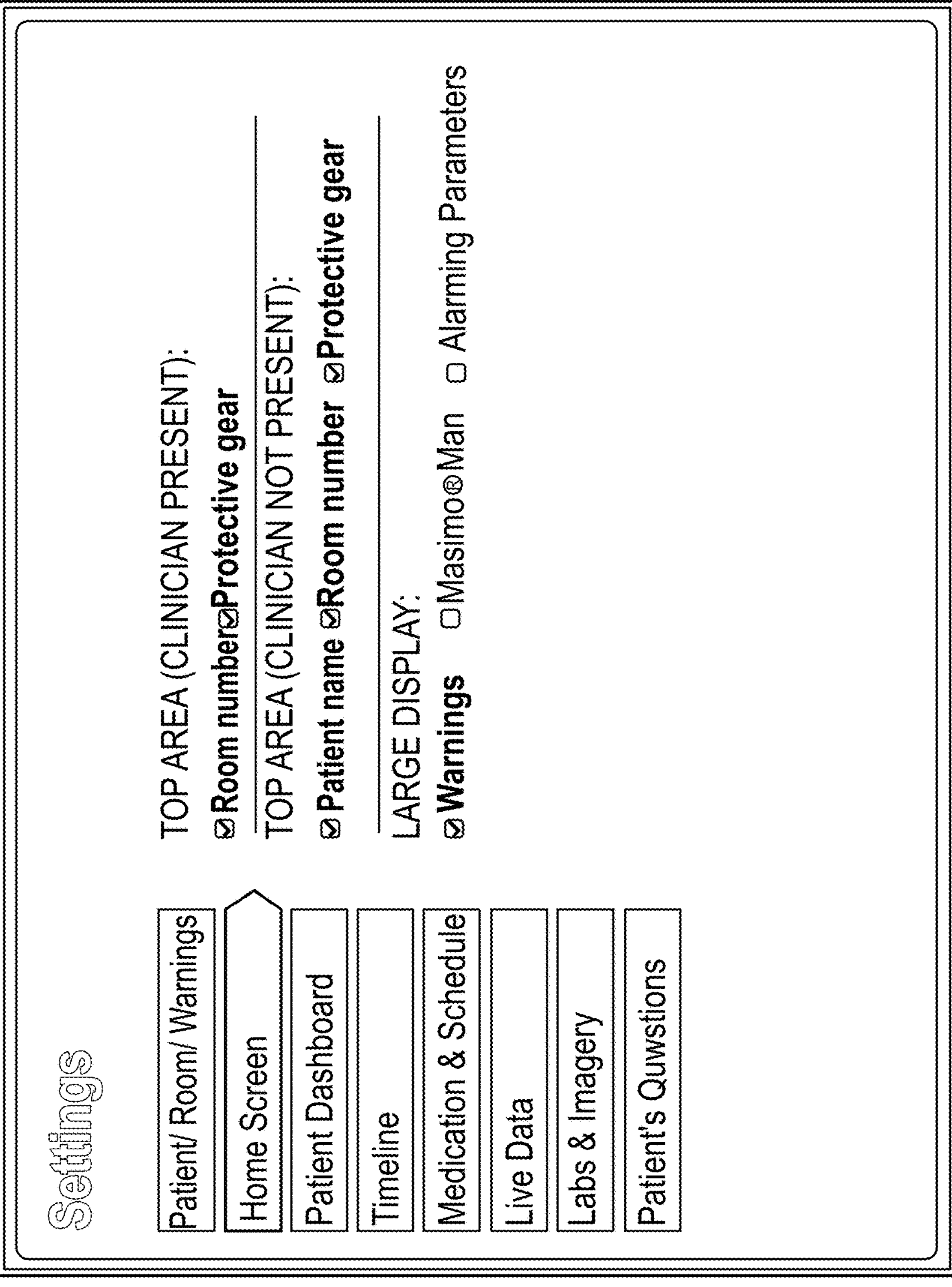
Figure 9C:
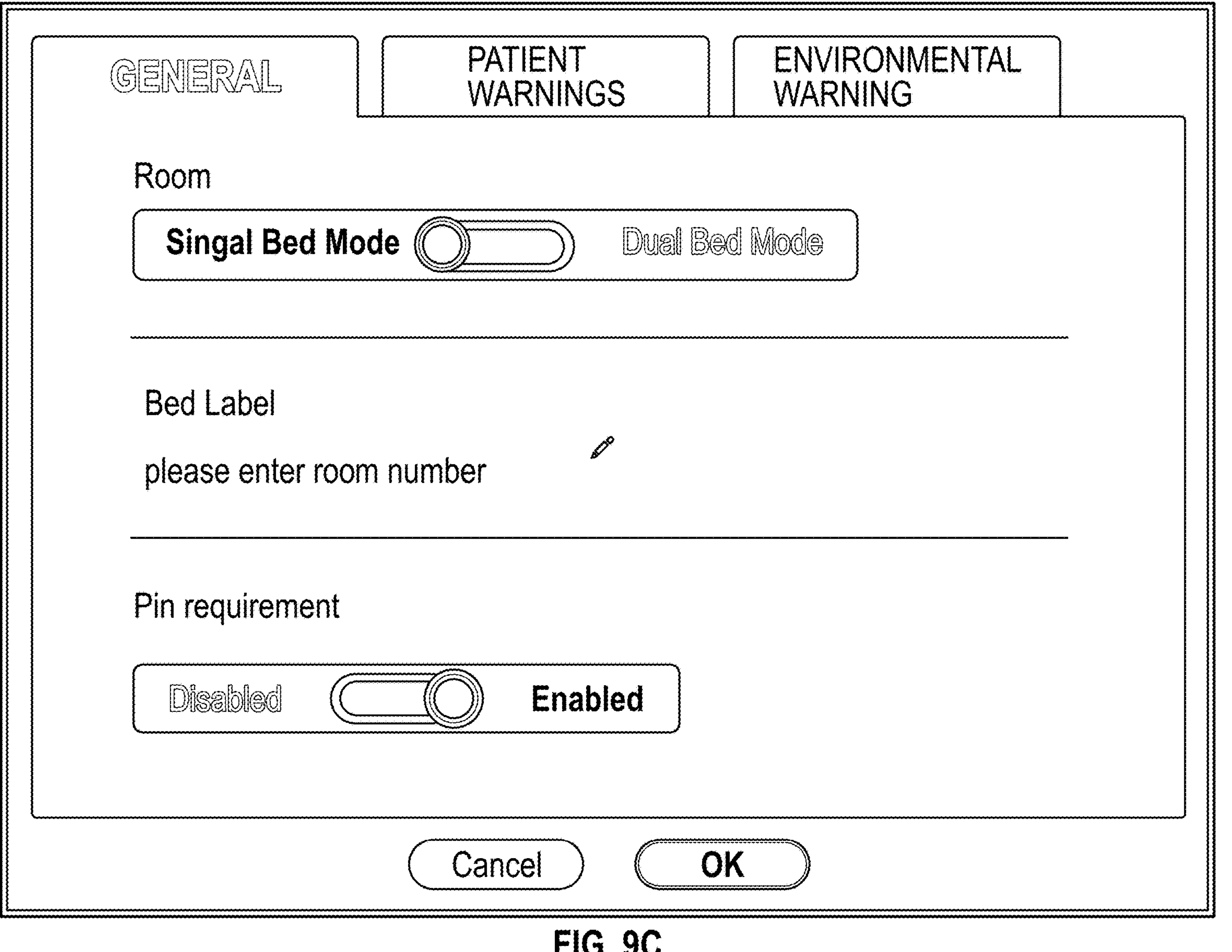
Figure 9D:
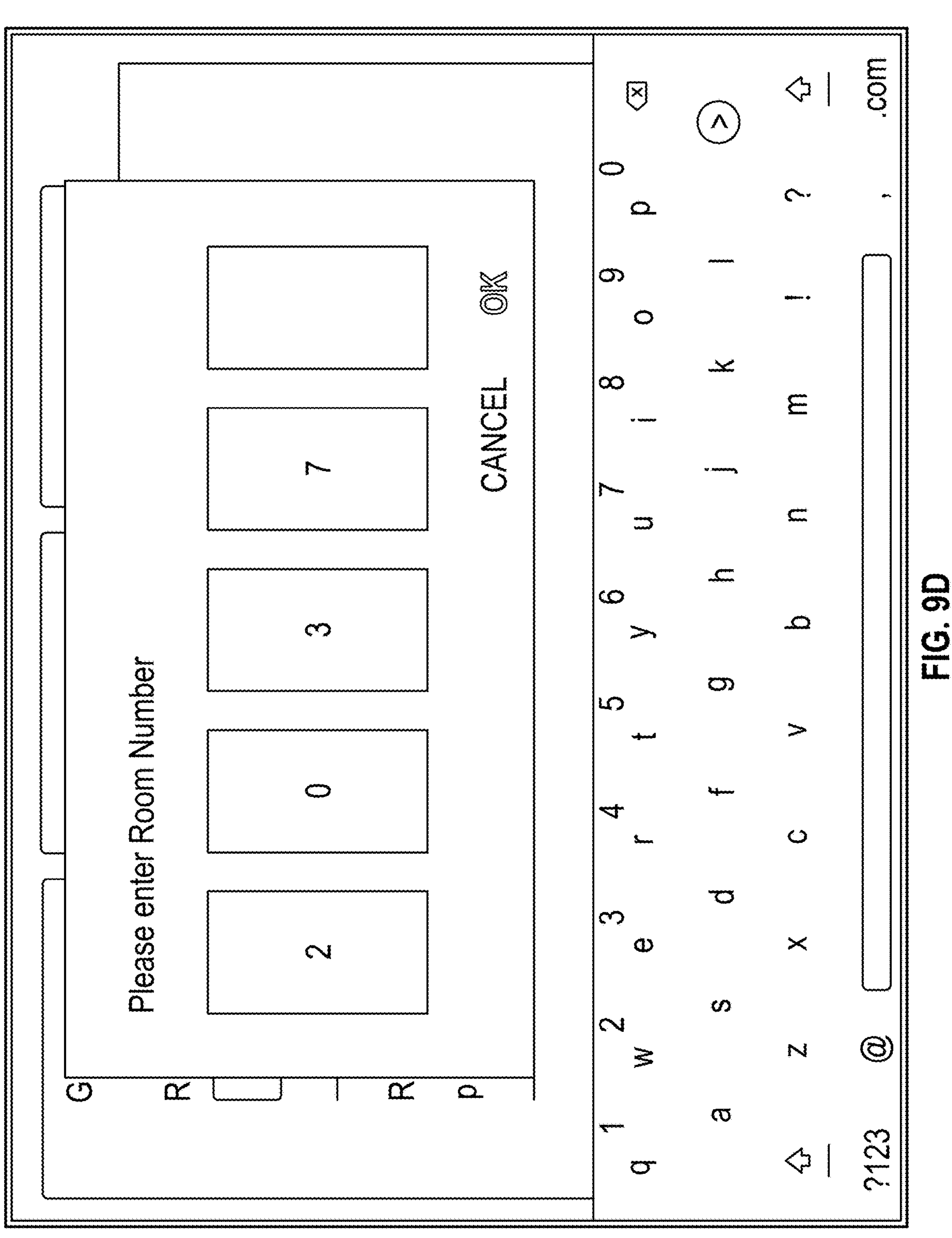
Figure 9E:
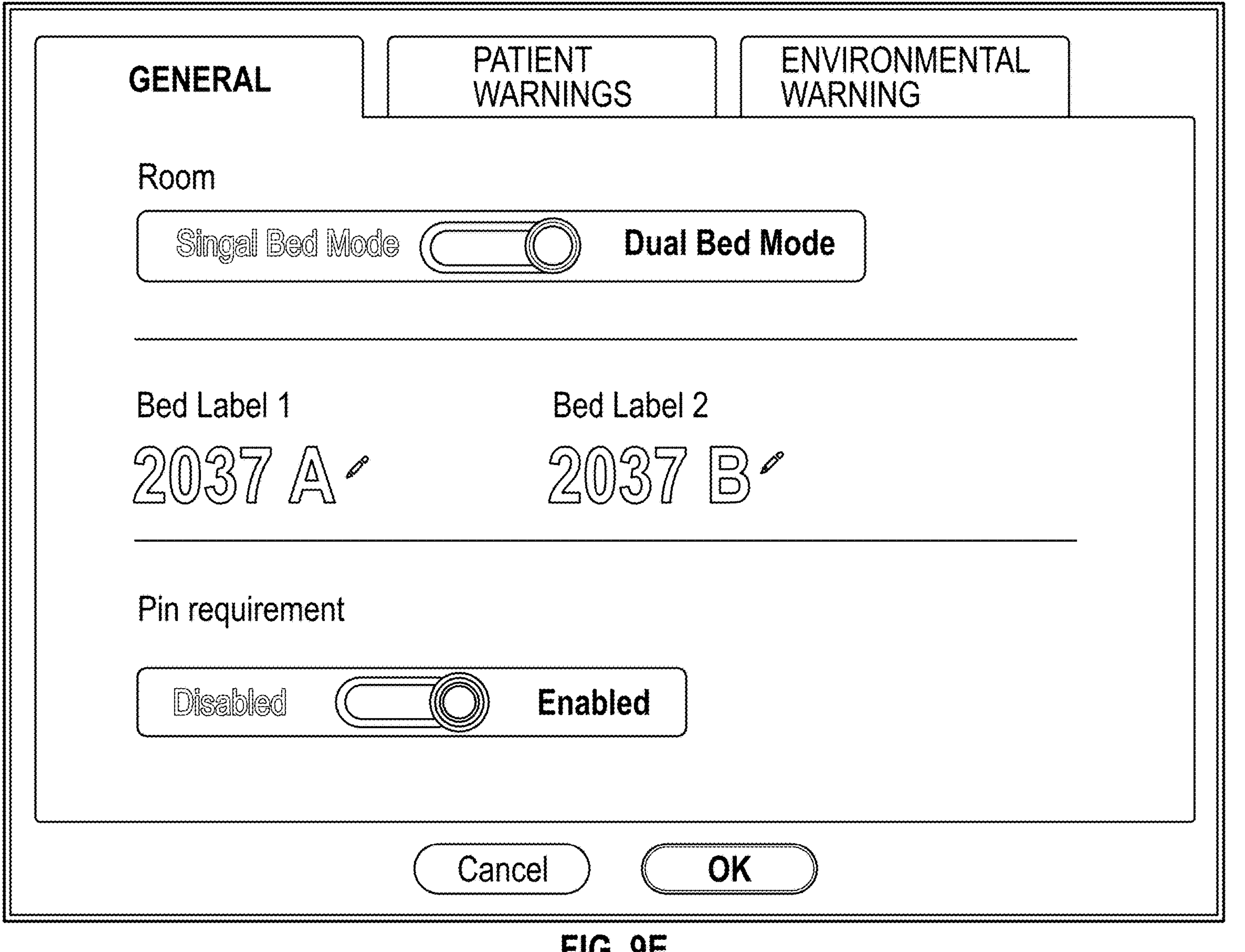
Figure 9F:
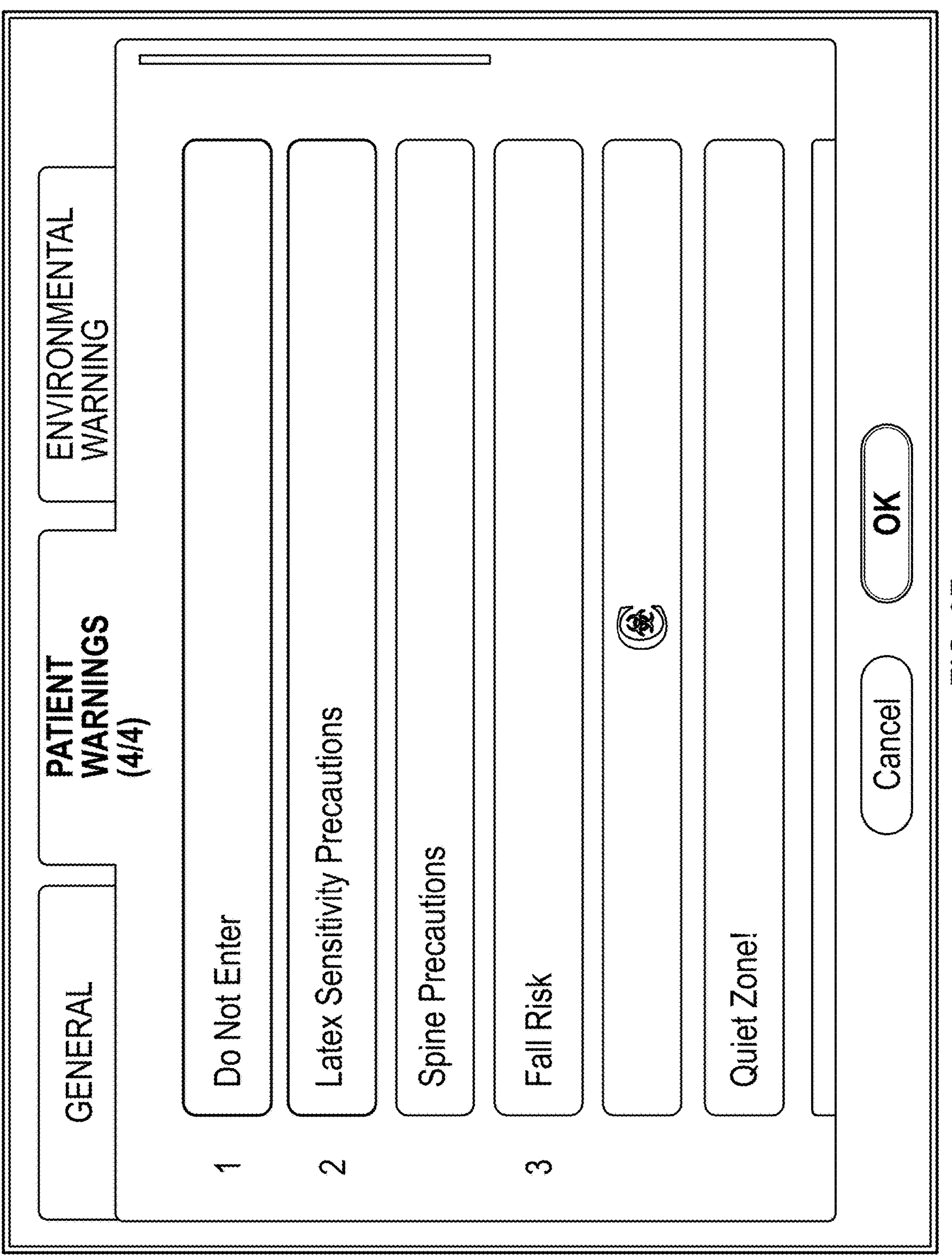
Figure 9G:
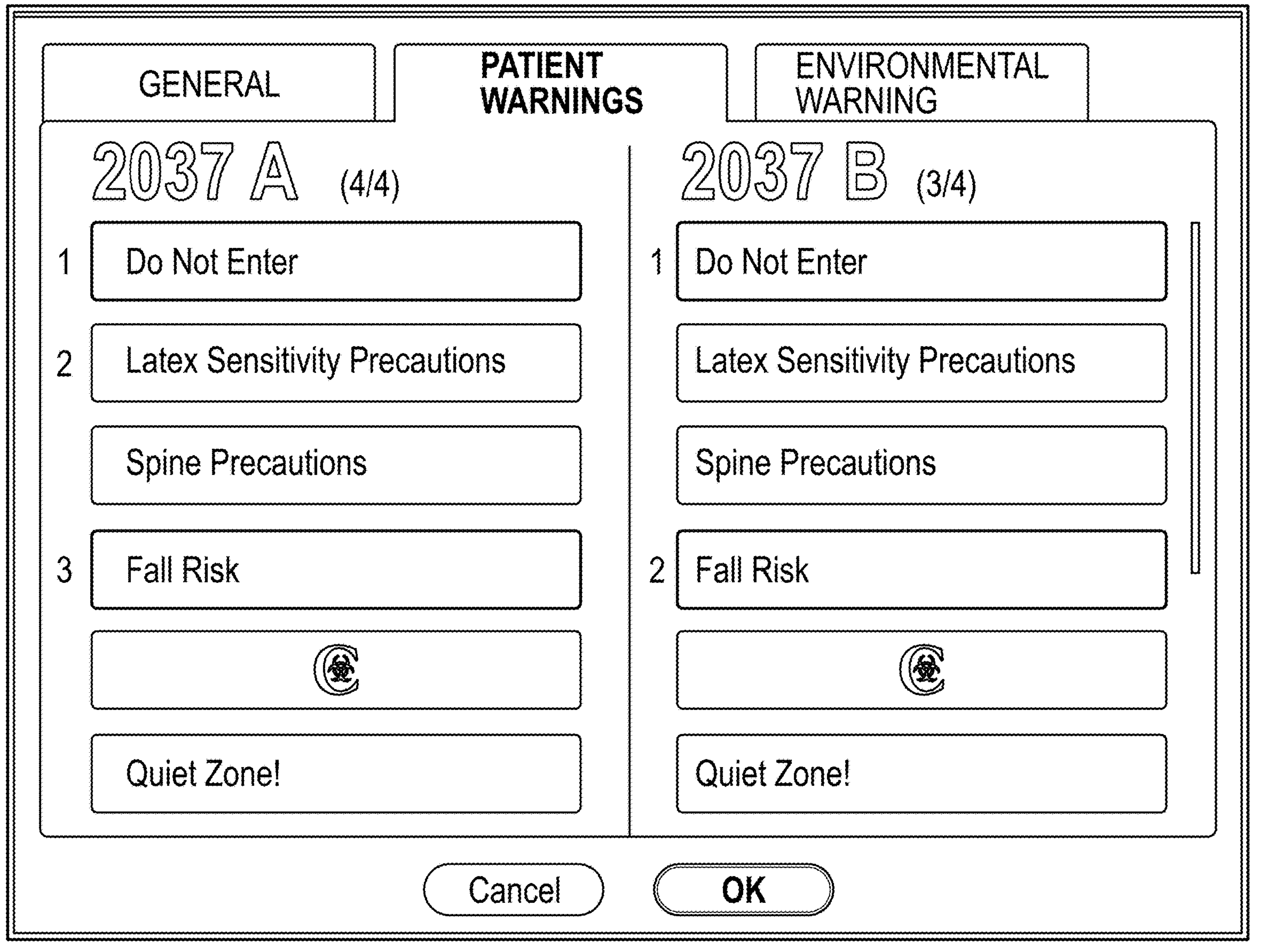
Figure 9H:
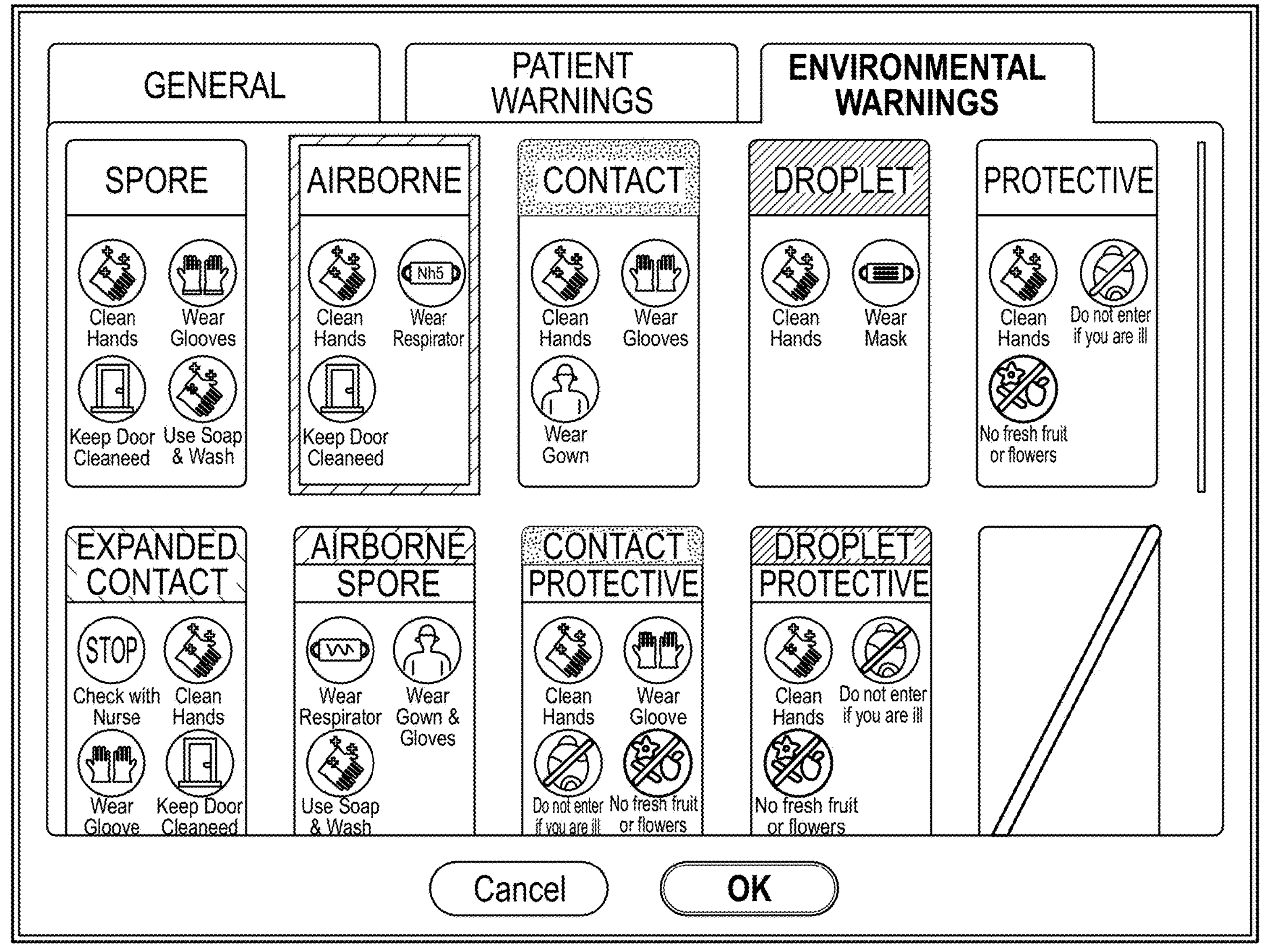
Figure 9I:
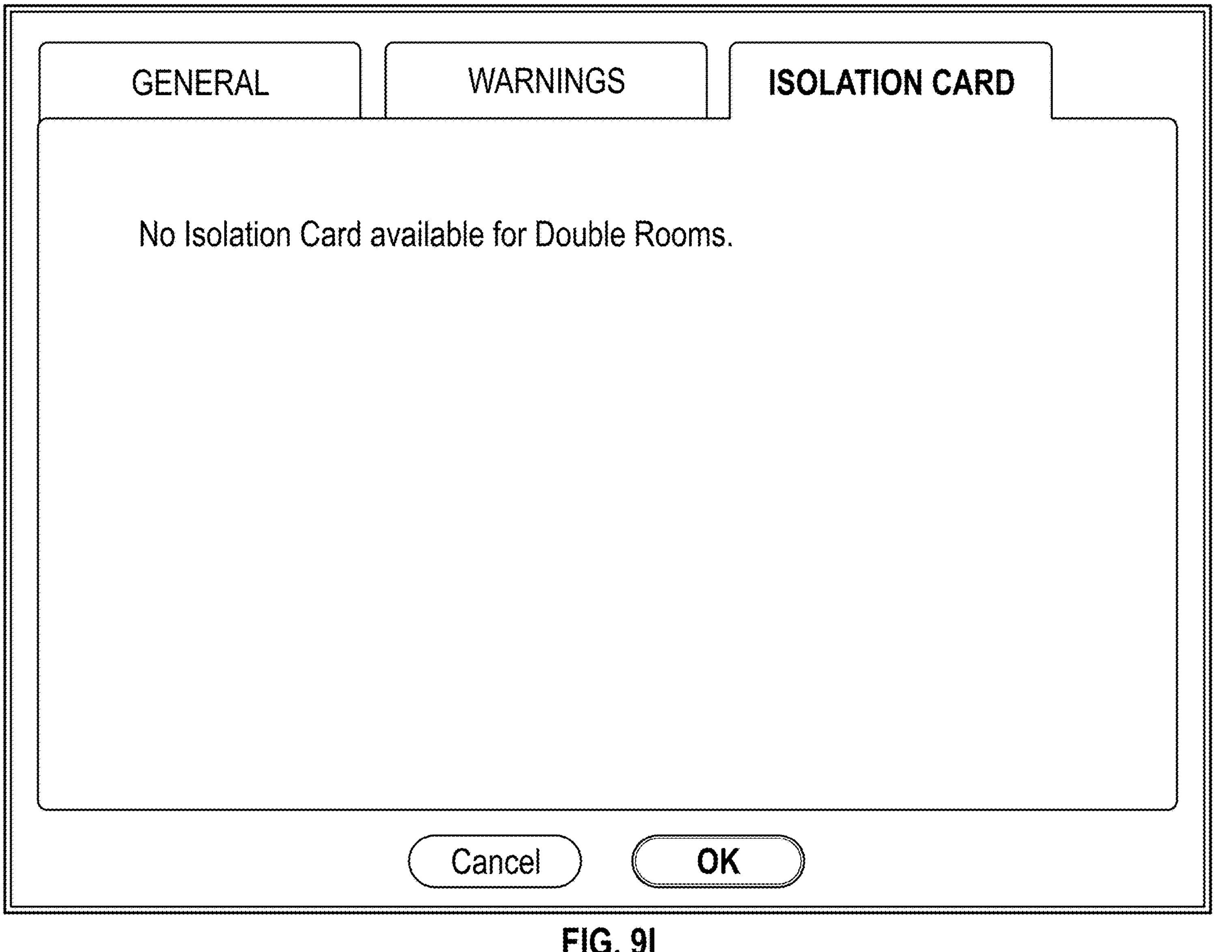
Figure 9J:
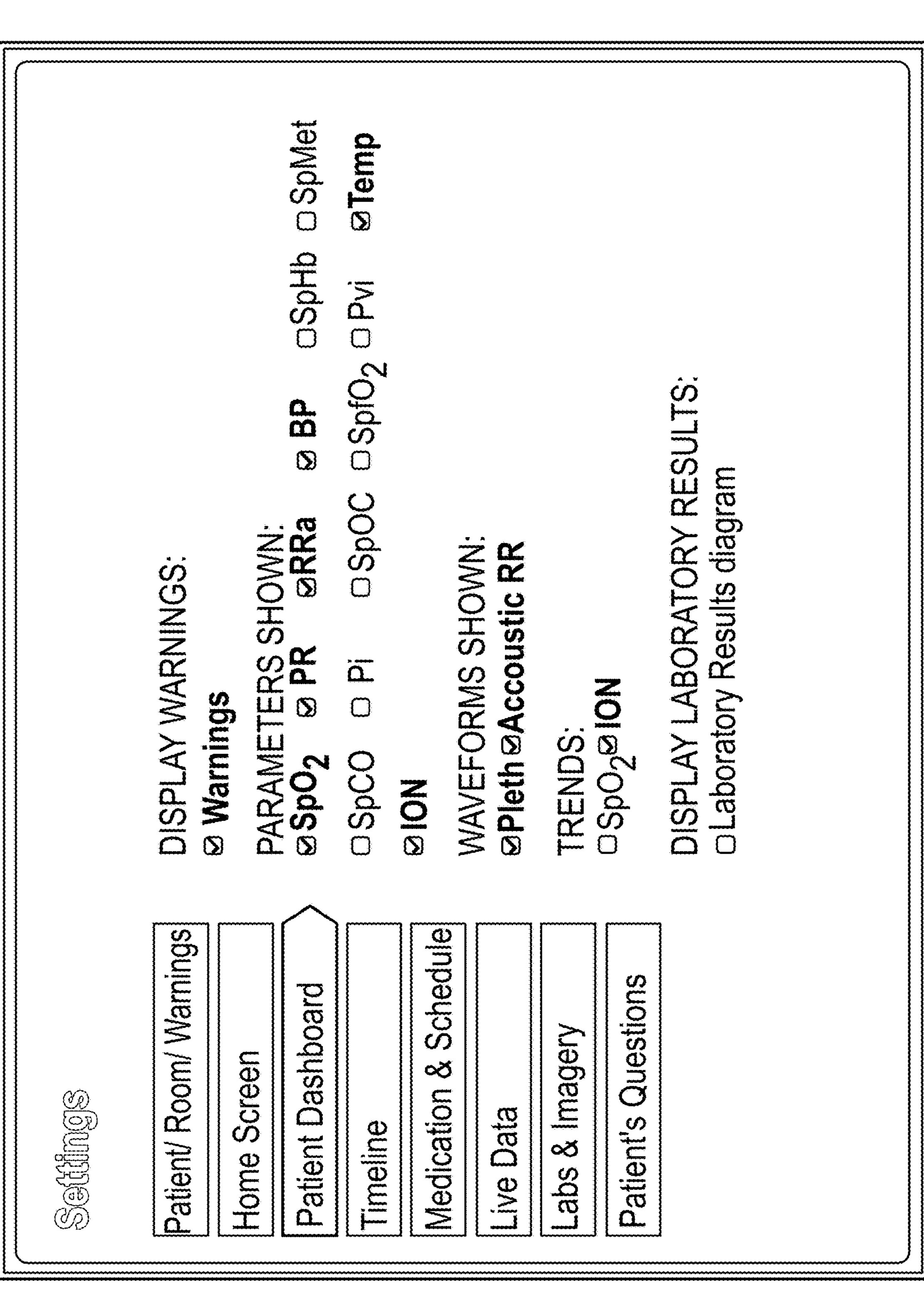
Figure 9K:
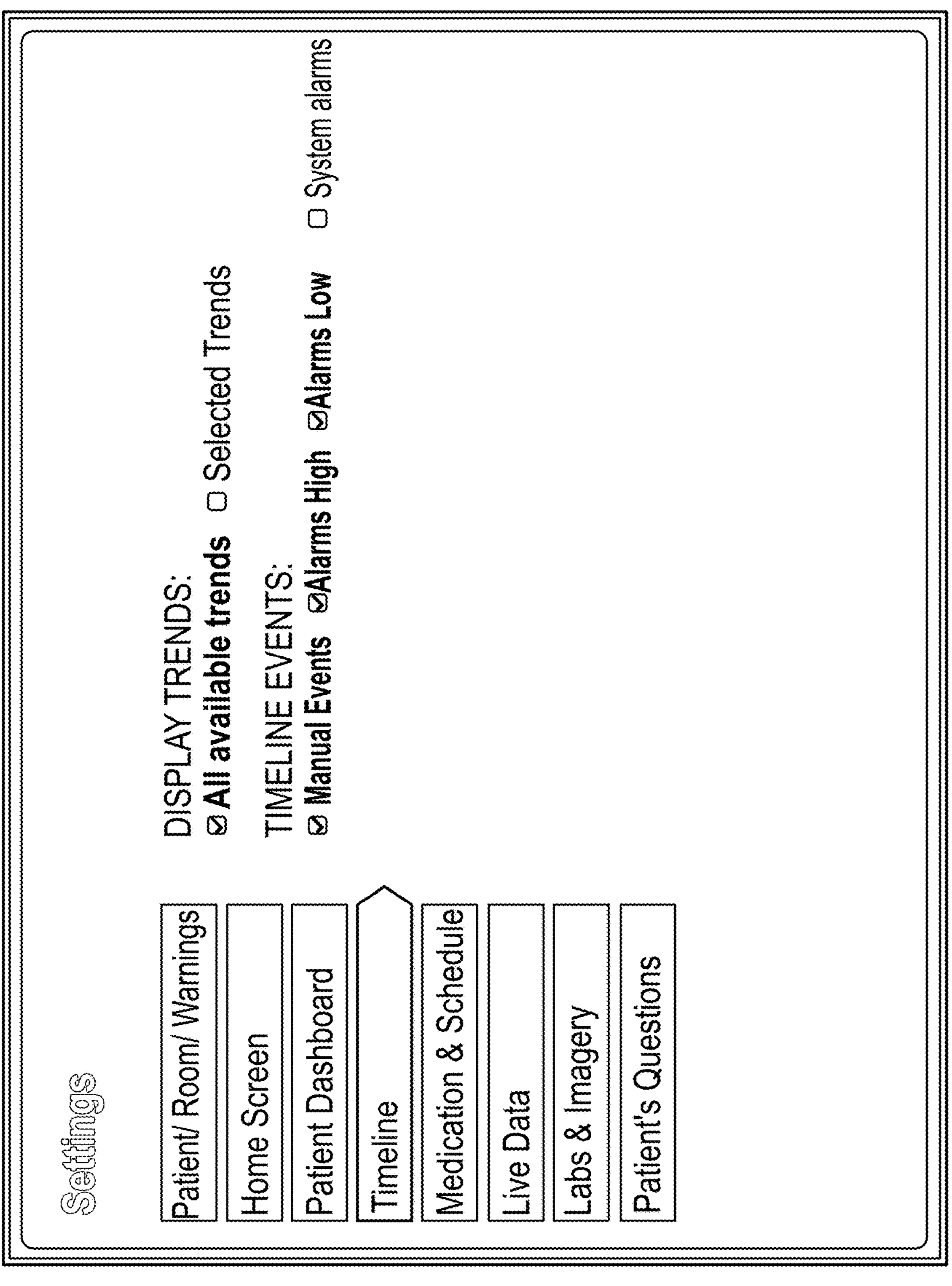
Figure 9M:
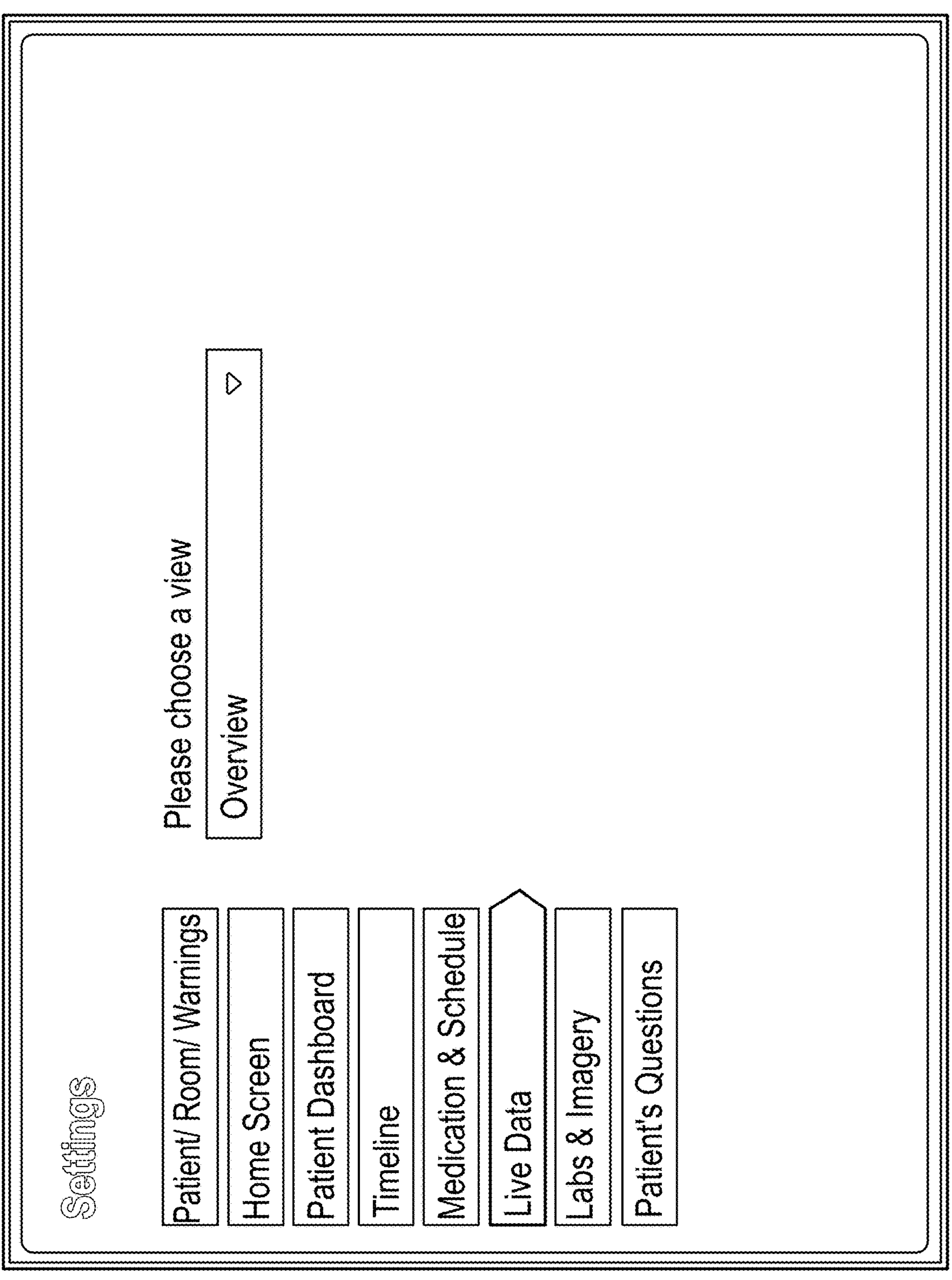
Figure 9N:
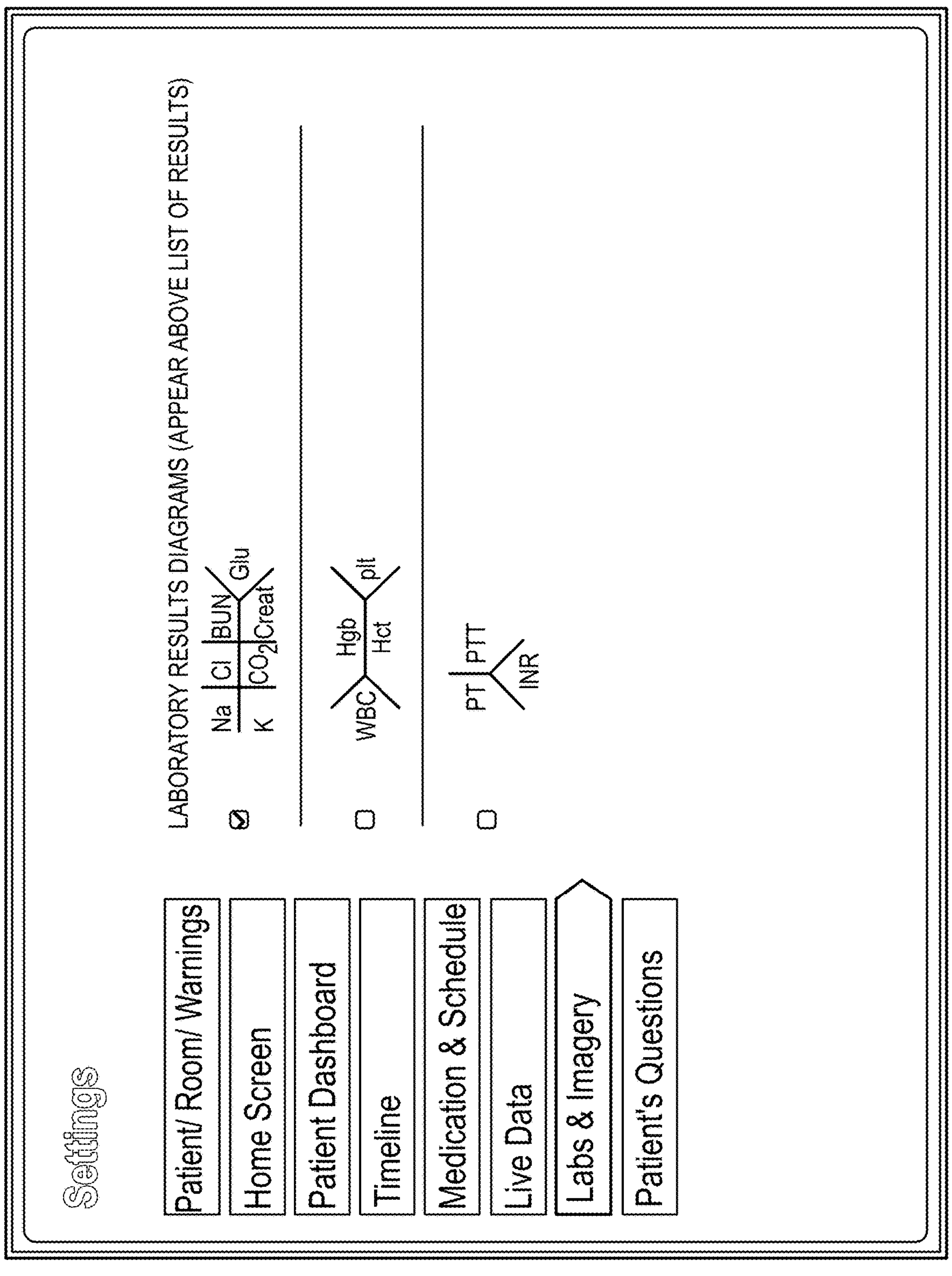
Figure 9O:
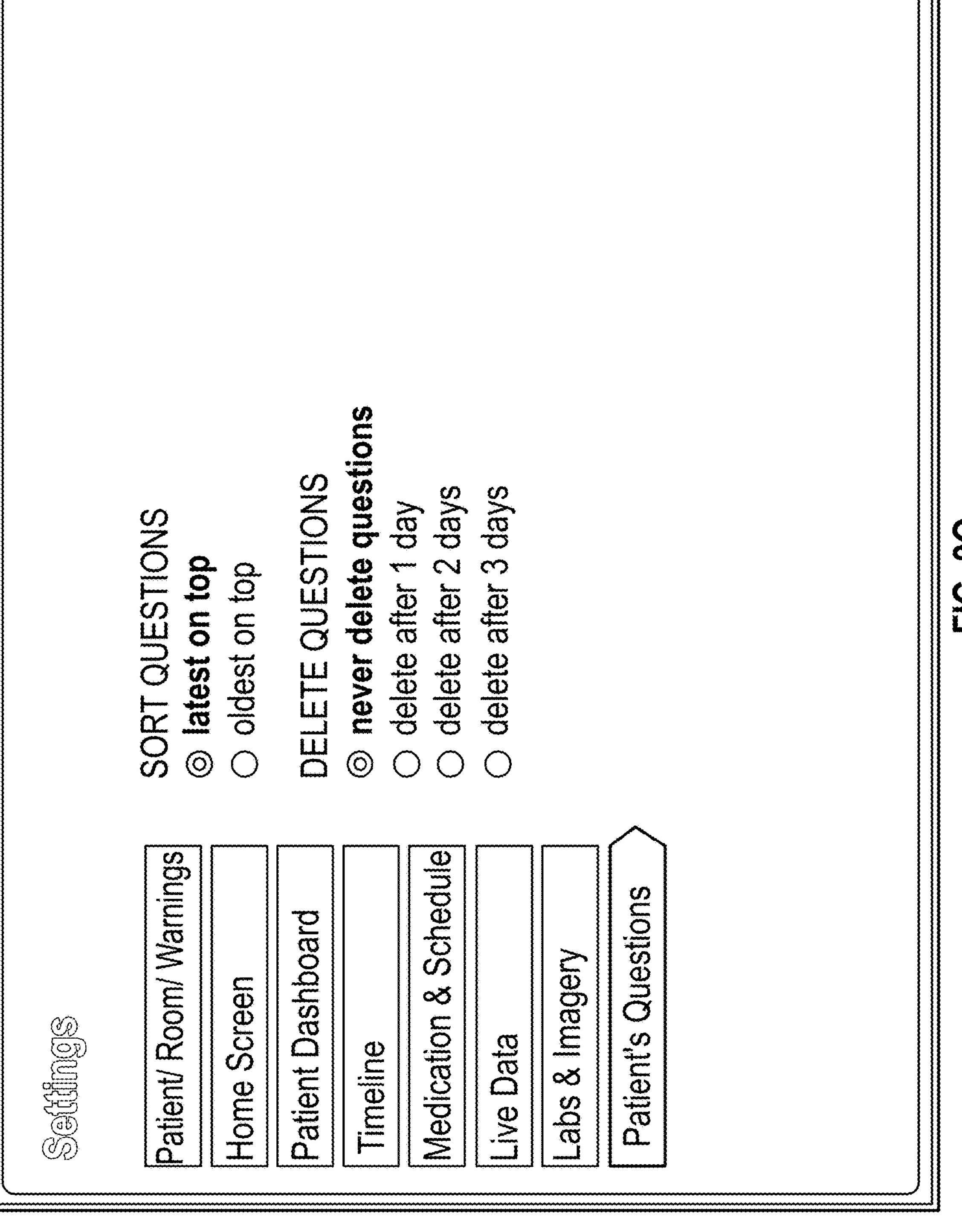

FIGS. 9A-9P illustrate various example pages of the application's settings where hospital staff can update patient information and display preferences. The settings may be accessed via the settings menu icon 205, 762. A navigation panel 900 may allow healthcare providers to edit the features displayed on the default screen 200 and each screen listed on the control panel 305. The settings screen may be used to change the application display to show the number of beds in a room, set default displays in cases where the device cannot connect to patient data, update patient information, update patient scheduling, update medication information, or customize and/or update any feature described herein.

Figure 10A:
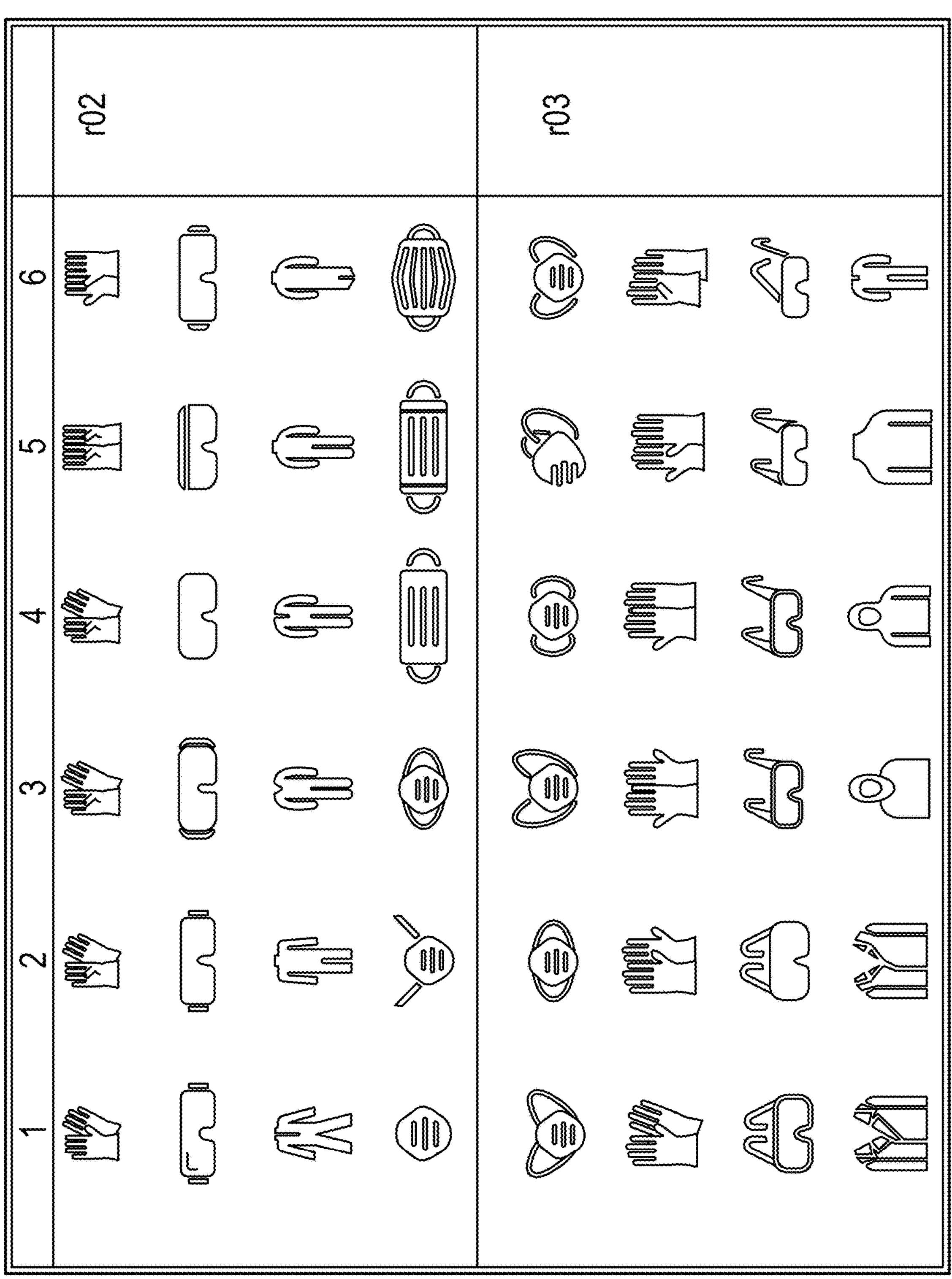
FIGS. 10A-10C depict potential variations of the symbols and warnings used in a physiological patient monitoring system.
Figures 10B, 10C:
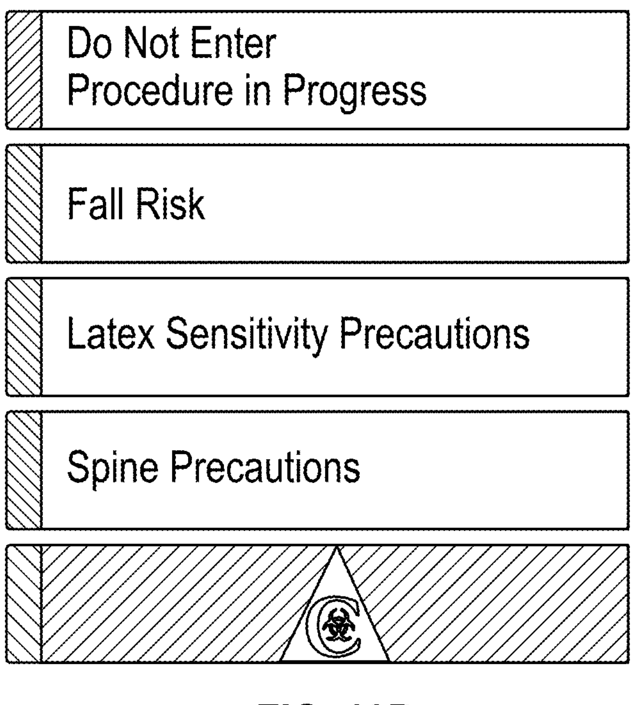

FIG. 10A illustrates potential variations of the safety precaution symbols used in the application. FIGS. 10B and 10C show lists of possible patient warnings that clinicians may choose for display on the interface default screen. FIGS. 10A-C should be understood to be non-limiting and do not preclude the use of other symbols and warnings not explicitly disclosed in the present figures.

Figure 11A:
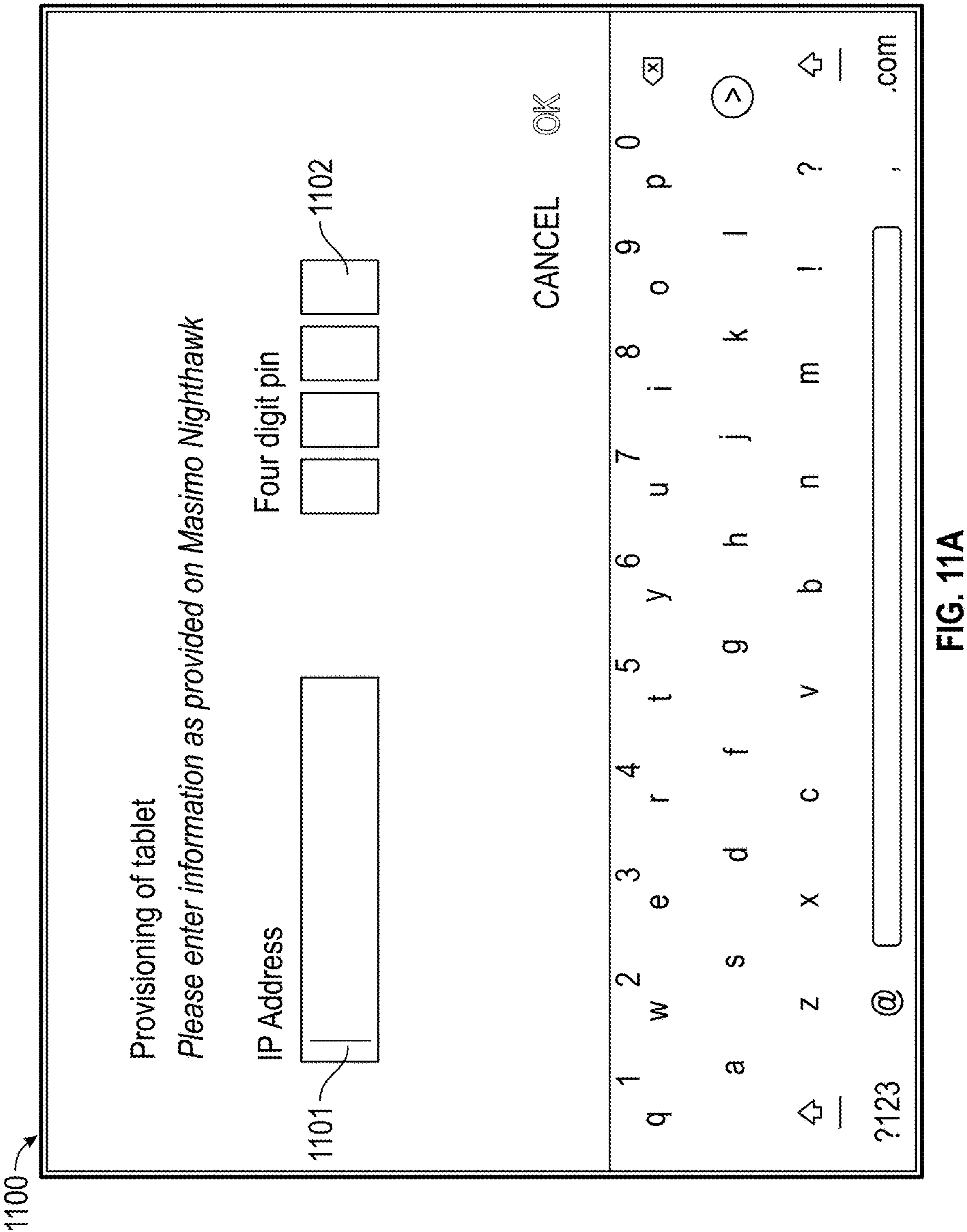
FIGS. 11A-11E are illustrative interfaces of clinician login pages to set up a physiological monitoring system for initial use, according to some embodiments.
Figure 11B:
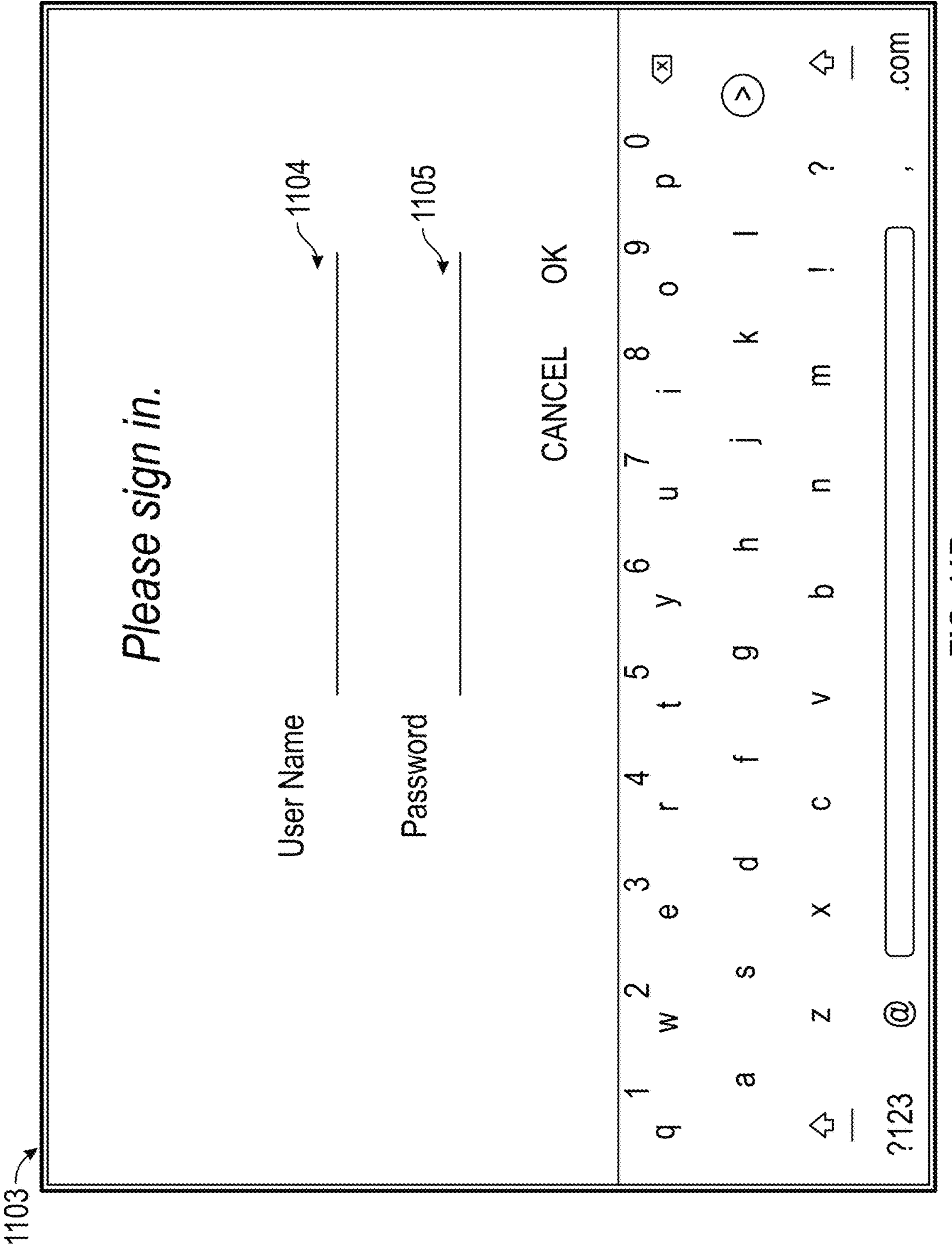
Figure 11C:
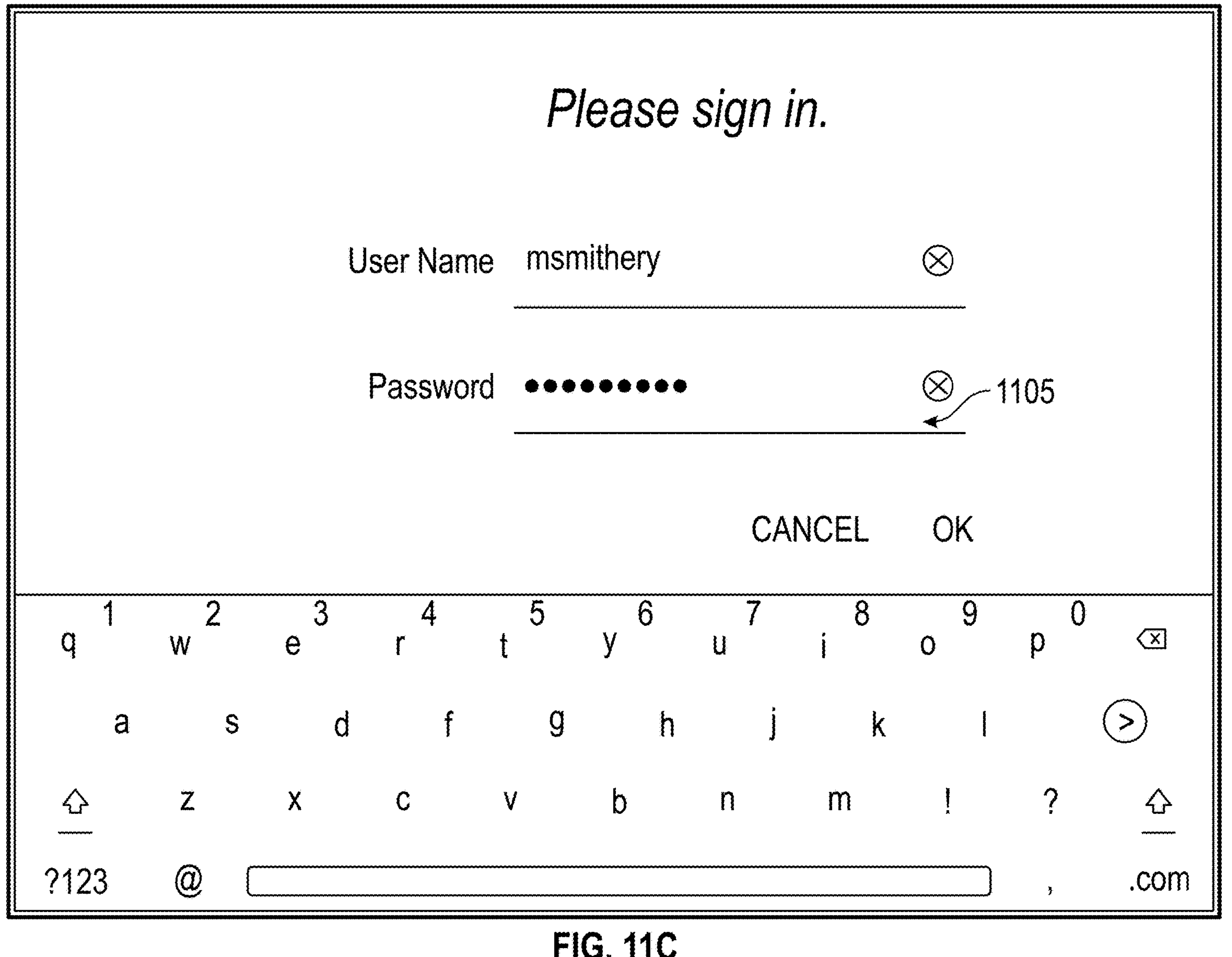
Figure 11D:
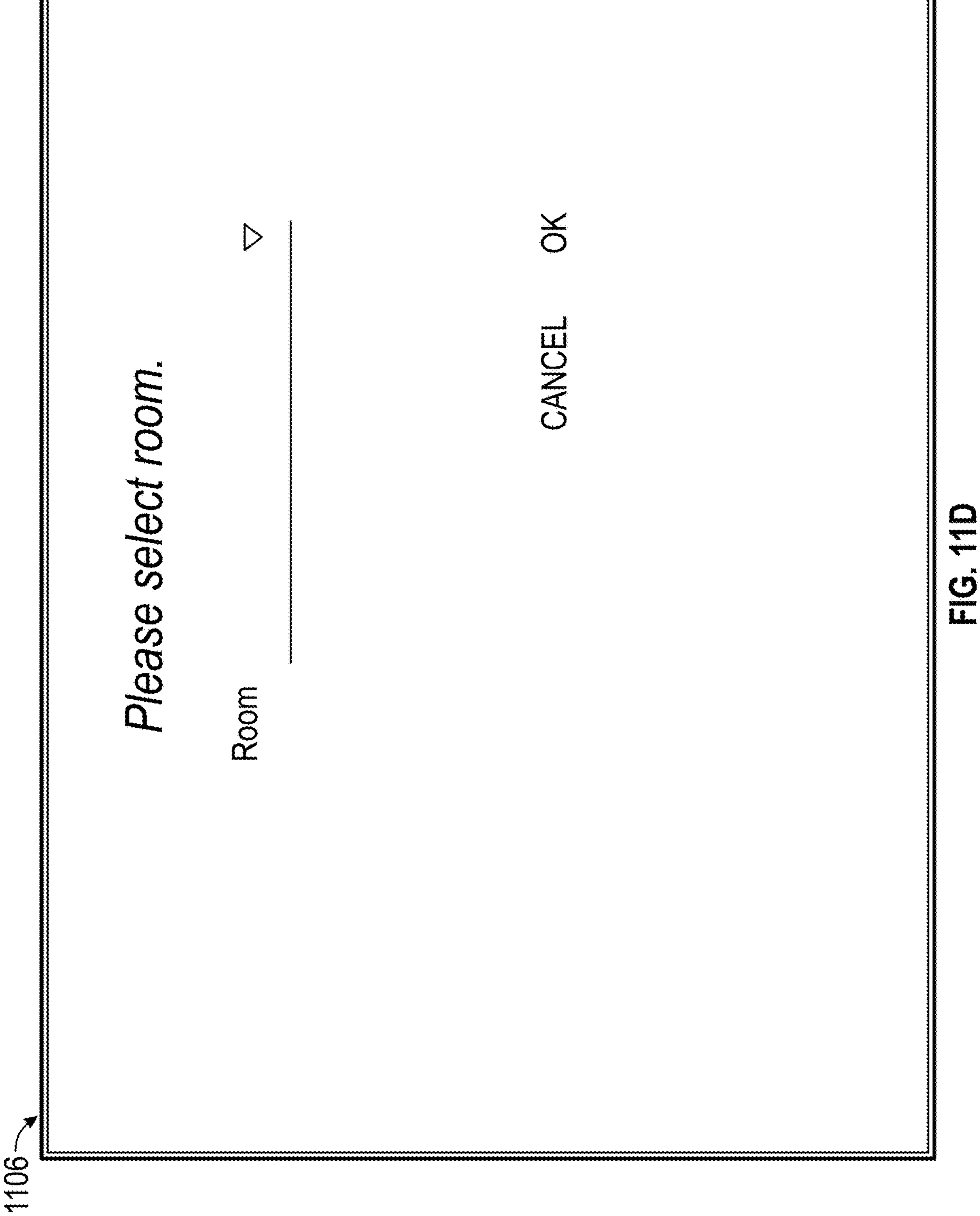
Figure 11E:
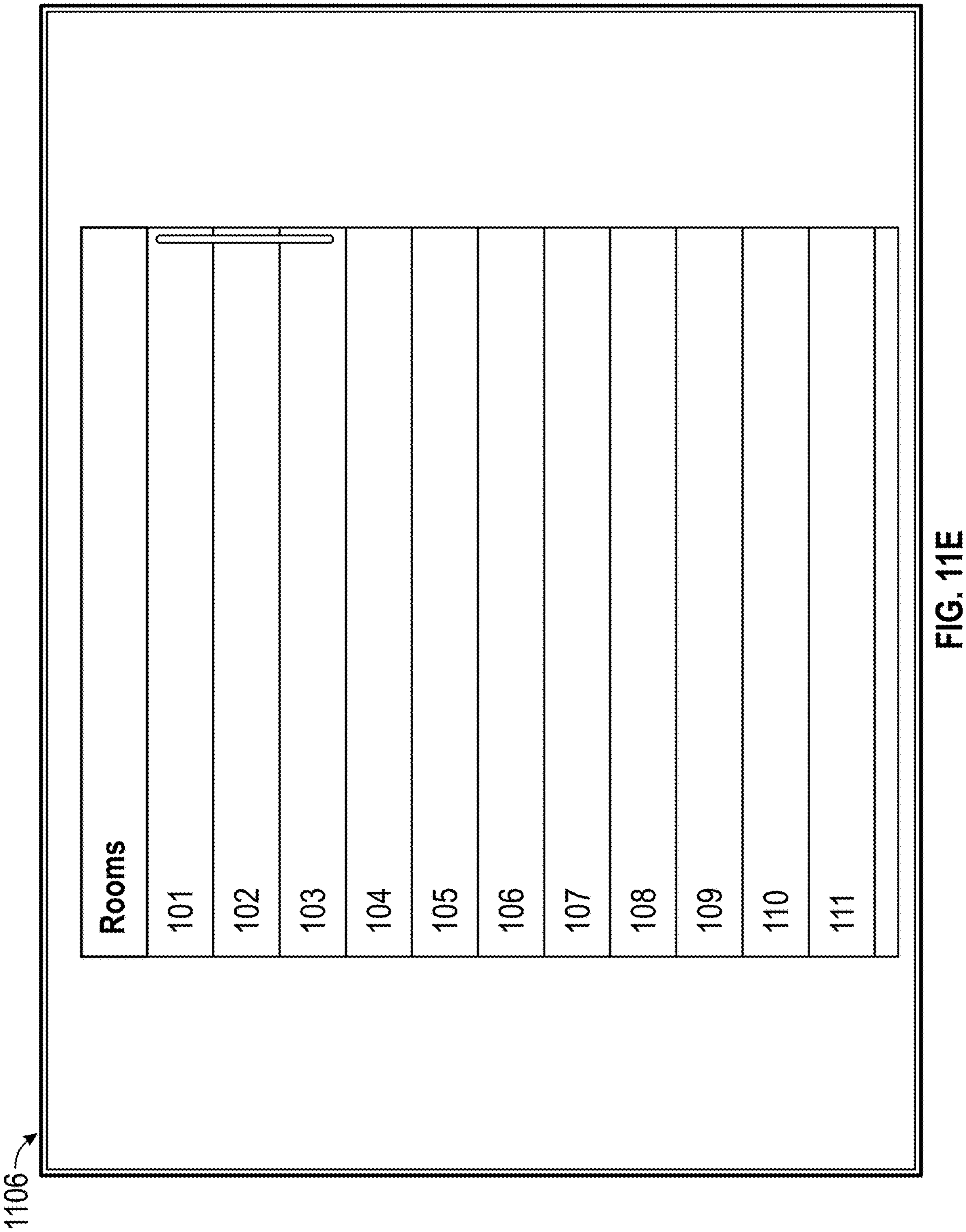

FIGS. 11A-E are exemplary configurations of set-up screens for the healthcare professional interface of the physiological patient monitoring. The set-up screens may appear prior to the first use of the application. FIG. 11A illustrates an example provisioning screen 1100 with an Internet Protocol ("IP") address input 1101 and PIN input 1102. In some configurations, the passcode may not be a four-digit PIN, but rather, may be any length and comprised of any combination of symbols, characters, or digits. Provisioning is particularly important for devices used in healthcare due to the sensitive and protected nature of patient information. Using the device IP address ensures that only verified devices may communicate with the network and access private patient data. FIGS. 11B-C show an illustrative login screen 1103 with user name input 1104 and password input 1105. As shown in FIG. 11C, the password input 1105 may censor the characters so that the passcode cannot be accidentally seen by un-intended audiences. In such configurations, there may be an additional option to reveal the password. FIGS. 11D & 11E are example room selection screens 1106. The room selection screen 1106 can allow system administrators to pair the device with a specific hospital room. FIG. 11E illustrates an example room selection screen 1106 where a room may be selected from a drop-down menu. In other configurations, the room number may be typed in via virtual keyboard.

The various features and processes described above may be used independently of one another or may be combined in various ways. All possible combinations and sub-combinations are intended to fall within the scope of this disclosure. In addition, certain interfaces and features may be omitted in some implementations. The interfaces described herein are also not limited to any particular sequence and may be arranged in other sequences that are appropriate. Features may be added to or removed from the disclosed example configurations. The example systems and components described herein may be configured differently than described. For example, elements may be added to, removed from, or rearranged compared to the disclosed example configurations Conditional language, such as, among others, "can," "could," "might," or "may," unless specifically stated otherwise, or otherwise understood within the context as used, is generally intended to convey that certain configurations include, while other configurations do not include, certain features, elements and/or steps. Thus, such conditional language is not generally intended to imply that features, elements and/or steps are in any way required for one or more configurations or that one or more configurations necessarily include logic for deciding, with or without user input or prompting, whether these features, elements and/or steps are included or are to be performed in any particular configuration.

It should be emphasized that many variations and modifications may be made to the above-described configurations, the elements of which are to be understood as being among other acceptable examples. All such modifications and variations are intended to be included herein within the scope of this disclosure. The foregoing description details certain configurations of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A system configured to be secured in proximity to a door outside a room in a hospital, the system comprising:
- a receptacle positioned in proximity to the door outside the room;
- a portable electronic device configured to be removably mounted to the receptacle;
- said portable electronic device comprising a display and one or more hardware processors configured to:
  - receive patient data from a healthcare data network, wherein the patient data corresponds to a patient in the room;
  - update the patient data from the healthcare data network in real time;
  - automatically generate safety information including a safety precaution for a care provider to enter the room based at least in part on the updated patient data;
  - generate a first user interface for presentation on the display, said first user interface configured to display only de-identified information corresponding to the patient in the room, including the generated safety information;
  - receive authentication data indicating that the care provider is authenticated to access the display; and
  - generate a second user interface for presentation on the display based on the received authentication data, said second user interface configured to display the patient data including identification information.

2. The system of claim 1, wherein to automatically generate the safety precaution for the care provider to enter the room, the one or more hardware processors are configured to:
- parse the patient data;
- identify listed risks to patient health in the patient data; and
- generate the safety information, based at least in part on the patient data.

3. The system of claim 1, wherein the receptacle comprises a mechanical locking mechanism configured to unlock the portable electronic device upon receipt of authentication.

4. The system of claim 1, wherein the receptacle comprises an electronically controlled locking mechanism configured to unlock the portable electronic device upon receipt of authentication.

5. The system of claim 1, wherein the portable electronic device is located at a nurse station or is carried by the care provider.

6. The system of claim 1, wherein the safety information further includes at least one of: patient allergies, recommended safety precautions, patient dietary regimen, procedure alert, or patient fall risk warning.

7. The system of claim 1, wherein the one or more hardware processors are further configured to:
- generate a third user interface for presentation on the display, said third user interface configured to display a safety information generation screen; and
- receive, via the third user interface, user input generating safety information.

8. The system of claim 1, wherein the one or more hardware processors are further configured to:
- process the updated patient data from the healthcare data network to generate graphical data displays;
- display, via a fourth graphical user interface, the graphical data displays; and
- update the graphical data displays based at least in part on the patient data updated in real time.

9. The system of claim 8, wherein the graphical data displays include at least one of: fishbone charts, timelines, or ECG waveforms.

10. The system of claim 1, wherein the authentication data includes at least one of: a passcode, a Personal Identification Number ("PIN"), a Radio Frequency Identification ("RFID") chip scanner, biometric information, or hardware provisioning.

11. The system of claim 1, wherein the one or more hardware processors are further configured to display patient x-rays.

12. The system of claim 1, wherein the portable electronic device is programmable to receive and display patient data for multiple patients in the room.

13. A method for monitoring patient physiological data, the method comprising:
- removably mounting a portable electronic device on a receptable, wherein the receptacle is positioned in proximity to a door outside a hospital room and wherein the portable electronic device comprises a display;
- connecting the portable electronic device to a healthcare data network; and
- configuring the portable electronic device to:
  - receive patient data from the healthcare data network, wherein the patient data corresponds to a patient in the room;
  - update the patient data from the healthcare data network in real time;
  - automatically generate safety information including a safety precaution for a care provider to enter the room based at least in part on the updated patient data;
  - generate a first user interface for presentation on the display, said first user interface configured to display de-identified information corresponding to the patient in the room, including the selected safety information;
  - receive authentication data indicating that the care provider is authenticated to access the display; and
  - generate a second user interface for presentation on the display based on the received authentication data, said second user interface configured to display the patient data including identification information.

14. The method of claim 13, wherein to automatically generate the safety precaution for the care provider to enter the room, the portable electronic device is further configured to:
- parse the patient data;
- identify listed risks to patient health in the patient data; and
- generate the safety information, based at least in part on the patient data.

15. The method of claim 13, wherein the portable electronic device is further configured to:
- generate a third user interface for presentation on the display, said third user interface configured to display a safety information selection screen; and
- receive, via the third user interface, user input selecting safety information.

16. The method of claim 13, wherein the portable electronic device is further configured to:
- process the updated patient data from the healthcare data network to generate graphical data displays;
- display, via a fourth graphical user interface, the graphical data displays; and
- update the graphical data displays based at least in part on the patient data updated in real time.

17. The method of claim 16, wherein the graphical data displays include at least one of: fishbone charts, timelines, or ECG waveforms.

18. The method of claim 13, wherein the authentication data includes at least one of: a passcode, a Personal Identification Number ("PIN"), a Radio Frequency Identification ("RFID") chip scanner, biometric information, or hardware provisioning.

19. The method of claim 13, wherein the portable electronic device is further configured to display patient x-rays.

20. The method of claim 13, wherein the portable electronic device is programmable to receive and display patient data for multiple patients in the room.

* * * * *